(12) United States Patent
Herman

(10) Patent No.: US 6,214,617 B1
(45) Date of Patent: Apr. 10, 2001

(54) CENTRIFUGAL FERMENTATION PROCESS

(75) Inventor: Heath H. Herman, Tucker, GA (US)

(73) Assignee: Kinetic Biosystems, Inc., Atlanta, GA (US)

( * ) Notice: Subject to any disclaimer, the term of this patent is extended or adjusted under 35 U.S.C. 154(b) by 0 days.

(21) Appl. No.: 09/224,645

(22) Filed: Dec. 31, 1998

Related U.S. Application Data

(63) Continuation-in-part of application No. 09/115,109, filed on Jul. 13, 1998, now Pat. No. 6,133,019, which is a continuation-in-part of application No. 08/784,718, filed on Jan. 16, 1997, now Pat. No. 5,821,116, which is a division of application No. 08/412,289, filed on Mar. 28, 1995, now Pat. No. 5,622,819.

(60) Provisional application No. 60/070,304, filed on Dec. 31, 1997, provisional application No. 60/070,251, filed on Dec. 31, 1997, provisional application No. 60/070,270, filed on Dec. 31, 1997, provisional application No. 60/070,133, filed on Dec. 31, 1997, provisional application No. 60/070,283, filed on Dec. 31, 1997, provisional application No. 60/070,078, filed on Dec. 31, 1997, and provisional application No. 60/070,301, filed on Dec. 31, 1997.

(51) Int. Cl.[7] ..................................................... C12N 5/00
(52) U.S. Cl. .......................... 435/394; 435/41; 435/68.1; 435/171; 435/348; 435/366; 435/410
(58) Field of Search .............................. 435/285.1, 286.1, 435/286.5, 286.7, 289.1, 813, 41, 68.1, 70.1, 71.1, 171, 348, 366, 394, 410

(56) References Cited

U.S. PATENT DOCUMENTS

| | | |
|---|---|---|
| 2,616,619 | 11/1952 | MacLeod . |
| 3,450,598 | 6/1969 | Welsh et al. . |
| 3,580,840 | 5/1971 | Uridil . |
| 3,717,551 | 2/1973 | Bizzini et al. . |
| 3,753,731 | 8/1973 | Christ . |
| 3,821,087 | 6/1974 | Knazek et al. . |
| 3,843,454 | 10/1974 | Weiss . |
| 3,865,695 | 2/1975 | Massier . |
| 3,871,961 | 3/1975 | Gianessi . |
| 3,883,393 | 5/1975 | Knazek et al. . |
| 3,928,142 | 12/1975 | Smith . |
| 3,941,662 | 3/1976 | Munder et al. . |
| 3,948,732 | 4/1976 | Haddad et al. . |
| 3,968,035 | 7/1976 | Howe ..................................... 210/15 |
| 3,997,396 | 12/1976 | Delente . |
| 4,001,090 | 1/1977 | Kalina . |
| 4,036,693 | 7/1977 | Levine et al. . |
| 4,059,485 | 11/1977 | Tolbert et al. . |

(List continued on next page.)

FOREIGN PATENT DOCUMENTS

| | | |
|---|---|---|
| 54-114474 | 11/1979 | (JP) . |
| 62-100279 | 5/1987 | (JP) . |

OTHER PUBLICATIONS

Lindahl, P.E., "Principle of a Counter–streaming Centrifuge for the Separation of Particles of Different Sizes", *Nature*, vol. 161, No. 4095, Apr. 24, 1948, pp. 648–649.

Morton, H., "A Survey of Commercially Available Tissue Culture Media", In Vitro, vol. 6, No. 2 (1970).

Sanderson et al., "Cell Separations by Counterflow Centrifugation", *Methods in Cell Biology*, vol. 15, Chapter 1, pp. 1–14 (1977).

Clark et al., "Optimizing Culture Conditions for the Production of Animal Cells in Microcarrier Culture", *Annals New York Academy of Sciences*, pp. 33–45 (1981).

*The Scientist*, vol. 8, No. 22, p. 16 (Nov. 14, 1994).

*Primary Examiner*—David A. Redding
(74) *Attorney, Agent, or Firm*—Kilpatrick Stockton LLP

(57) ABSTRACT

The present invention comprises a novel culture methods and devices in which living cells or subcellular biocatalysts are immobilized by the opposition of forces. The immobilized cells or biocatalysts may be attached to support complexes that add to the resultant vector forces.

16 Claims, 50 Drawing Sheets

U.S. PATENT DOCUMENTS

| | | | |
|---|---|---|---|
| 4,087,327 | 5/1978 | Feder et al. | |
| 4,113,173 | 9/1978 | Lolachi | |
| 4,114,802 | 9/1978 | Brown | |
| 4,148,689 | 4/1979 | Hino et al. | |
| 4,166,768 | 9/1979 | Tolbert et al. | |
| 4,169,010 | 9/1979 | Marwil | |
| 4,178,209 | 12/1979 | Tolbert et al. | |
| 4,184,916 | 1/1980 | Tolbert et al. | |
| 4,184,922 | 1/1980 | Knazek et al. | |
| 4,189,534 | 2/1980 | Levine et al. | 435/2 |
| 4,195,131 | 3/1980 | Papas | |
| 4,201,845 | 5/1980 | Feder et al. | |
| 4,203,801 | 5/1980 | Telling et al. | |
| 4,220,725 | 9/1980 | Knazek et al. | |
| 4,225,671 | 9/1980 | Puchinger et al. | 435/71 |
| 4,237,033 | 12/1980 | Scattergood | 260/6 |
| 4,237,218 | 12/1980 | Monthony et al. | 435/2 |
| 4,266,032 | 5/1981 | Miller et al. | |
| 4,279,753 | 7/1981 | Nielson et al. | 210/605 |
| 4,289,854 | 9/1981 | Tolbert et al. | |
| 4,293,654 | 10/1981 | Levine et al. | |
| 4,296,882 | 10/1981 | Kobayashi | 233/21 |
| 4,308,351 | 12/1981 | Leighton et al. | |
| 4,335,215 | 6/1982 | Tolbert et al. | |
| 4,372,484 | 2/1983 | Larsson et al. | |
| 4,391,912 | 7/1983 | Yoshida et al. | |
| 4,413,058 | 11/1983 | Arcuri et al. | |
| 4,425,112 | 1/1984 | Ito | 494/18 |
| 4,442,206 | 4/1984 | Michaels et al. | |
| 4,463,019 | 7/1984 | Okuhara et al. | 426/17 |
| 4,537,860 | 8/1985 | Tolbert et al. | |
| 4,546,085 | 10/1985 | Johannson et al. | |
| 4,557,504 | 12/1985 | Kuhns | 283/68 |
| 4,603,109 | 7/1986 | Lillo | 435/41 |
| 4,661,455 | 4/1987 | Hubbard | 435/240 |
| 4,683,062 | 7/1987 | Krovák et al. | 210/617 |
| 4,693,983 | 9/1987 | Davies et al. | |
| 4,722,902 | 2/1988 | Harm et al. | |
| 4,734,372 | 3/1988 | Rotman | |
| 4,748,124 | 5/1988 | Vogler | |
| 4,764,471 | 8/1988 | Ripka | |
| 4,774,187 | 9/1988 | Lehmann | |
| 4,804,628 | 2/1989 | Cracauer et al. | |
| 4,833,083 | 5/1989 | Saxena | 435/240.24 |
| 4,833,089 | 5/1989 | Kojima et al. | 435/313 |
| 4,837,390 | 6/1989 | Reneau | 435/1 |
| 4,839,292 | 6/1989 | Cremonese | |
| 4,851,354 | 7/1989 | Winston et al. | |
| 4,874,358 | 10/1989 | Brimhall et al. | 494/36 |
| 4,894,342 | 1/1990 | Guinn et al. | |
| 4,895,806 | 1/1990 | Le et al. | |
| 4,897,359 | 1/1990 | Oakley et al. | |
| 4,898,718 | 2/1990 | Cardoso | 422/211 |
| 4,908,319 | 3/1990 | Smyczek et al. | |
| 4,931,401 | 6/1990 | Safi | |
| 4,937,196 | 6/1990 | Wrasidlo et al. | |
| 4,939,087 * | 7/1990 | Van Wie et al. | |
| 5,151,368 | 9/1992 | Brimhall et al. | |
| 5,248,613 | 9/1993 | Roubicek | |
| 5,272,075 | 12/1993 | Anderson et al. | 435/183 |
| 5,622,819 * | 4/1997 | Herman | |
| 5,821,116 * | 10/1998 | Herman | |

* cited by examiner

FIGURE 37.

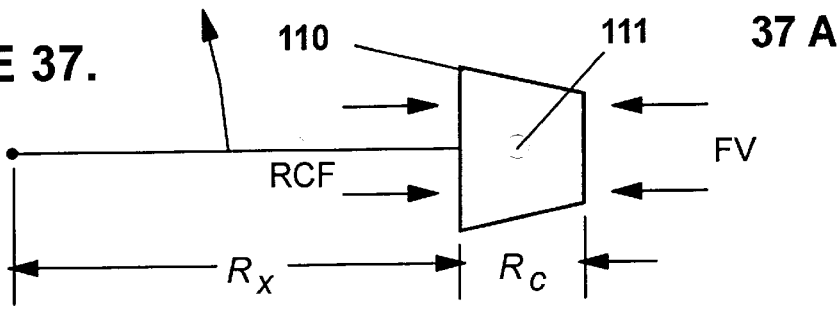

37 A

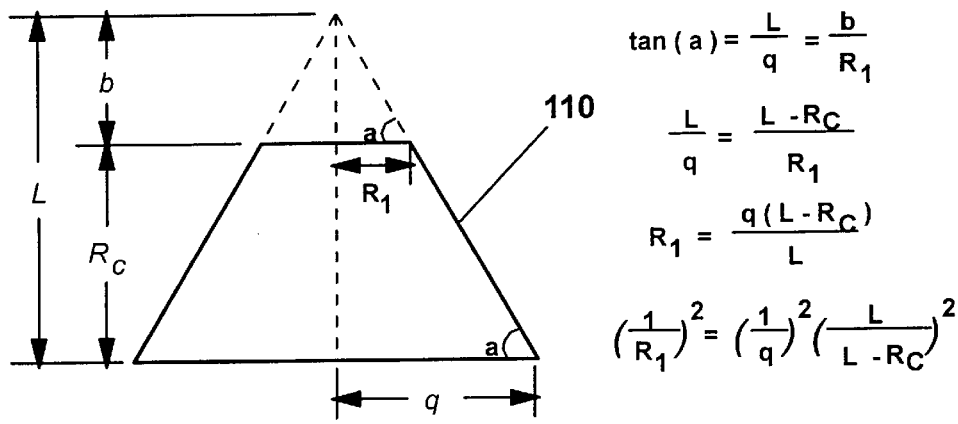

37 B $$\tan(a) = \frac{L}{q} = \frac{b}{R_1}$$

$$\frac{L}{q} = \frac{L - R_C}{R_1}$$

$$R_1 = \frac{q(L - R_C)}{L}$$

$$\left(\frac{1}{R_1}\right)^2 = \left(\frac{1}{q}\right)^2 \left(\frac{L}{L - R_C}\right)^2$$

Definitions:
RCF = Relative Centrifugal Force ( X g )   RPM = revolutions/min
FR = Flow Rate (mm³ /min)   R = centrifugal radius (mm)
FV = Flow Velocity (mm/min)   SR = Sedimentation Rate (mm/min)

at $R_X$:

(1) $RCF = w^2 R = (1.12) \left(\frac{RPM}{1000}\right)^2 (R_X)$      (2) $FV = \frac{FR}{\pi \cdot q^2}$ at $R_X + R_C$:

(3) $RCF = w^2 R = c_1 (R_X + R_C)$      (4) $FV = \frac{FR}{\pi \cdot q^2} \left(\frac{L}{L - R_C}\right)^2 = c_2 \left(\frac{L}{L - R_C}\right)^2$ where $c_1 = (1.12) \left(\frac{RPM}{1000}\right)^2$      where $c_2 = \frac{FR}{\pi \cdot q^2}$

CENTRIFUGAL FERMENTATION PROCESS

CROSS-REFERENCE TO RELATED APPLICATIONS

This application claims priority to U.S. Provisional Patent Applications Nos. 60/070,304; 60/070,251; 60/070,270; 60/070,133; 60/070,283; 60/070,078; 60/070,301 all filed Dec. 31, 1997, and this application is a continuation-in-part of U.S. patent application Ser. No. 09/115,109, filed Jul. 13, 1998, now U.S. Pat. No. 6,133,019, which is a continuation-in-part of U.S. patent application Ser. No. 08/784,718, filed Jan. 16, 1997, now U.S. Pat. No. 5,821,116, which is a division of U.S. patent application Ser. No. 08/412,289, filed Mar. 28, 1995, now U.S. Pat. No. 5,622,819.

FIELD OF THE INVENTION

The present invention relates to an improved method and apparatus for the continuous culture of biocatalysts. More particularly, the present invention relates to a method and apparatus for culturing micro-organisms, or plant or animal cells, or subcellular cell components as three-dimensional arrays immobilized in centrifugal force fields which are opposed by liquid flows. The present invention allows the maintenance of extremely high density cultures of biocatalysts and maximizes their productivity.

BACKGROUND OF THE INVENTION

The term "fermentation" as used herein means any of a group of chemical reactions induced by living or nonliving biocatalysts. The term "culture" as used herein means the suspension or attachment of any such biocatalyst in or covered by a liquid medium for the purpose of maintaining chemical reactions. The term "biocatalysts" as used herein, includes enzymes, vitamins, enzyme aggregates, immobilized enzymes, subcellular components, prokaryotic cells, and eukaryotic cells. The term "centrifugal force" means a centripetal force resulting from angular rotation of an object when viewed from a congruently rotating frame of reference.

The culture of microbial cells (fermentation) or animal and plant cells (tissue culture) are central to a multiplicity of commercially-important chemical and biochemical production processes. Living cells are employed in these processes as a result of the fact that living cells, using generally easily obtainable starting materials, can economically synthesize commercially-valuable chemicals.

Fermentation involves the growth or maintenance of living cells in a nutrient liquid media. In a typical batch fermentation process, the desired micro-organism or eukaryotic cell is placed in a defined medium composed of water, nutrient chemicals and dissolved gases, and allowed to grow (or multiply) to a desired culture density. The liquid medium must contain all the chemicals which the cells require for their life processes and also should provide the optimal environmental conditions for their continued growth and/or replication. Currently, a representative microbial cell culture process might utilize either a continuous stirred-tank reactor or a gas-fluidized bed reactor in which the microbe population is suspended in circulating nutrient media. Similarly, in vitro mammalian cell culture might employ a suspended culture of cells in roller flasks or, for cells requiring surface, attachment, cultures grown to confluence in tissue culture flasks containing nutrient medium above the attached cells. The living cells, so maintained, then metabolically produce the desired product(s) from precursor chemicals introduced into the nutrient mixture. The desired product(s) are either purified from the liquid medium or are extracted from the cells themselves.

Examples of methods employing fermentations of cells growing in either agitated aqueous suspension or with surface attachment are described, for example, in U.S. Pat. Nos. 3,450,598; 3,843,454; 4,059,485; 4,166,768; 4,178,209; 4,184,916; 4,413,058; and 4,463,019. Further reference to these and other such conventional cell culturing techniques may be found in such standard texts as Kruse and Patterson, Tissue Culture Methods and Applications, Academic Press, New York, 1977; and Collins and Lyne's Microbiological Methods, Butterworths, Boston, 1989.

There are a number of disadvantages inherent in such typical fermentation processes. On a commercial scale, such processes require expensive energy expenditures to maintain the large volumes of aqueous solution at the proper temperature for optimal cell viability. In addition, because the metabolic activity of the growing cell population causes decreases in the optimal levels of nutrients in the culture media and causes changes in the media pH, the process must be continuously monitored and additions must be made to maintain nutrient concentration and pH at optimal levels.

In addition, the optimal conditions under which the desired cell type may be cultured are usually near the optimal conditions for the growth of many other undesirable cells or microorganisms. Extreme care and expense must be taken to initially sterilize and to subsequently exclude undesired cell types from gaining access to the culture medium. Next, such fermentation methods, particularly those employing aerobic organisms, are quite often limited to low yields of product or low rates of product formation as a result of the inability to deliver adequate quantities of dissolved oxygen to the metabolizing organism. Finally, such batch or semi-batch processes can only be operated for a finite time period before the buildup of excreted wastes in the fermentation media require process shutdown followed by system cleanup, resterilization, and a re-start.

The high costs associated with the preparation, sterilization, and temperature control of the large volumes of aqueous nutrient media needed for such cultures has led to the development of a number of processes whereby the desired cell type or enzyme can be immobilized in a much smaller volume through which smaller quantities of nutrient media can be passed. Cell immobilization also allows for a much greater effective density of cell growth and results in a much reduced loss of productive cells to output product streams. Thus, methods and processes for the immobilization of living cells are of considerable interest in the development of commercially valuable biotechnologies.

An early method for the immobilization of cells or enzymes involved the entrapment of such biocatalysts on or within dextran, polyacrylamide, nylon, polystyrene, calcium alginate, or agar gel structures. Similarly, the ability of many animal cells to tenaciously adhere to the external surface of spherical polymeric "microcarrier beads" has likewise been exploited for the immobilization of such cells. These gel- or bead-immobilization methods effectively increase the density of the biocatalyst-containing fraction, thereby effectively trapping these structures in the lower levels of relatively slow-flowing bioreactor chambers. Such gel-entrapment or microcarrier-immobilized methods are taught, for example, in U.S. Pat. Nos. 3,717,551; 4,036,693; 4,148, 689; 4,189,534; 4,203,801; 4,237,033; 4,237,218; 4,266, 032; 4,289,854; 4,293,654; 4,335,215; and 4,898,718. More background information on cell immobilization techniques is discussed in Chibata, et al., "Immobilized Cells in the Preparation of Fine Chemicals", Advances in Biotechnological Processes, Vol. I, A.R. Liss, Inc., New York, 1983. See also Clark and Hirtenstein, Ann. N.Y. Acad. Sci. 369, 33–45 (1981), for more background information on microcarrier culture techniques.

These immobilization methods suffer from a number of drawbacks. First, such entrapment of cells within gels has been shown to interfere with the diffusion of gases (particularly oxygen and carbon dioxide) into and out of the cell environment, resulting in either low cell growth (reduced oxygen input) or gel breakage (high internal $CO_2$ pressure). In addition, the poor mechanical properties and high compressibility of gel-entrapment media lead to unacceptably high pressure problems in packed bed bioreactors. Similarly, the crushing of microcarrier beads and the destruction of attached cells by hydraulic shear forces in agitated tank bioreactors (necessary to increase gas exchange) leads to reduced viability and productivity.

Another method for the immobilization of living cells or enzymes currently in use involves the use of packed-bed bioreactors. In these methods, free cells or cells bound to microcarrier beads are suspended in a rigid or semi-rigid matrix which is placed within a culture bioreactor. The matrix possesses interstitial passages for the transport of liquid nutrient media into the bioreactor, similarly disposed passages for the outflow of liquid media and product chemicals, and similar interstitial passages through which input and output gases may flow. Bioreactors of this type include the vat type, the packed-column type, and the porous ceramic-matrix type bioreactor. Such methods are taught, for example, in U.S. Pat. Nos. 4,203,801; 4,220,725; 4,279,753; 4,391,912; 4,442,206; 4,537,860; 4,603,109; 4,693,983; 4,833,083; 4,898,718; and 4,931,401.

These methods of immobilization all suffer from a number of problems, particularly when scaled up to production size. First of all, such bioreactors are subject to concentration gradients. That is, the biocatalysts nearer the input nutrient liquid feed see higher substrate levels than those farther downstream. Conversely, those biocatalysts farther from the input liquid stream (and closer to the exit liquid port) see increased concentrations of waste products and often suffer suboptimal environmental conditions, such as a changed pH and/or lowered dissolved oxygen tension. Next, such bioreactors are particularly susceptible to the "bleeding" of biocatalysts detached from the matrix (or released by cell division), with the result that output ports become clogged with cells and/or debris. The result is an unacceptable pressure drop across the bioreactor which causes further deterioration of production. Finally, such vertical packed-bed bioreactors in which glass or other microcarrier beads are packed subject the lower portion of the bed to the weight of those beads above, with the inevitable result that both beads and cells are crushed by the sheer weight and number of beads needed for production-scale columns.

A more recently-developed class of methods for cell immobilization involves the confinement of the desired cells between two synthetic membranes. Typically, one membrane is microporous and hydrophilic and in contact with the aqueous nutrient media, while the opposing membrane is ultraporous and hydrophobic and in contact with a flow of air or an oxygen-enriched gas. Such processes thus provide the cells with an environment in which nutrient liquid input and waste liquid output can occur through channels separate from the cell-containing space and similarly provide gaseous input and output through similarly disposed channels, again separate from the cell-containing space. Embodiments of methods of this class have utilized stacks of many flat membranes forming a multiplicity of cell compartments, have utilized series of synthetic membrane bags, one within the other, and have utilized spirally-wound membrane configurations. Such methods are taught, for example, in U.S. Pat. Nos. 3,580,840; 3,843,454; 3,941,662; 3,948,732; 4,225,671; 4,661,455; 4,748,124; 4,764,471; 4,839,292; 4,895,806; and 4,937,196.

Unfortunately, there are a number of problems with such methods, particularly for any commercial, large-scale usage. First, such devices in which a multiplicity of membranes are stacked in series are quite costly to manufacture and are extremely difficult to correctly assemble. Next, the requirement that the membrane which separates the nutrient channels from the immobilized cells be hydrophilic necessarily results in cell attachment across pores, and/or pore clogging by insolubles in either the nutrient feed or waste output liquids which wet this membrane. The result is the development over time of "dead pockets" where cell growth cannot occur. This situation greatly reduces the effective cell concentration and lowers product yield. Finally, these methods involve devices with a large number of inlet and outlet ports and external fittings which substantially increase both cost and the probability that leakage and contamination will occur.

Another class of methods for cell immobilization involves the employment of capillary hollow fibers (usually configured in elongated bundles of many fibers) having micropores in the fiber walls. Typically, cells are cultured in a closed chamber into which the fiber bundles are placed. Nutrient aqueous solutions flow freely through the capillary lumena and the hydrostatic pressure of this flow results in an outward radial perfusion of the nutrient liquid into the extracapillary space in a gradient beginning at the entry port. Similarly, this pressure differential drives an outward flow of "spent" media from the cell chamber back into the capillary lumena by which wastes are removed. Cells grow in the extracapillary space either in free solution or by attachment to the extracapillary walls of the fibers. Typically, oxygen is dissolved into the liquid fraction of the extracapillary space by means of an external reservoir connected to this space via a pump mechanism. Waste products in the intracapillary space may be removed by reverse osmosis in fluid circulated outside of the cell chamber. Such methods are taught, for example, by U.S. Pat. Nos. 3,821,087; 3,883,393; 3,997,396; 4,087,327; 4,184,922; 4,201,845; 4,220,725; 4,442,206; 4,722,902; 4,804,628; and 4,894,342. There are a number of difficulties with the use of methods based on capillary hollow fiber cell immobilization methods.

Cracauer et al. (U.S. Pat. No. 4,804,628) have extensively documented these difficulties. These difficulties include: (1) an excessive pressure drop through the fiber assembly (The fragile nature of the fibers results in complete breakdown if fiber of production-scale length is required.); (2) the occurrence of adverse chemical gradients within the cell chamber (Gradients of nutrients and waste products often occur in such chambers.); (3) the formation of anoxic pockets and discrete disadvantageous microenvironments within the cell chamber (Because of the inaccessibility of liquids, gases, and cells to all portions of the fiber bundle as a result of their design, not all areas of the cell chamber are equally effective in cell production.); and (4) either mass-transfer limitations in nutrient feed or limitations in product output increase with time. (As cells grow to higher densities, they tend to self-limit the capacities of the hollow fiber chambers (see Col. 1, lines 53–66, of U.S. Pat. No. 4,804,628)).

Another class of methods for the mass culture of living cells involves the use of fluidized bed bioreactors. The excellent mixing characteristics and fluid dynamics of this type of mass culture have found usage in both microbial and bead-immobilized animal cell culture. The major disadvantage of fluidized bed methods, and particularly a variant called airlift fermentors, results from the necessity of bubbling air or oxygen through the bioreactor and the resultant presence of a gas-liquid interface throughout the bioreactor volume. Firstly, the presence of gas bubbles in the flowing liquid disrupts the fluid dynamics which provide the initial advantages of fluidized beds (uniform particle suspension). Next, protein foaming, cell destruction, and the denaturation of nutrients and products occurs at the large gas-liquid interface. Finally, cell washout is almost inevitable in continuous operation, particularly with animal cell culture.

Another class of methods for mass cell culture is known as dual axis, continuous flow bioreactor processing. Such methods are taught by, for example, U.S. Pat. Nos. 5,151,368, 4,296,882, and 4,874,358. In this class of bioreactor, rotation of the bioreactor chamber about an axis perpendicular to the vertical axis is utilized in order to effect internal mixing of the bioreactor contents while rotation about the vertical axis confines grossly particulate matter at radial distances far from the vertical axis of rotation. Input nutrient liquids and gases are supplied by concentric flexible conduits into the bioreactor and output liquids and gases are removed by similar flexible conduits concentric with the input tubings. While the intended purpose of bioreactors of this class is to allow continuous flow of liquid into and out of a bioreactor chamber in which a combination of solids and liquids is suspended and mixed, such processes are limited to rotational speeds at which effective mixing can occur without appreciable negation by centrifugal forces. As a result, methods of this class are ineffective in the immobilization of low mass micro-organisms, particularly those requiring gaseous nutrients and producing waste gas products. Other similar centrifugal liquid processing apparati are disclosed in U.S. Pat. Nos. 4,113,173, 4,114,802, 4,372,484, and 4,425,112. In each of these latter references, liquid flow through a centrifugal chamber is supplied by flexible tubing extending through the rotational axis.

Another type of bioreactor called a "Nonhomogeneous Centrifugal Film Bioreactor" intended for aerobic cell culture is taught by U.S. Pat. No. 5,248,613. The object of the method is to maximize the "entrainment of the maximum amount of the gaseous phase into the liquid phase" by causing the formation of a thin liquid film to contact the gas phase and further, to centrifugally generate small liquid droplets which fall through a relatively stationary gas phase back into the recirculated bulk liquid phase. There are a number of problems associated with a bioreactor design of this type. First of all, it is a "batch" process. That is, the nutrient liquid phase gradually is depleted of its components while liquid metabolic wastes build up, necessitating a limited culture time. Secondly, the scale of such a bioreactor is limited by the quantity of nutrient gas (such as oxygen) which can be dissolved in the various gas-liquid transfer regions. In the limit, the maximum gas transfer obtainable at atmospheric pressure will determine the maximum cell "load" which can be carried by the bioreactor system. Next, the lack of any provision for the removal of waste gases (such as carbon dioxide) will result in disruption of both bulk liquid pH as well as cellular productivity as culture periods extend to longer times. Finally, it is extremely doubtful that accelerated productive cell loss could be avoided if animal cells were subjected to passage through a high flow-rate, thin-film liquid region where cell-disrupting surface-tension forces are maximal, and where there is limited nutrient availability due to the presence of maximum aerobicity.

A final method for the mass immobilization of living cells called "Continuous Centrifugal Bioprocessing" has been taught by Van Wie, et al. (U.S. Pat. No. 4,939,087). In this method cells are "captured" by a velocity gradient in a centrifugal field in order to maintain a culture in a revolving bioreactor chamber into which and out of which liquid flows are pumped. The basic idea upon which the invention of Van Wie et al. is based was first postulated by Lindahl in 1948 (Lindahl, P. E. (1948) Nature (London) 161, 648–649) and a U.S. Patent awarded in the same year to MacLeod (U.S. Pat. No. 2,616,619). More recently, Beckman Instruments has developed analytical devices called "Centrifugal Elutriation Systems" based on the general principles of what is termed "Counterflow Centrifugation." The particle and fluid dynamic theory upon which these devices were constructed and refined has been most completely discussed by Sanderson and Bird (Sanderson, R. J. and Bird, K. E. (1977) Methods in Cell Biology, 15, 1–14). As is shown in FIG. 1, the basic idea is to suspend a particle in a spinning bioreactor chamber, which as a consequence of its rotation, imparts a "centrifugal" force to the particle which would normally cause the particle to migrate to longer centrifugal radii. Liquid flow is introduced into the periphery of the spinning chamber (and withdrawn at shorter radii) in order to impart an opposing force which counteracts that of the centrifugal field. The result is that the particle is immobilized at a particular radial distance in a liquid flow. The essence of Sanderson and Bird's mathematical analysis of the particle and fluid dynamics of this process are displayed in FIG. 2. As do all theoretical discussions of centrifugation theory, Sanderson and Bird's analysis begins with the application of Stoke's Law at low Reynolds numbers, an expression which governs the motion of a particle moving through an incompressible fluid (Eqn. 1). Briefly, the law states that the sedimentation velocity (SV) of a non-deformable particle moving through a stationary liquid under the influence of a centrifugal field is proportional to the square of the angular velocity ($\omega^2 r$) of the rotating system at radius r multiplied by the following expression: the square of the effective diameter of the particle (d) multiplied by the difference between the density of the particle and the density of the liquid ($\rho_p - \rho_m$) divided by the product of the liquid viscosity ($\mu$) and the "shape constant" of the particle (k, its deviation from sphericity). As was recognized first by Lindahl, the same equation applies to a stationary particle in a moving liquid flow. The analysis of Sanderson and Bird led to the derivation of Eqn. 2, an expression which states that "there is a radius $r_x$ (defined by evaluation of Eqn. 2) at which a particle is immobilized in a liquid flowing at velocity (V) in an centrifugal field (the parameters of Eqn. 2 are those defined above where ($\rho_p - \rho_m$) has been replaced by ($\rho'$). These authors further conclude that the contribution of the coriolis force to the net motion of the particle is negligible since it is limited to a tangential plane.

This theory, when applied to Centrifugal Elutriation, (as it was by Sanderson and Bird and by developers at Beckman Instruments) can be utilized in the short term for the separation of cells of different size and/or density. Unfortunately, this theory is completely inapplicable to long-term immobilization of cells or biocatalysts (as is implicit in U.S. Pat. No. 4,939,087) since the theoretical basis is incorrect. As is shown in FIG. 3, there is an additional force acting on the suspended particle which must be taken into account, particularly when the particle is to be immobilized over long time periods (as would be the case in fermentations). This additional force is a result of the particle's mass. Whereas micro-organisms or animal cells are quite light in weight, their mass is non-zero. Consequently, gravity will have a significant effect on the particle, and this effect will increase with time. This is shown graphically in FIG. 4, where it is shown that there is not a simple description of a radial distance where a particle in an applied centrifugal field can be immobilized in a flowing liquid since the derivation has neglected to consider the effect of gravity on the mass of the particle. The result of this "deviation from theory" is evident in centrifugal elutriation experiments which require prolonged separation times and is shown graphically in FIG. 5. Over longer time periods, the weight of the suspended particles (shown in FIG. 5 as dark circles in a circular cross-section of a biocatalyst immobilization chamber) will cause these particles to settle to the lowest regions of the biocatalyst immobilization chamber, disrupting the balance of forces which initially suspended them in the chamber. Further, the "aggregation" of these particles into a larger "particle" with virtually the same density as the individual particles results in an increased centrifugal effect which causes the aggregates to migrate to longer radii, eventually clogging the liquid input port.

There are several additional disadvantages to the "Continuous Centrifugal Bioprocessing" art taught by U.S. Pat. No. 4,939,087. First of all, the method is seriously limited by its design (which includes clockwork-like gear assemblies and moving flexible tube inputs and output lines) to low-speed operation. This means that the method could be used neither for the culture of low-mass micro-organisms nor large scale cultures of high mass cells in which the required liquid flow rates for adequate nutrition of the cultures would require rotational rates greatly in excess of those allowable by the apparatus in order to provide a counter-acting "centrifugal" force. Next, the method by which gaseous air/carbon dioxide is introduced into the bioreactor chamber (a gas-permeable flexible tube in contact with similar flexible tubes which transport input and output liquid flows) will greatly limit the scale of the apparatus since, very rapidly, the required aeration to support cell viability will be limited by the physical pressure and diffusion limits of the flexible tubing. Finally, the apparatus of Van Wie, et al. makes no provision for the vigorous outgassing of, for example, carbon dioxide which will occur as a result of cell metabolism. The metabolically produced gases will: (1) greatly disrupt the input gas exchange necessary for viability by limiting the liquid surface area in contact with the gas-permeable tubing; (2) greatly limit the efficient function of the pumping mechanisms necessary for liquid flow into and out of the apparatus; (3) result in the growth of gas pockets in the upper portions of the horizontally rotating bioreactor chamber with a resultant decrease of effective bioreactor volume and cell loss by bubble entrainment; and (4) result in serious rotor balance problems.

The prior art demonstrates that while cell immobilization is a greatly desired method for increasing the productivity of living cells in culture, there are a number of drawbacks associated with each class of method. A central problem of all such culture methods is, as Wrasidlo et al. (U.S. Pat. No. 4,937,196) assert, that "adequate oxygenation of the cultured cells and removal of carbon dioxide has been a limiting factor in the development of more efficient and economical designs" (see Col. 1, lines 63–65, of U.S. Pat. No. 4,937, 196).

Living cells or bio-catalytic subcellular components are unable to derive any benefit from gaseous oxygen. Living cells or biocatalysts derive benefit solely from oxygen dissolved within the aqueous media which surrounds the particles. In batch fermentations which are common for microbial production, the sparging of air or oxygen-enriched gases through the aqueous nutrient media is intended to replace the dissolved oxygen consumed by the metabolizing cells. In this method, most of the gas exits unused while dissolved oxygen levels are maintained at some value. Similarly, the sparging of air (or oxygen) into the nutrient media prior to its use in animal cell culture is intended to maintain a level of dissolved oxygen in the media. While the normal concentration of oxygen in water varies from about 0.2 to 0.3 mM (depending on such factors as pH and ionic strength), it is possible to increase this concentration to as much as 0.5 mM by applying approximately two atmospheres of oxygen pressure over a water solution.

To maintain adequate oxygen concentrations in fermentation media, most of the prior art has focused on increasing the contact between gas and liquid by: (1) producing a very small bubble size (a function of the sparging frit pore size); (2) using high-speed agitation to increase the rate of oxygen entrance into the liquid phase; or (3) using a gaseous overpressure of one or two atmospheres above the culture medium to increase dissolved oxygen levels. In the case of animal cell culture, the typical design of animal cell culture chambers has heretofore made it difficult to consider using overpressures greater than a fraction of an atmosphere. Thus, the most common method for increasing oxygen levels employs gas-permeable membranes or fibers in contact with flowing nutrient liquid to maintain dissolved oxygen levels. Such methods are taught, for example, by U.S. Pat. Nos. 3,968,035; 4,001,090; 4,169,010; 4,774,187; 4,837,390; 4,833,089; and 4,897,359.

There are a number of problems associated with these methods of increasing the concentration of dissolved oxygen in nutrient media. First and foremost, nearly all of these methods are unable to increase dissolved oxygen concentrations above that obtainable at atmospheric pressure due to the generally fragile nature of other components of the cell culture process. Next, methods which involve vigorous agitation of the liquid-gas mixture to effect increased rates of oxygen dissolution are not applicable to animal cells, which are quite fragile and can easily be damaged by hydraulic shear forces. Finally, those methods which do apply an increased gaseous overpressure above the culture media to increase dissolved oxygen concentrations cannot be scaled up much higher than approximately 1–2 atmospheres of overpressure before it becomes impossible to access the cell-containing liquid media for cell harvest or product isolation without destroying the cultured cells. Nevertheless, the teachings of each of the above methods warrant individual discussion.

U.S. Pat. No. 4,897,359 (issued to Oakley, et al.) discloses a method for oxygenating animal cell culture media for subsequent introduction into cell culture vessels in which an oxygenated gas, at an indeterminate pressure, is passed through a multiplicity of gas-permeable tubes surrounded by the liquid medium to be oxygenated. While the pressure of the input gas may be above atmospheric pressure, the pressure of the oxygenated exit liquid can be no more than atmospheric pressure. If the oxygenated exit liquid were above atmospheric pressure, it would result in outgassing of the liquid medium when the medium was introduced into the typical cell culture vessel. Such outgassing would also result in bubble formation within the media, which would be extremely deleterious to animal cell viability. Thus, the method of the invention of Oakley, et al. is useful only in assuring that the cell culture media possesses the maximum dissolved oxygen concentration obtainable at atmospheric pressure.

U.S. Pat. No. 4,837,390 (issued to Reneau) discloses a method of preservation of living organs (for subsequent transplant) in which hyperbaric conditions (2 to 15 bars or 29 to 218 pounds per square inch (psi)) are maintained. In the Reneau method, a living organ is placed in a chamber capable of withstanding pressure, and a perfusion liquid containing nutrients is pumped into and out of the chamber while a gaseous oxygen overpressure is also applied to the chamber. The method does not discuss cell culture or fermentation.

U.S. Pat. No. 4,833,089 (issued to Kojima, et al.) discloses a cell culture method in which a gaseous overpressure of oxygen or air is applied over a stirred liquid media in which cells are cultured. In this method, the pressure limitations of the apparatus (which includes peristaltic pumps, flexible low-pressure pump tubing, and low-pressure filter apparati) necessarily limit the method to overpressures of 0.3–0.7 kg/cm$^2$ (approximately 4.3–10 psi). Thus, the concentration of dissolved oxygen in the media used to bathe the cells is limited to values only slightly greater than that obtainable at atmospheric pressure (Col. 4, lines 15–17).

U.S. Pat. No. 4,774,187 (issued to Lehmann) discloses a method for the culture of microbial cells in which a gaseous overpressure is applied over stirred liquid media in which cells are cultured. In this method, the gaseous overpressure makes it impossible to access the interior of the culture compartment without depressurization and cell destruction. Lehman overcomes this problem by raising an overflow line from the media-containing bioreactor to a height such that the liquid pressure of this overflow line equals the gas overpressure. By establishing a siphon (originating in the elevated overflow vessel) connected to the overflow line, one may withdraw liquid or cells from the culture chamber without depressurizing the chamber. Because the typical culture medium is essentially an aqueous solution, the system pressure is limited to the height of a column of water which would balance the system pressure. Thus, for example, at a system pressure of 37 psi (gauge), a column of water approximately 50 feet in height would be required. Thus, from a practical standpoint, the Lehmann method is limited to dissolved oxygen levels obtainable at 1–2 atmospheres of overpressure.

U.S. Pat. No. 4,169,010 (issued to Marwil) discloses a method for improved oxygen utilization during the fermentation of single cell protein in which a gaseous overpressure above a stirred nutrient liquid in a bioreactor containing the growing cells is utilized to increase oxygen delivery to the growing cells. In this method, the recirculation of cell-free media (lean ferment) obtained by centrifugation of the bioreactor contents is passed back into the bioreactor through an absorber section containing a gas contacting zone. The gaseous overpressure is maintained by a gas pressure regulator device which blocks pressure release or vents the gas in response to a desired dissolved oxygen sensor setting. The patent discloses overpressures of about 0.1 to 100 atmospheres (approximately 16.2 to 1485 psi) (Col. 7, lines 28–30, of U.S. Pat. No. 4,169,010). Marwil states that a maximum desirable gaseous overpressure of 1 to 2 atmospheres is preferable.

Presumably, the reason that a maximum desirable gaseous overpressure of 1 to 2 atmospheres is preferable in the Marwil method, and would be difficult to exceed, arises from the fact that the metabolizing cells also release carbon dioxide, a metabolite which must be removed from the nutrient media by gas evolution if cell viability is to be maintained. Gas overpressures greater than 1 to 2 atmospheres utilized to increase dissolved oxygen content would necessarily result in very large dissolved carbon dioxide levels retained within the nutrient media which could not be removed until the gaseous overpressure was released. It should be noted that carbon dioxide solubility in aqueous solution is approximately an order of magnitude greater than that of oxygen. The inability to remove dissolved carbon dioxide from the media while still delivering increased oxygen to the media would cause an undesired decrease in aqueous pH. This decrease in pH is a serious problem of the method of Marwil. In addition, the method of Marwil is designed solely for the continuous harvest of cells; the method cannot be applied to the continuous harvest of the aqueous solution which might contain an excreted cellular product chemical.

U.S. Pat. No. 4,001,090 (issued to Kalina) discloses a method for microbial cell culture which incorporates a process for improved oxygen utilization which is very similar to that outlined above for Marwil (U.S. Pat. No. 4,169,010). The method of Kalina directly addresses the problem of carbon dioxide removal mentioned earlier in connection with the method of Marwil. This problem is eliminated by the inclusion of a gas-liquid separator in the fermentor circuit. In the method of Kalina, an oxygenated gas at an unspecified pressure greater than atmospheric is released into the fermentation chamber at its bottom (common sparging). However, by means of a backpressure device, the media is maintained at an overpressure of as much as 3 to 3.5 atmospheres (44.1 to 51.5 psi) to provide both a motive force for the media recirculation, as well as to aid in the removal of excess gas distal to the fermentation zone (Col. 4, lines 35–37). The Kalina process relies heavily on the presence of gas bubbles for the agitation of the media and is suitable solely for use in microbial cell fermentation. The method could not be applied to animal cell culture because animal cells are extremely sensitive to hydraulic shear forces and are damaged or destroyed by contact with air-water interfaces such as those encountered in gas bubble-containing media.

U.S. Pat. No. 3,968,035 (issued to Howe) discloses a method for the "super-oxygenation" of microbial fermentation media in which the common sparging of an oxygen-containing gas into the fermentation media is replaced by the introduction of this gas into an "oxidator" vessel in which high-shear agitation is used to reduce the average size of the gas bubbles, thus increasing the available surface area for gas-liquid contact with the result that maximal dissolved oxygen concentration is maintained. The fermentation media which has thus been treated is pumped into the fermentation reactor while exhausted media from this same source provides the input to the "oxidator" vessel. The method in Howe thus provides a combined liquid and oxygen-enriched gaseous mixture to the culture chamber; a situation which is inapplicable to animal cell culture for the previously-mentioned reasons.

Because the immobilization of cells or microorganisms requires that a cell culture chamber be part of the process system, the recent literature on cell culture chambers has been examined for comparison. There are a number of cell culture chambers in existence. Many of these chambers provide for the input and output of a liquid stream, several have viewing ports, and all provide a surface upon which cells may attach or a chamber in which suspended cells may be cultured. Such methods are taught, for example, in U.S. Pat. Nos. 3,871,961; 3,753,731; 3,865,695; 3,928,142; 4,195,131; 4,308,351; 4,546,085; 4,667,504; 4,734,372; 4,851,354; and 4,908,319. In all cases, the operating pressure of these confinement chambers is one atmosphere (or less). Thus, these chambers are unsuitable for processes in which increased dissolved oxygen levels are desired, and are necessarily limited to those dissolved oxygen levels obtainable at atmospheric pressure.

The current state of the art reveals that there are three inter-related problems which plague the economical use of mass cultures of microbes, animal cells, or their subcellular components. First, as is evident from the sheer volume of the prior art on cell immobilization, the primary problem relates to increasing the density of the cell culture. It is obvious that the economical production of a biological product will be directly related to the ability to efficiently culture large aggregates of the desired cell type. Unfortunately, the drive to increase cell culture density has lead to the evolution of the two secondary problems, the inability to adequately nutrition a high density cell aggregate, and the inability to supply adequate oxygen to high density aerobic cell populations. As cell density is increased, the only method for supplying adequate liquid nutrient to the aggregate involves increased liquid flow rates which, in all cases in the prior art, eventually limits the overall scale of the immobilization method. Similarly, as the cell density increases, the inability to deliver adequate dissolved oxygen (or any other gas) to the cell aggregate is even more of a limiting factor and severely reduces the scale of the culture.

Accordingly, there remains a need for an apparatus and method for continuously culturing, feeding, and extracting biochemical products from either microbial or eukaryotic cells or their subcellular components while maintaining viable, high density aggregates of these biocatalysts. In addition, there is a need for a method for the absolute immobilization of sample biocatalyst populations which will allow the study of various nutritive, growth, and productive parameters to provide a more accurate understanding of the inter-relationships between these parameters and their effects on cell viability and productivity.

SUMMARY OF THE INVENTION

The present invention comprises a novel culture method and apparatus in which living cells or subcellular biocatalysts are immobilized within bioreactor chambers mounted in a centrifugal field while nutrient liquids, without any gas phase(s) in contact with the liquids, are flowed into and out of the bioreactor chambers. The cells or biocatalysts are ordered into a three-dimensional array of particles, the density of which is determined by the particle size, shape, intrinsic density, and by the selection of combinations of easily controllable parameters such as liquid flow rate and angular velocity of rotation.

According to the present invention, the cells or biocatalysts can be confined within the bioreactor chambers at a defined volume. Only liquids (which may contain dissolved gases) are passed into and out of the bioreactor chambers. To cause nutrient liquids to flow through the three-dimensional array of cells or catalysts in the bioreactor chambers, positive displacement pumps are employed to move the nutrient liquid, at positive hydraulic pressure, through the bioreactor chambers. The confined cells or biocatalysts are unaffected by the resultant increase in hydraulic pressure as long as high-frequency pressure fluctuations are not present. Thus, fresh, optimal liquid nutrient media is presented to the confined cells or biocatalysts at all times during the process flow while desired cellular products are immediately accessible at the output of the bioreactor chambers.

The present invention can be used to produce high yields of industrial chemicals or pharmaceutical products from biocatalysts such as bacteria, yeasts, fungi, and eukaryotic cells or subcellular organelles, such as mitochondria, or immobilized enzyme complexes. These cells or cellular substructures can be either naturally occurring or can be genetically manipulated to produce the desired product. The present invention can be operated in either of two modes: (1) a mode in which nutrient limitation is used to ensure a defined bioreactor bed volume. This mode is applicable to cultures where desired products are released from the immobilized biocatalysts and exit the bioreactor in the liquid flow; (2) a mode in which excess nutrient input is used to cause overgrowth of the volume limitation of the bioreactor. This mode is useful for the continual production and outflow of mature cells containing an intracellular product.

Accordingly, it is an object of the present invention to provide a method and apparatus by which biocatalysts are immobilized within bioreactor chambers while nutrient liquids are fed into the bioreactor chambers and effluent liquids containing desired metabolic product(s) exit the bioreactor chambers.

It is a further object of the present invention to provide a method and apparatus by which biocatalysts, including living cell populations, may be immobilized and either aerobic or anaerobic fermentations performed in which liquid nutrient and substrate nutrients are converted to product-containing output liquid streams.

It is a further object of the present invention to provide a method and apparatus by which bacterial cell populations may be immobilized and fermentations performed in which liquid nutrient and substrate media are converted to product-containing output liquid streams.

It is a further object of the present invention to provide a method and apparatus by which fungal cell populations may be immobilized and fermentations performed in which liquid nutrient and substrate nutrients are converted to product-containing output liquid streams.

It is a further object of the present invention to provide a method and apparatus by which yeast cell populations may be immobilized and fermentations performed in which liquid nutrient and substrate nutrients are converted to product-containing output liquid streams.

It is a further object of the present invention to provide a method and apparatus by which eukaryotic animal cell populations may be immobilized and fermentations performed in which liquid nutrient and substrate nutrients are converted to product-containing output liquid streams.

It is a further object of the present invention to provide a method and apparatus by which either prokaryotic or eukaryotic plant cell populations may be immobilized and fermentations performed in which liquid nutrient and substrate nutrients are converted to product-containing output liquid streams.

It is a further object of the present invention to provide a method and apparatus by which enzymes or enzyme systems immobilized on solid supports or catalysts immobilized on solid supports or cells or cell components immobilized on solid supports may be immobilized and catalyzed chemical conversions be effected in which liquid substrate nutrients are converted to product-containing output liquid streams.

Another object of the present invention is to provide a method and apparatus by which dissolved oxygen concentrations (or other dissolved gases) in the nutrient liquid flow directed into a bioreactor chamber may be raised to any desired level, depending on the applied hydraulic pressure.

Another object of the present invention is to provide a method and apparatus by which either a nutrient gaseous substrate (such as oxygen) in the nutrient input liquid flow directed into a bioreactor chamber or an excreted respiratory gas (such as, for example, carbon dioxide) in the output liquid flow may be maintained in the dissolved state until liquid-gas disengagement is desired, generally far downstream of the bioreactor chamber(s).

Another object of the present invention is to provide a method and apparatus by which the conversion of an available chemical substrate into a desired product may be effected by a series of stepwise biocatalyst-mediated conversions in which each chemical conversion step is effected by one of a series of bioreactor chambers inserted serially or in parallel into the flow stream.

Another object of the present invention is to provide a non-specific, general method and apparatus for cell culture or fermentation which can be applied to any cell type without significant variation.

It is yet another object of the present invention to provide a method and apparatus by which biocatalysts are immobilized within bioreactor chambers while media containing toxic chemicals are fed into the bioreactor chambers and the biocatalysts in the bioreactor chambers neutralize the toxic chemicals thereby converting them into an environmentally benign products.

Another object of the present invention is to provide a method and apparatus for cell culture or fermentation which significantly reduces both the capital and labor costs of production and production facilities.

Another object of the present invention is to provide a method and apparatus for cell culture or fermentation which is much less susceptible to contamination by opportunistic organisms.

Another object of the present invention is to provide a method and apparatus for cell culture or fermentation in which the liquid environment bathing the desired biocatalyst is essentially invariant in time, i.e., the pH, ionic strength, nutrient concentrations, waste concentrations, or temperature do not vary as a function of time in the biocatalyst's environment.

Another object of the present invention is to provide a continuous fermentative or cell culture method.

Another object of the present invention is to provide a method and apparatus for cell culture or fermentation in which cycles of proliferation, growth, or product formation can be accomplished simply by varying the input nutrient feed composition.

Another object of the present invention is to provide a method and apparatus for cell culture or fermentation which can continue for the lifetime(s) of the immobilized micro-organism or cell type.

Another object of the present invention is to provide a method and apparatus for culturing biocatalysts under conditions which thereby significantly increases the yield of products from the biocatalyst.

Another object of the present invention is to provide a method and apparatus for cell culture or fermentation which increases the conversion efficiency (of substrate to product) of the culture process.

Another object of the present invention is to provide a method and apparatus for cell culture or fermentation which significantly reduces the cost of heating or cooling the aqueous media required to support the culture process.

Another object of the present invention is to provide a method and apparatus for cell culture or fermentation which results in higher yields of products such as antibiotics from micro-organism fermentations.

Another object of the present invention is to provide a method and apparatus for cell culture or fermentation which results in higher yields of products such as enzymes or other proteins from micro-organism fermentations.

Another object of the present invention is to provide a method and apparatus for cell culture or fermentation which results in higher yields of products such as ethanol or other short-chain alcohols and acids from the fermentation of micro-organisms.

Another object of the present invention is to provide a method and apparatus for cell culture or fermentation which results in higher yields of products such as protein hormones from genetically-transformed micro-organisms.

Another object of the present invention is to provide a method and apparatus for cell culture or fermentation which results in higher yields of products such as protein hormones from eukaryotic cells.

Another object of the present invention is to provide a method and apparatus for cell culture or fermentation which results in higher yields of products such as amino acids, nitrogenous bases, or alkaloids from the fermentation of micro-organisms.

Another object of the present invention is to provide a method and apparatus for cell culture or fermentation which results in higher yields of products such as fuel-grade ethanol from the fermentation by yeasts of sugar-containing agricultural material.

Another object of the present invention is to provide a method and apparatus which would reduce the fermentation time required to produce alcoholic beverages such as beer and wine.

Another object of the present invention is to provide an easily scaled-up method and apparatus for cell culture or fermentation which can be commercially employed.

These and other objects, features and advantages of the present invention will become apparent after a review of the following detailed description of the disclosed embodiment and the appended claims.

BRIEF DESCRIPTION OF THE FIGURES

The accompanying figures, which are incorporated and form a part of the specification, illustrate several scientific principles and embodiments of the present invention and, together with the description, serve to explain the principles of the invention.

FIG. 37 is a graphical and mathematical representation of the portion of the biocatalyst immobilization chamber of FIGS. 21 and 33 which resembles a truncated cone.

DETAILED DESCRIPTION OF THE INVENTION

The development of this immobilization and culture process has its origin in four distinct areas of knowledge. The function of the overall process depends on the use of information from all four areas for its proper function. These areas are: (1) Stoke's Law and the theory of counterflow centrifugation; (2) the geometrical relationships of flow velocity and centrifugal field strength; (3) Henry's Law of Gases; and, (4) the effect of hydraulic pressure on single and multicellular organisms and their cellular or subcellular components.

The central purpose of the process of this invention is immobilization of three-dimensional arrays of particles (cells, subcellular structures, or aggregated biocatalysts) and to provide them with a liquid environment containing dissolved gases which will maximize their viability and productivity. Such cells may include, but are not limited to, a prokaryotic cell, a bacterium, or a eukaryotic cell, such as algae cells, plant cells, yeast cells, fungal cells, insect cells, reptile cells and mammalian cells. The biocatalyst may be, but is not limited to, a subcellular component, an enzyme complex, and/or an enzyme complex immobilized on a solid support.

The dissolved gases of the present invention include but are not limited to air, $O_2$, $NH_3$, $NO_2$, Ar, He, $N_2$ and $H_2$ or any mixture thereof.

Figure 3:
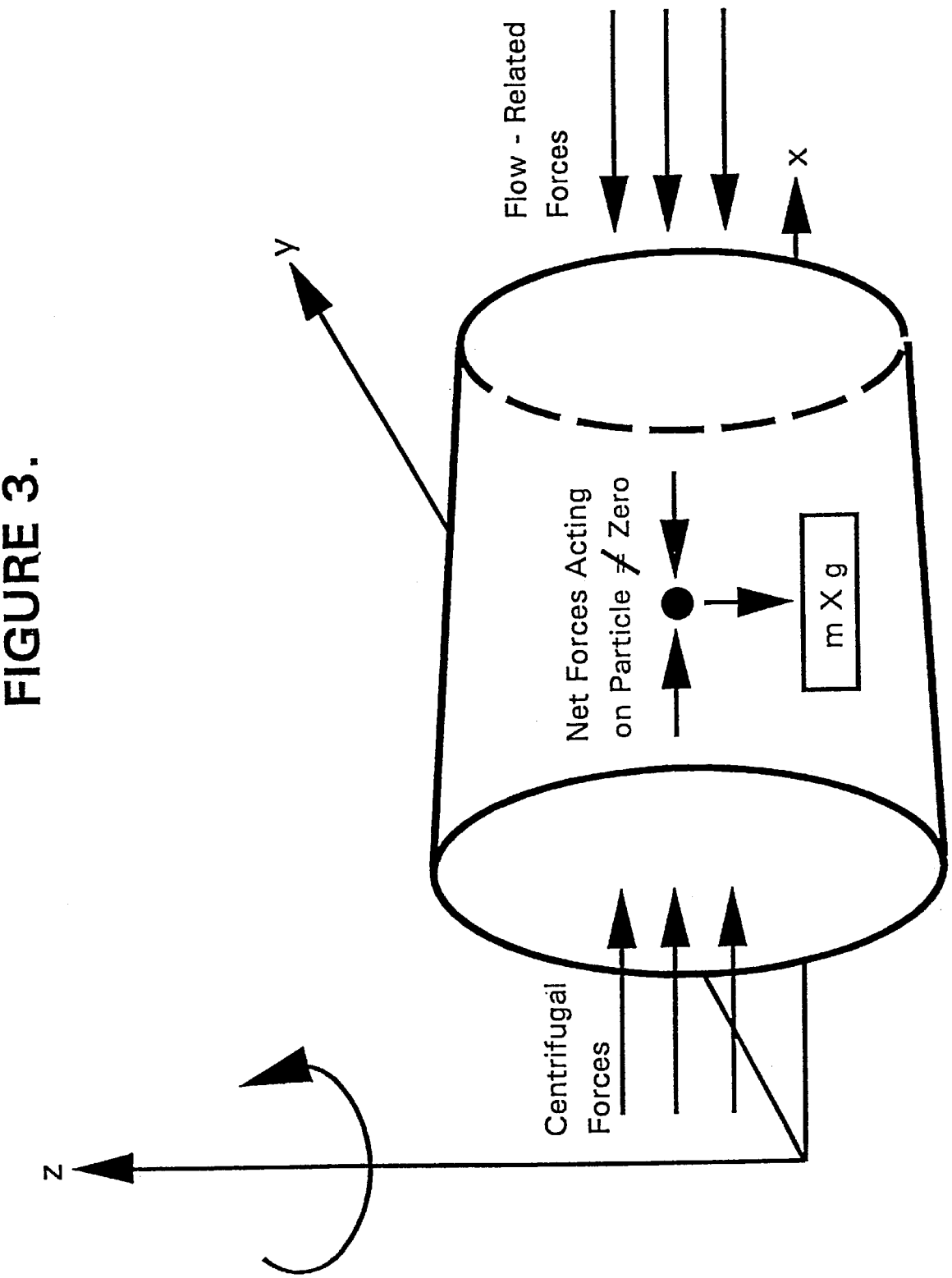
FIG. 3 illustrates the central problem with Counter-Flow Centrifugation.
Figure 4:
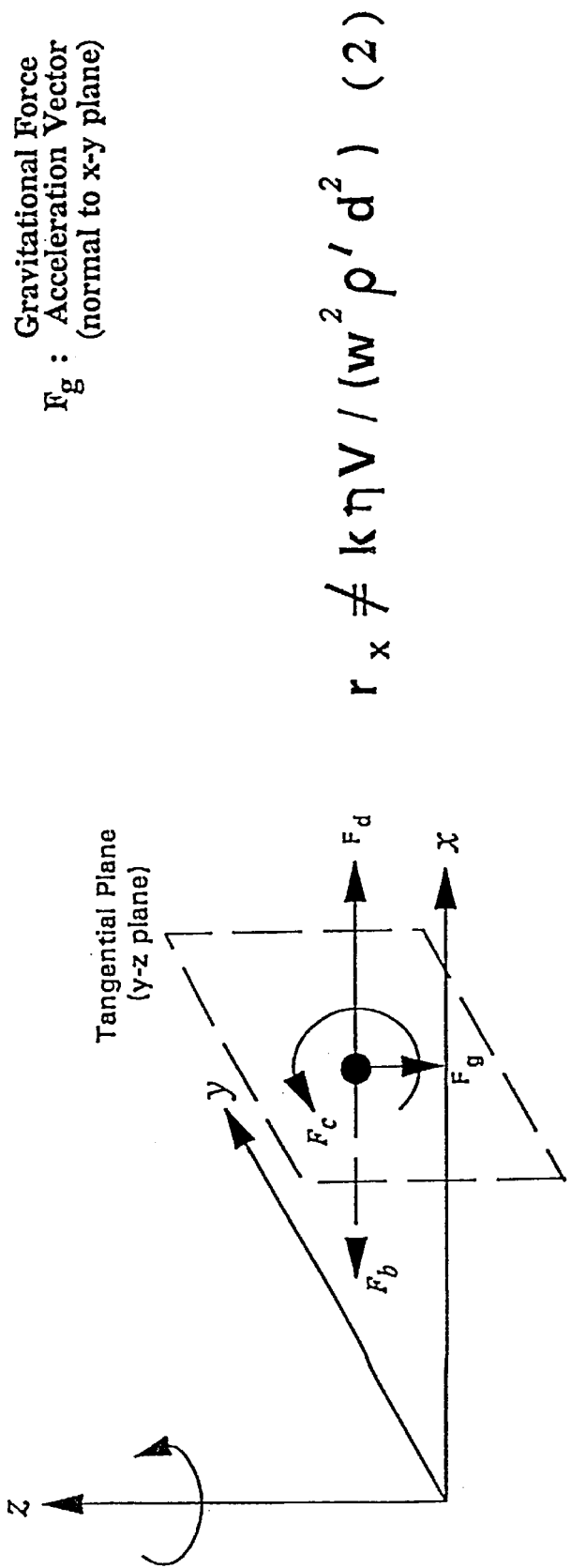
FIG. 4 illustrates the mathematical defect in the conventional treatment of Counter-Flow Centrifugation.
Figure 5:
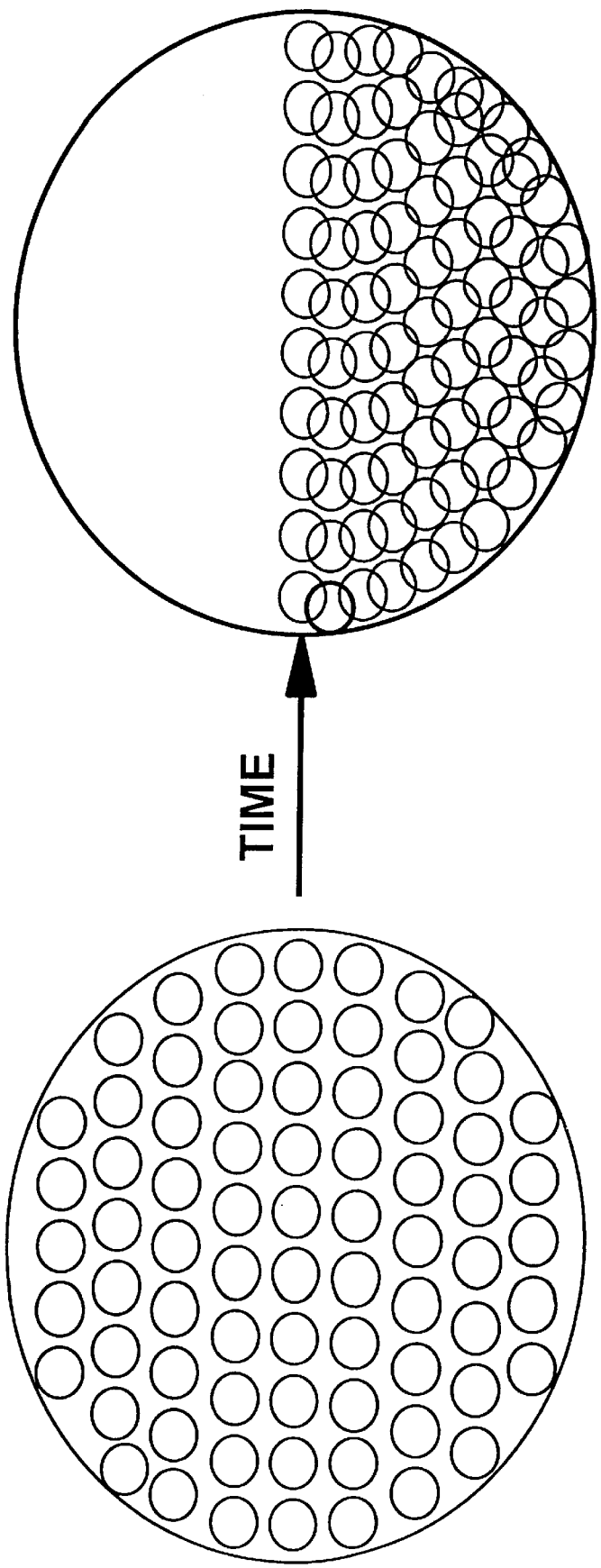
FIG. 5 is an illustration of the effect on immobilized particles using conventional Counter-Flow Centrifugation at long time periods.
Figure 6:
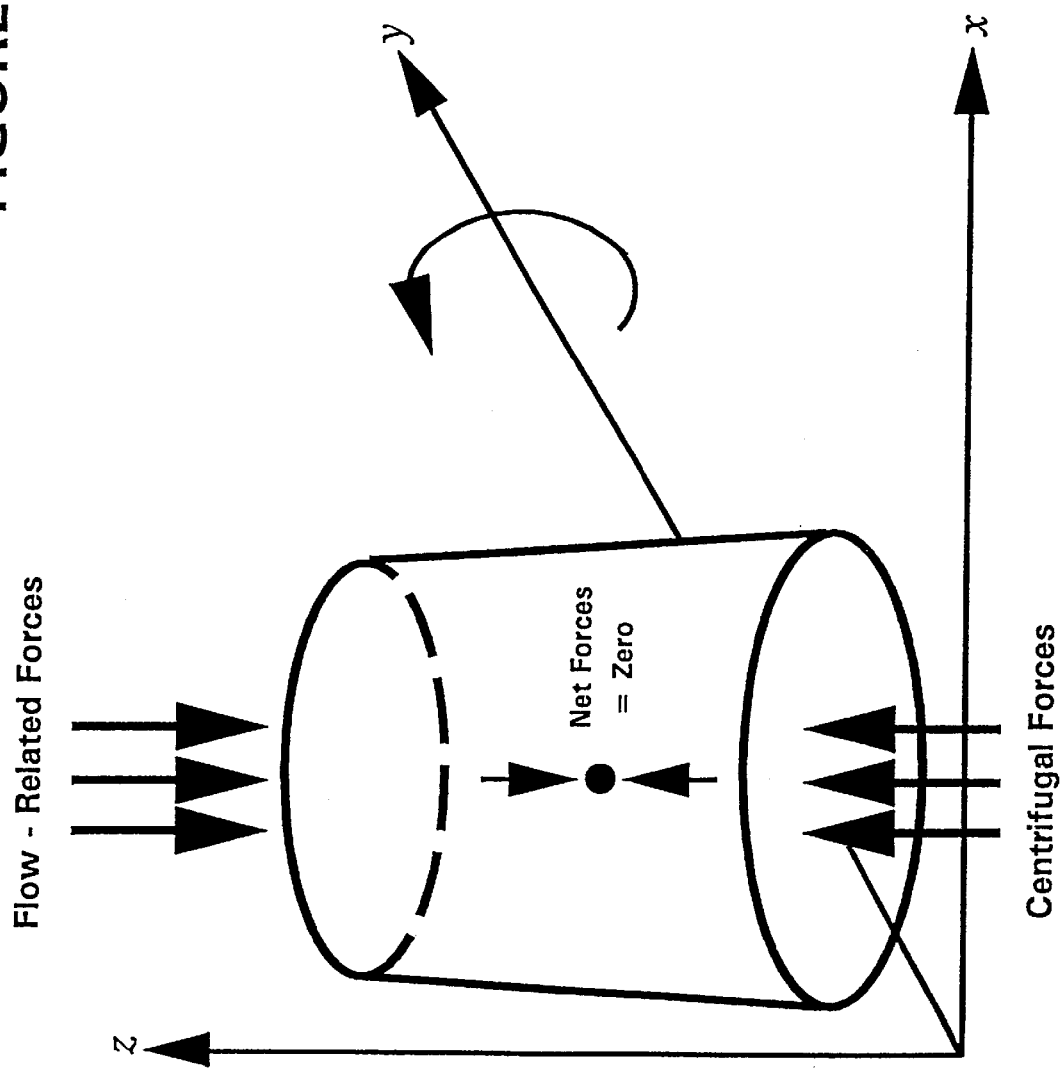
FIG. 6 illustrates the modification of Counter-Flow Centrifugation employed in the process of this invention.

This process utilizes a novel modified form of "Counterflow Centrifugation" to immobilize particle arrays. A proper application of Stoke's Law in combination with provision for the effect of gravity which also acts on the immobilized particles results in a mathematical relationship which allows for the relative immobilization of high-density arrays of such particles. The effect of gravity discussed previously and graphically depicted in FIGS. 3–5 can be eliminated by an alternative choice of rotational axis as is shown in FIG. 6. If rotation about the horizontal axis (y) is chosen instead of rotation about the vertical axis (z), as is most common in biological centrifugations, then the effect of gravity on immobilized particles will always be limited to action solely in the x-z plane. Since this is the same plane in which both the centrifugal as well as the liquid flow related forces are constrained to act, the motion of a restrained particle at any point in a rotational cycle is the resultant of the sum of the three types of forces acting upon it.

Figure 7:
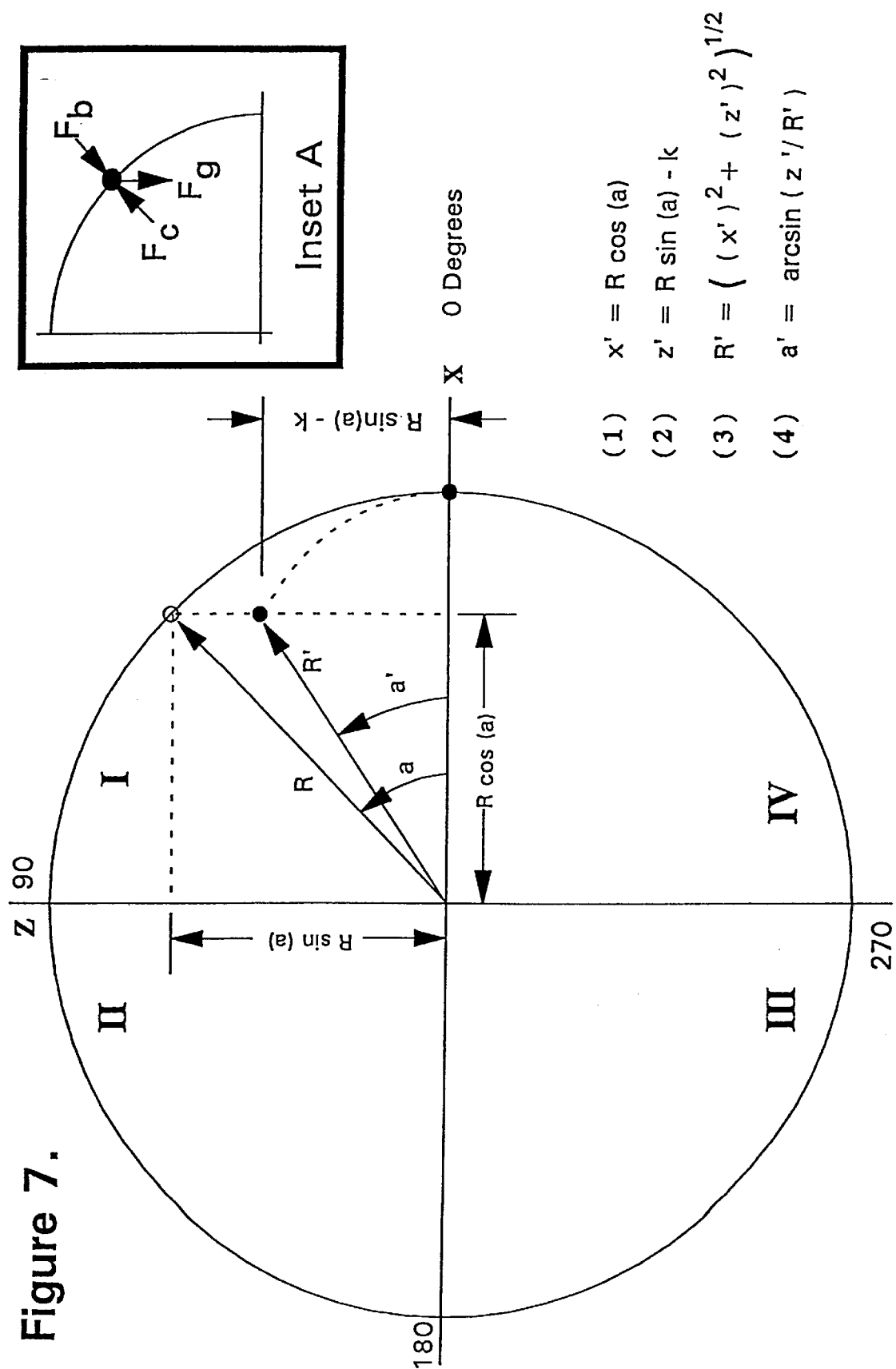
FIG. 7 is an illustration of the mathematics governing the motion of a particle due to the effect of gravity on that particle when it is restrained in a centrifugal field exactly opposed by a liquid flow.

As is shown in Inset A of FIG. 7, where the plane of the Figure is the x-z plane, the effect of gravity ($F_g$) on the position of a particle suspended in a radially-directed centrifugal field ($F_c$) while an exactly equal and opposing force supplied by an inwardly-directed flowing liquid ($F_b$) is directed toward the particle, can be calculated by the evaluation of equations 1–4 where (k) represents the downward displacement in the x-z plane imparted by gravitational forces during an angular rotation of the rotor position equal to (a). Analysis of the motion of a particle under these constraints and for $[2\_X (k/a)] < R$ (a low mass particle) results in the determination that the motion is periodic; that is, the particle motion results in a return to its starting place after a complete rotation of 360 degrees (after equilibrium is reached). As is shown in FIG. 7, the effect of gravity on the motion of a particle otherwise immobile as a result of the opposing equality of the centrifugal and flow-related forces results in a decrease in radial position in quadrants I and II, and an exactly equal radial lengthening in quadrants III and IV. Thus, the radial distance of the particle from the axis of rotation also exhibits a periodic motion over the course of a full rotation of 360 degrees. It should be noted that, mathematically, measurement of the periodicity of motion requires only one rotation if measurement begins at either 90 or 180 degrees whereas two full rotations are required if measurement begins at either zero or 180 degrees, since a new equilibrium radial distance different from the original results in the latter case.

Figure 8:
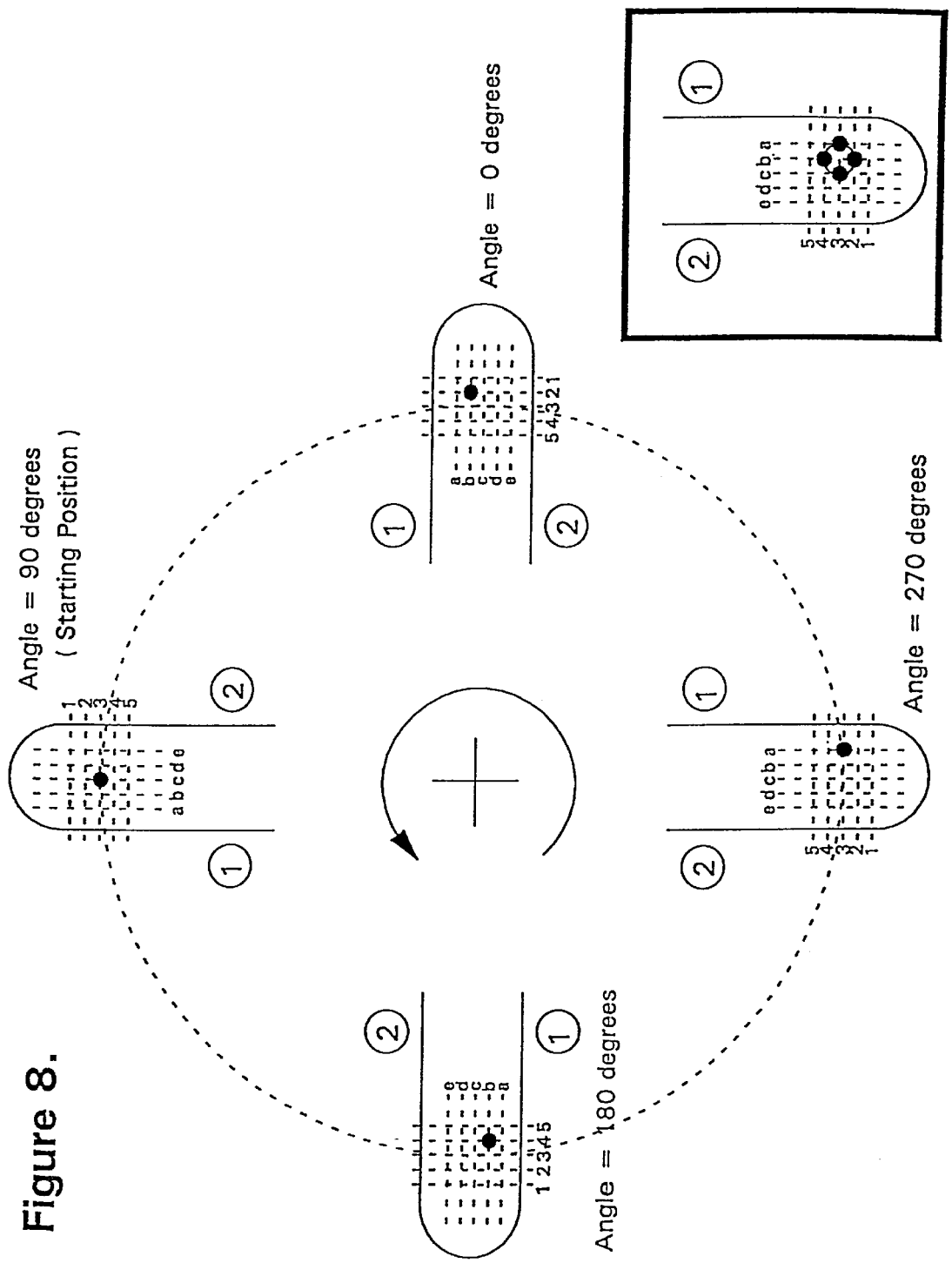
FIG. 8 is an illustration of the resultant motion of a particle under the constraints of FIG. 7.

The effective motion of a particle through a complete rotational cycle is shown in the inset of FIG. 8. If the sides of a container in which the particle is suspended are labeled 1 and 2 (see circled numbers in FIG. 8), then the motion of the particle over the course of one rotational cycle would describe a circle with its center displaced toward the "leading edge" side of the particle's container. Thus, a particle suspended in a centrifugal field which is opposed by an equal liquid flow field will be constrained to periodic motion (and thus is effectively immobilized) if the balance of the radially-directed forces can be maintained over the course of its movement.

Figure 1:
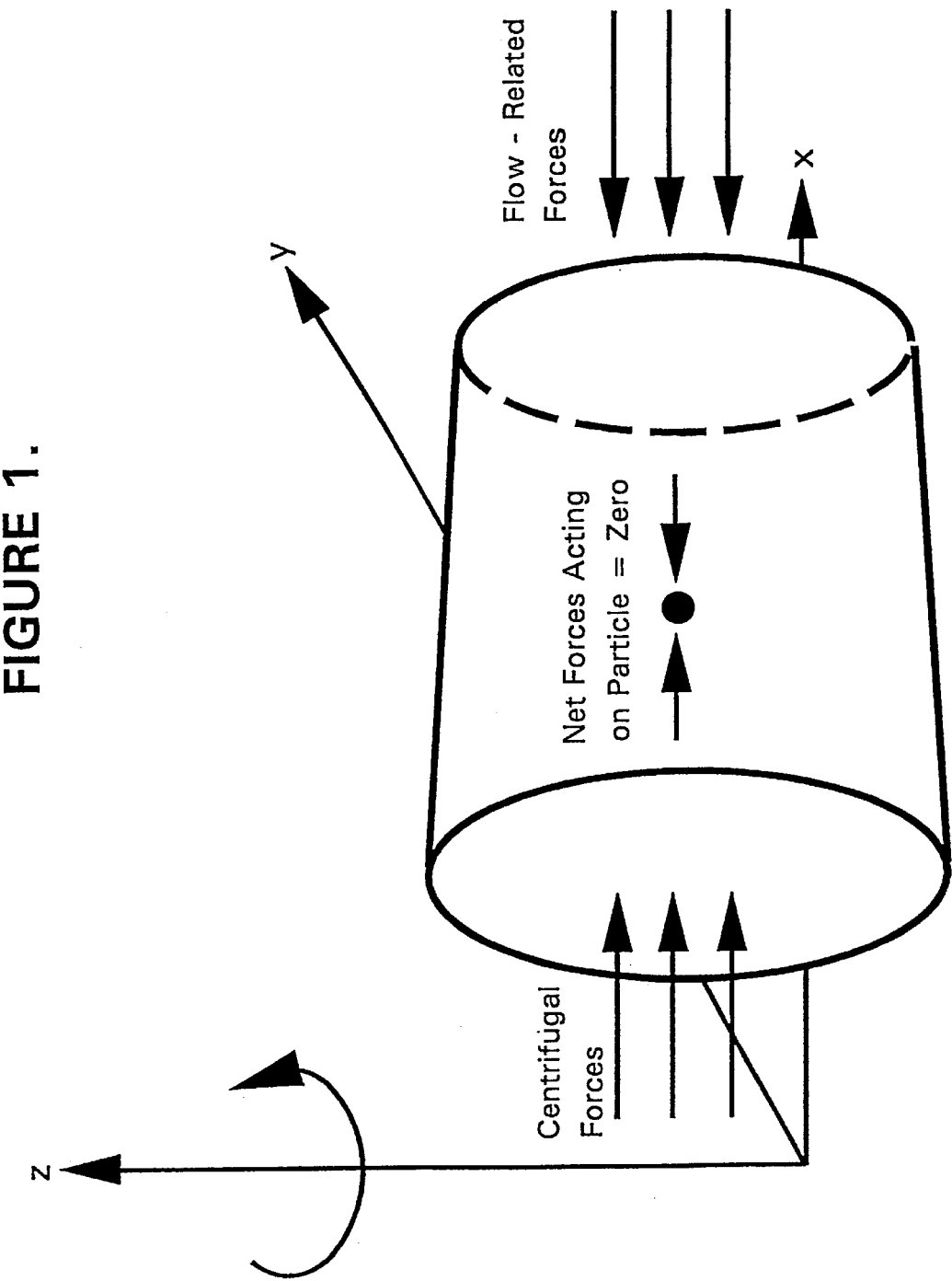
FIG. 1 illustrates the central features of Counter-Flow Centrifugation.
Figure 2:
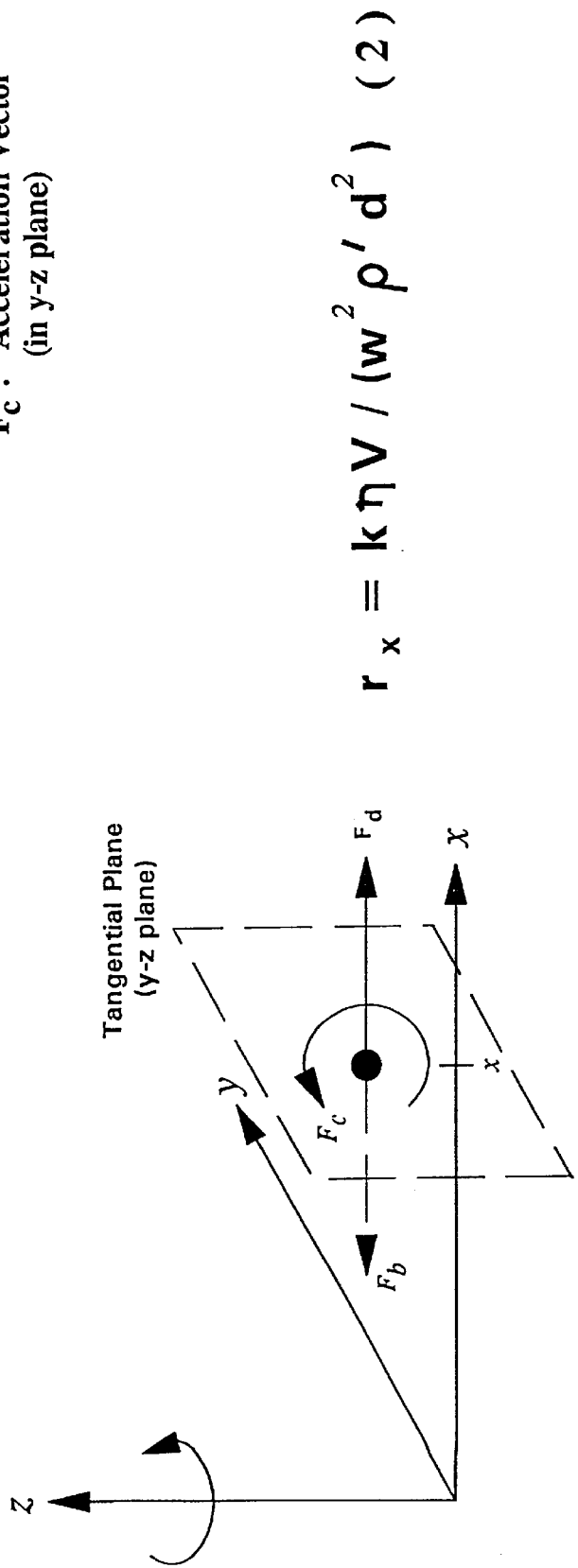
FIG. 2 illustrates an analysis of the operative forces in Counter-Flow Centrifugation.
Figure 9:
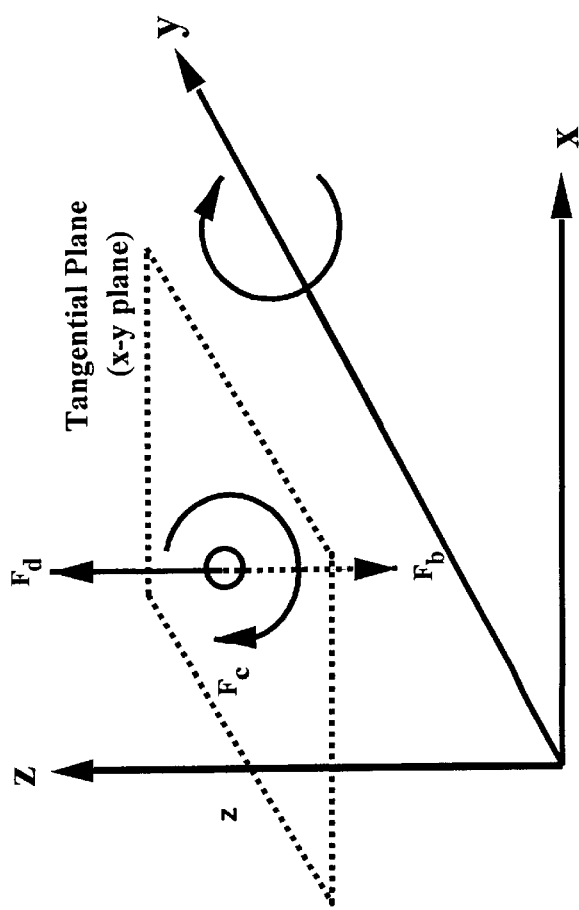
FIG. 9 is a mathematical evaluation of the immobilization conditions at a given radius.

With these theoretical considerations in mind, we can now return to the hypotheses of Sanderson and Bird which were graphically shown in FIG. 2. A corrected graphical representation is shown in FIG. 9, in which the axis of rotation is now the (y) axis. Under these conditions the hypothesis of Sanderson and Bird can now be restated and applied to long-term immobilization of particles. Equation 3 of FIG. 9 is now valid. There is a radial distance along the z axis ($r_z$) which, when evaluated by Eqn. 3, represents a position in which the particle is relatively immobilized in a centrifugal field which is exactly opposed by an inwardly-directed liquid flow, even in the presence of a gravitational field. Furthermore, a simplification of Stoke's Law (Eqn. 1) under the conditions of uniform particle size, shape, and density and a homogeneous liquid flow results in Eqn. 2, where it is obvious that the Sedimentation Velocity of a particle (SV) is a simple linear function of the applied centrifugal field. Similarly, Eqn. 3 can then be rewritten under the same conditions to yield Eqn. 4, where liquid Velocity (V in Eqn. 3) has been replaced by liquid Flow Velocity (FV). Equation 4 suggests that there is a continuum of liquid flow velocities and applied centrifugal fields which could be matched by the evaluation of constant (C), all of which would satisfy the requirement of relative particle immobilization. Further, if the liquid flow velocity could be varied as a function of (z), there could be a separate application of this equation at each radial distance. Consideration of the implications of Eqn. 4 is important for the relative immobilization of three-dimensional arrays of particles as opposed to the immobilization of two-dimensional arrays of particles at a single radial distance from the rotational axis.

Figure 10:
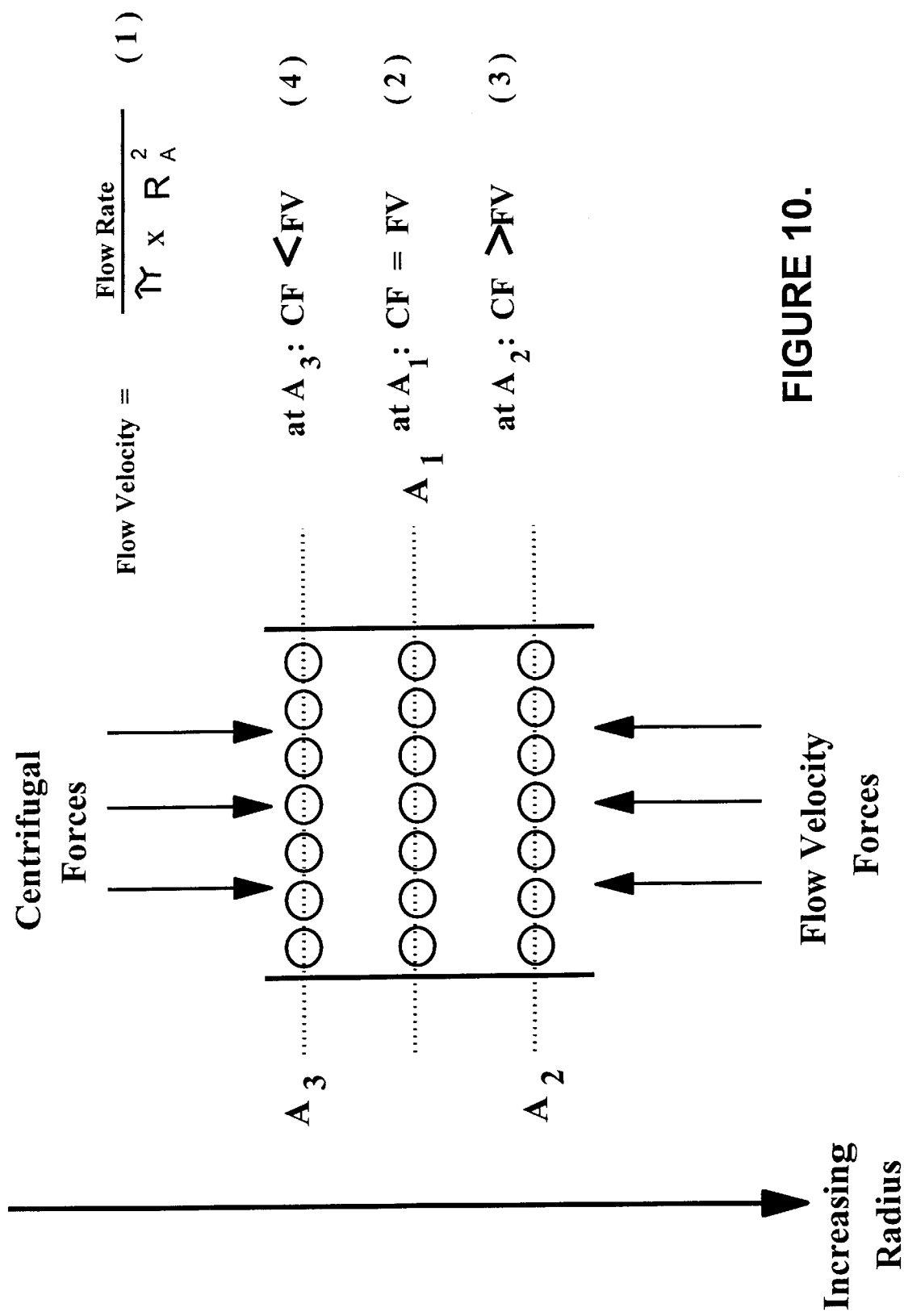
FIG. 10 is an analysis of the balance of centrifugal forces and flow velocity forces in a rotating cylindrical bioreactor chamber.

If the biocatalyst immobilization chamber in which a particle is located is cylindrical (as is graphically depicted in FIG. 10) and if a liquid is flowed into this chamber from the end of the chamber most distal to the axis of rotation, then it is obvious that the flow velocity of this liquid flow (as defined in Eqn. 1, FIG. 10) will have a single value at all points not occupied by layers of particles. As a consequence, if a two-dimensional array of particles is in positional equilibrium at a particular radial distance ($A_1$), as is indicated in Eqn. 2, (where CF is the centrifugal field strength and FV is the liquid flow velocity) then particles forced to occupy positions at radial distances either greater than or smaller than $A_1$, such as those located in FIG. 10 at $A_2$ or $A_3$, will necessarily be presented with an inequality of restraining forces which will result in net translation of the particles. Thus, those particles located at $A_2$, a longer radial distance than $A_1$, will experience a greater centrifugal force than those at $A_1$ and will necessarily migrate to longer radial distances (Eqn. 3). Conversely, particles initially located at $A_3$ would experience a reduced centrifugal field and would migrate to shorter radial distances (Eqn. 4). Thus, it is not possible to form a three-dimensional array of particles in a "parallel-walled" biocatalyst immobilization chamber such as that of FIG. 10.

Figure 11:
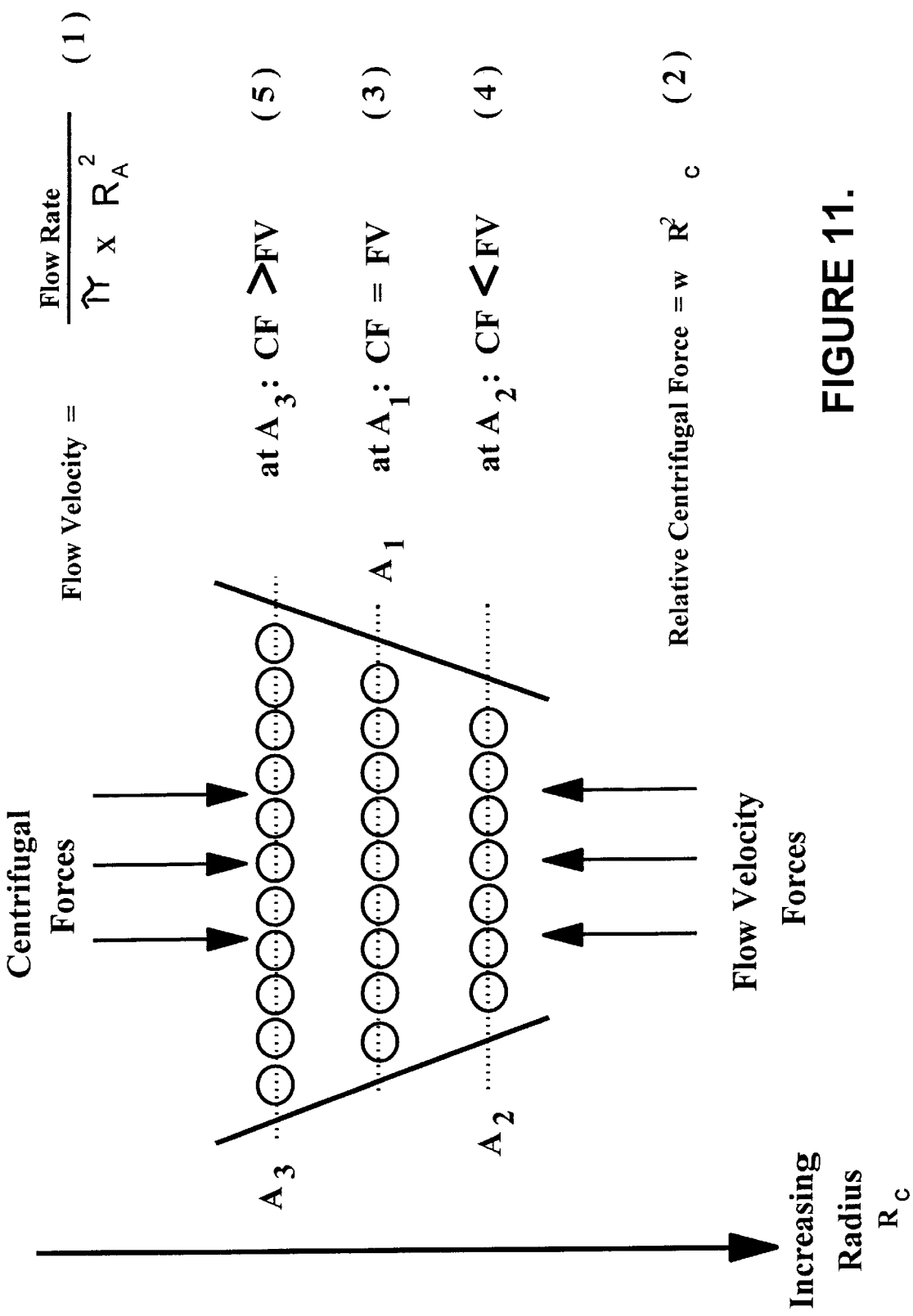
FIG. 11 is an analysis of the balance of centrifugal forces and flow velocity forces in a rotating conical biocatalyst immobilization chamber.
Figure 12:
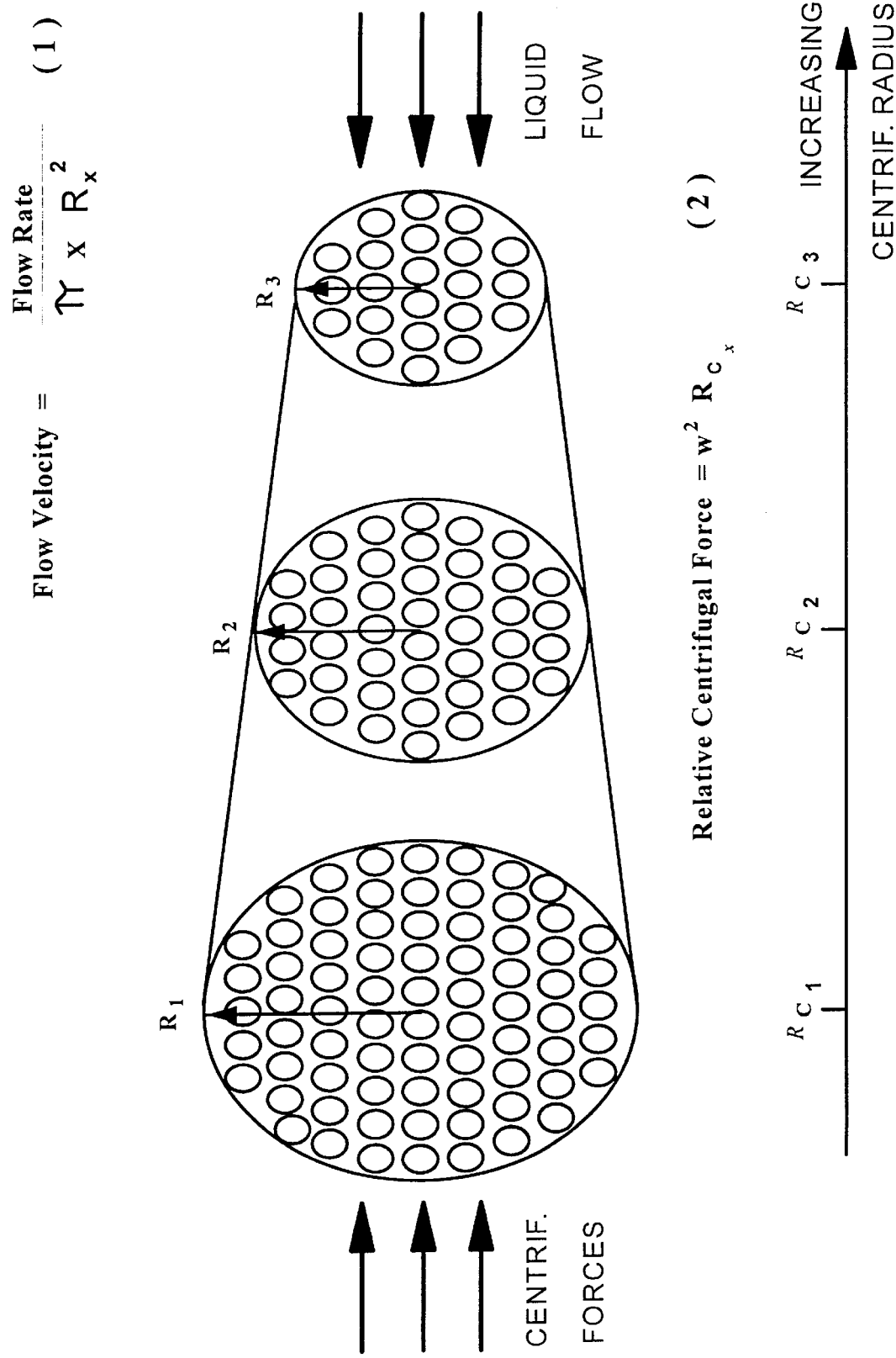
FIG. 12 is an illustration of a three-dimensional array of particles in a rotating conical biocatalyst immobilization chamber.

If, however, the biocatalyst immobilization chamber has a geometry such that its cross-sectional area increases as the rotational radius decreases, as is graphically displayed in FIG. 11, then it is mathematically possible to form three-dimensional arrays of immobilized particles. This is a consequence of the fact that the microscopic flow velocity of the liquid flow varies inversely as the cross-sectional area (Eqn. 1) while the relative centrifugal field varies directly as the rotational radius (Eqn. 2). Thus, if values of flow velocity and rotation velocity are chosen such that a two-dimensional array of particles is immobilized at rotational radius $A_1$ (Eqn. 3), then it is mathematically possible to adjust the "aspect ratio" of the side walls of the biocatalyst immobilization chamber such that those particles initially located at radial distance $A_2$ could also experience either an similar equality of forces or, as is shown in Eqn. 4, an inequality of forces which results in net motion back toward the center of the chamber. A similar argument may be applied to particles located at $A_3$ (see Eqn. 5). Although the geometry of the biocatalyst immobilization chamber as depicted in FIG. 11 is that of a truncated cone, note that other geometries could be alternatively used—subject to the constraint that the cross-sectional area of the chamber increases as the rotational radius decreases. Thus, as is depicted in FIG. 12, it is possible to construct a three-dimensional array of particles in a varying centrifugal field opposed by a liquid flow field if the biocatalyst immobilization chamber geometry chosen allows for a flow velocity decrease greater than or equal to the centrifugal field strength decrease as the rotational radius decreases. In the geometry chosen in FIG. 12, that of a truncated cone, the two-dimensional arrays of particles at each rotational radius ($R_c$) will each be constrained to motion toward that radius where the opposing forces are exactly equal.

Figure 13:
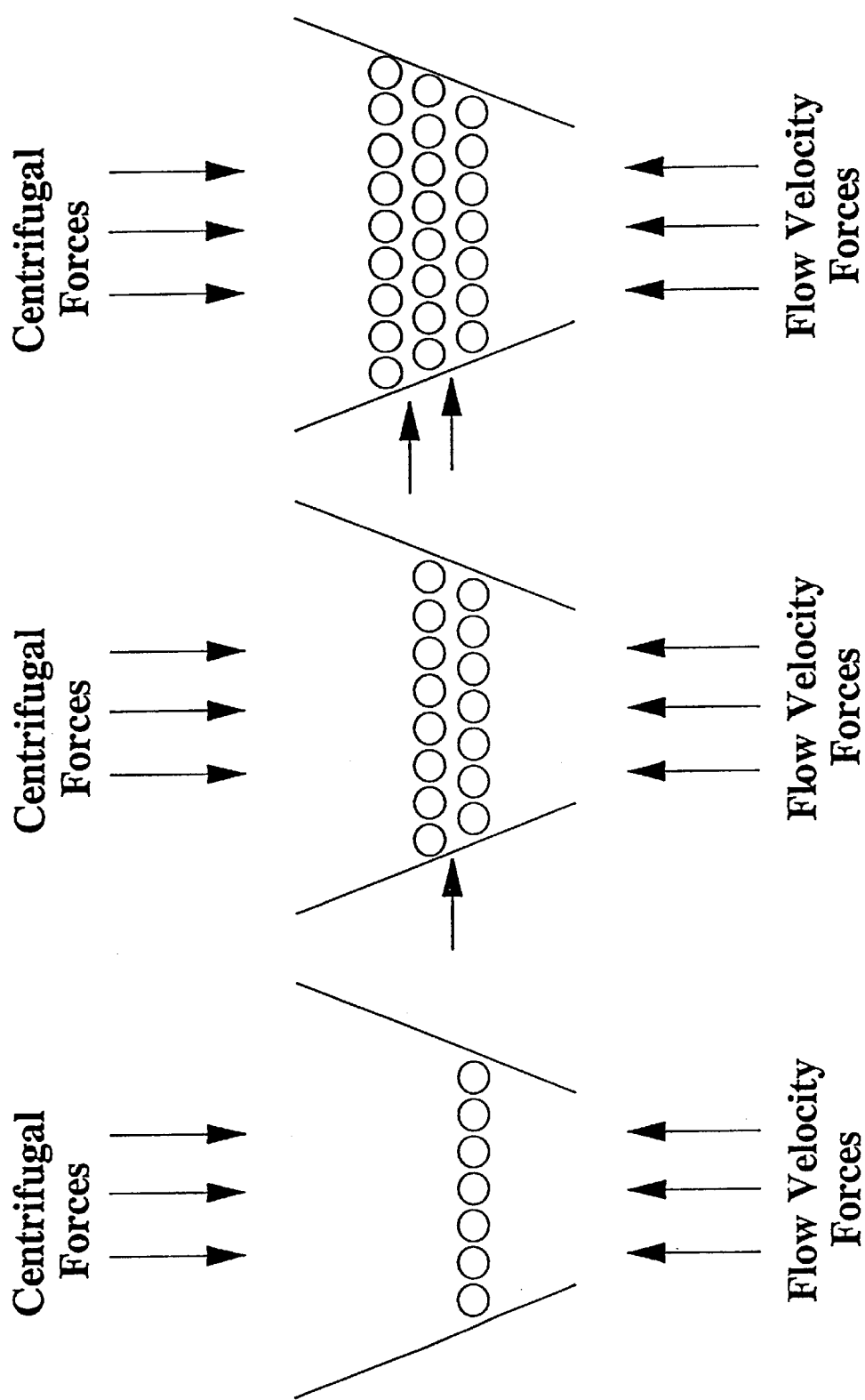
FIG. 13 is an illustration of the inter-stratum "buffer regions" in a three-dimensional array of particles in a rotating conical biocatalyst immobilization chamber.
Figure 14:
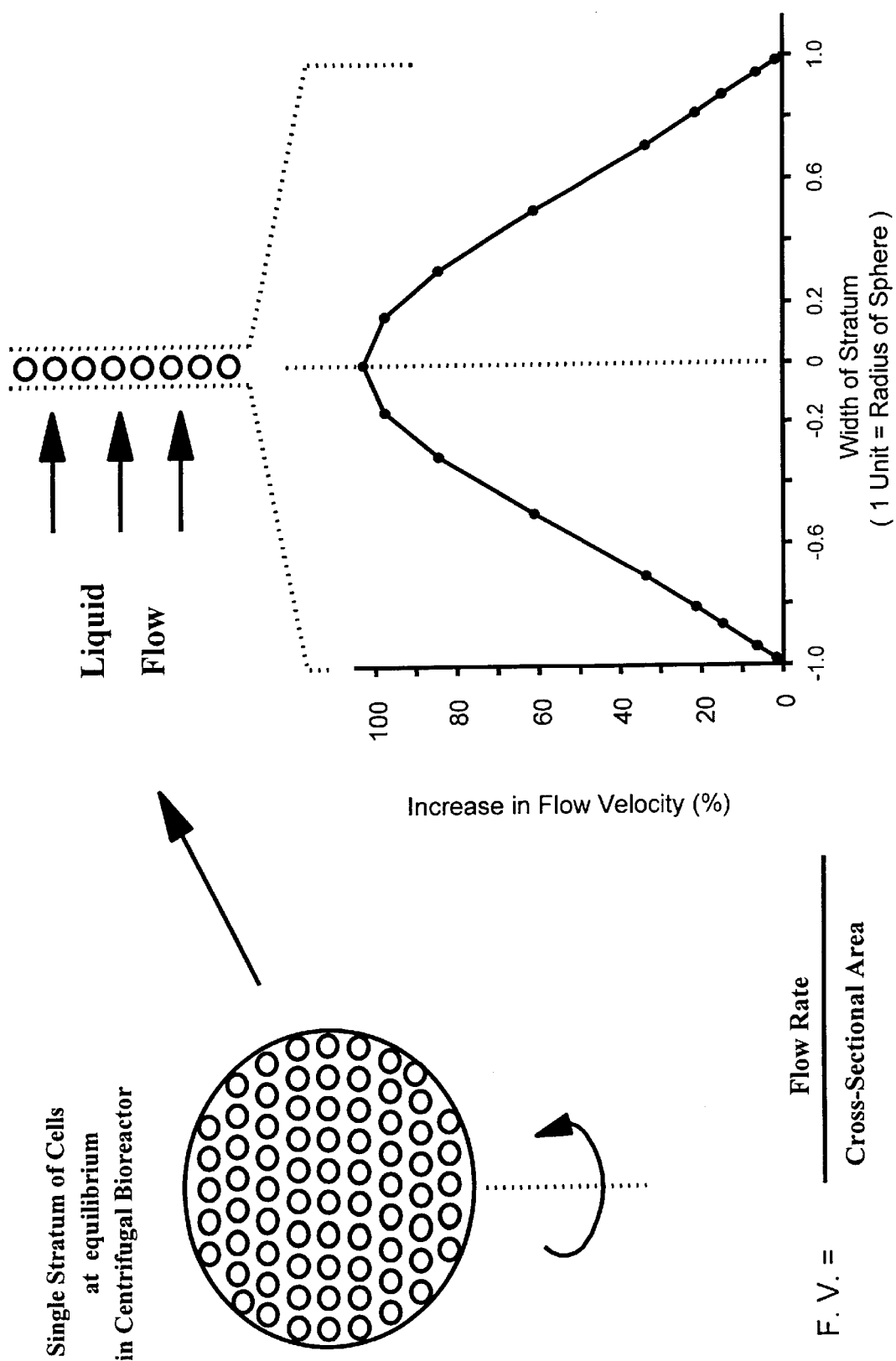
FIG. 14 is a mathematical analysis of the intra-stratum flow velocity variation in a two-dimensional array of particles in a rotating conical biocatalyst immobilization chamber.

While, at first glance, the description presented above would suggest that the net effect of the mismatch of forces at all radii other than that which provides immobilization would result in a "cramming" of all particles into a narrow zone centered on the appropriate radius, such is not the case. As is shown graphically in FIG. 13, as each layer of particles approaches an adjacent layer, it will move into a region where a "cushioning effect" will keep each layer apart (the horizontal arrows in FIG. 13). The explanation for the inability of adjacent layers of particles to interdigitate is a consequence of an analysis of the microscopic flow velocity profile through each layer. In FIG. 14, a single representative stratum of spherical particles confined to a particular radial distance in a chamber layer of circular cross-section is presented. The ratio of the diameters of the particles to the diameter of the cross-section of FIG. 14 is 12:1. While the magnitude of the flow velocity of the liquid through unoccupied portions of the chamber cross-section can be quantified simply from the chamber dimensions at that point, the flow velocity through a region occupied by a stratum of particles will necessarily be much greater than that in the absence of a stratum of particles because of the greatly reduced cross-sectional area through which the liquid must travel. As is shown in the graph in FIG. 14, the increase in flow velocity through a stratum of the above dimensions is more than double that determined in the free space just adjacent to the stratum on each side. This microscopic increase in local flow velocity in the region of each stratum effectively provides a "cushion" which keeps each adjacent stratum separate.

Figure 15:
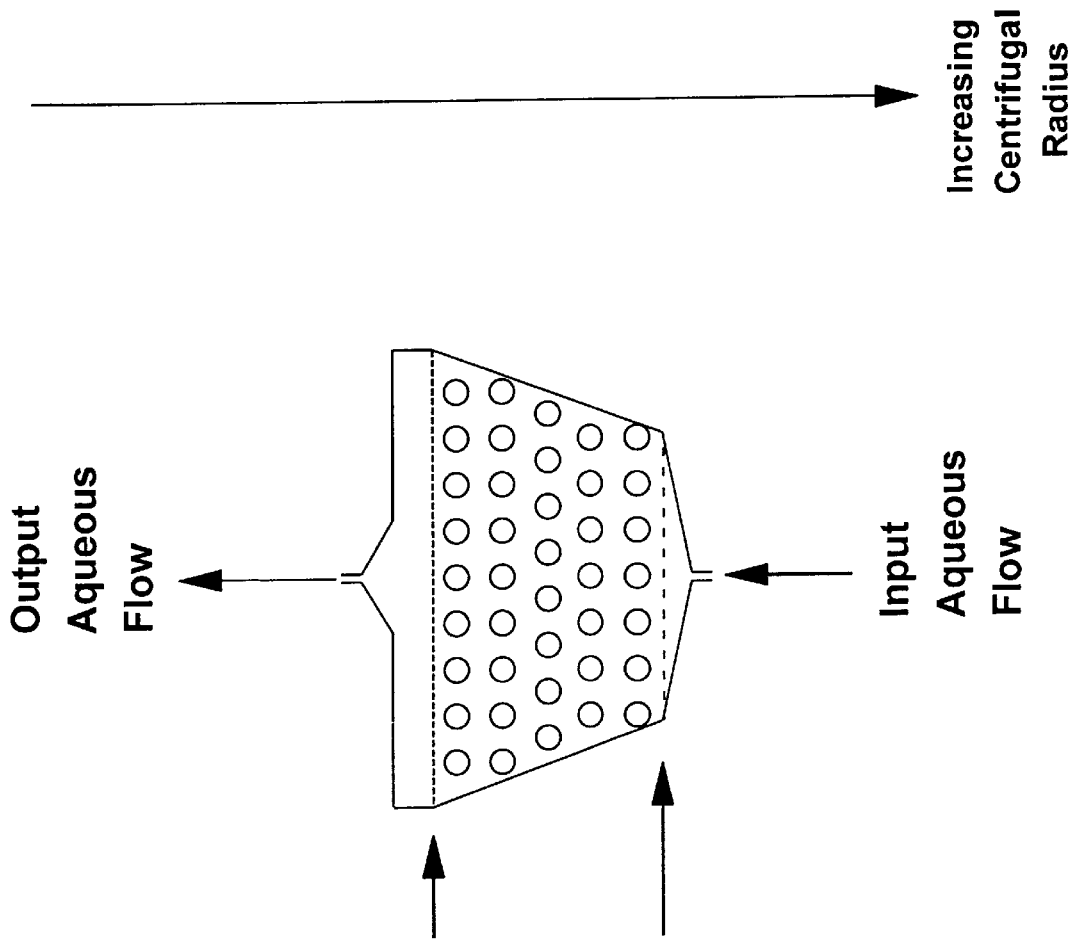
FIG. 15 is an illustration of an example conical biocatalyst immobilization chamber and the boundary conditions which determine those dimensions.

In actual use, it has been determined that, for the case of a chamber geometry of a truncated cone, it is preferable that the most distal region of the truncated cone be the region where an exact equality of centrifugal forces and liquid flow velocity is achieved. The "aspect ratio" (the ratio of the small radius of the truncated cone to the large radius of the truncated cone) of the truncated cone is determined by the simultaneous solution of the two equations presented in FIG. 15. In Eqn. 2, the desired boundary condition of immobility for that "lowest" stratum of particles is presented. It states that the intrinsic sedimentation rate of the particle due to gravity (SR) times the relative centrifugal field applied at that radial distance (RCF) be exactly equal to the magnitude of the liquid flow velocity (FV) at that point. In Eqn. 1, a desired boundary condition at the opposite surface of the array of particles is presented. In order to insure retention of all particles within the biocatalyst immobilization chamber, a boundary condition wherein the product of SR and RCF is twice the magnitude of the flow velocity at that radial distance has been arbitrarily chosen. Simultaneous solution of the desired boundary condition equations is used to solve for the ratio of the conic section diameters when the upper diameter and conic length is known.

FIG. 16 is a profile of the relative magnitudes of the flow-related forces and the centrifugal forces across a biocatalyst immobilization chamber of conical cross-section which has dimensions in this example of: large diameter=6.0 cm, small diameter=3.67 cm, and depth=3.0 cm. We define the Relative Sedimentation Rate as the product of the intrinsic sedimentation rate of a particle due to gravity in a nutrient media at its optimal temperature and the applied centrifugal field. For a given flow rate (in this example 10 mL/min) into a biocatalyst immobilization chamber of the indicated dimensions, where the proximal end of the biocatalyst immobilization chamber is 9.0 cm from the rotational axis, the product of the intrinsic particle sedimentation rate due to gravity and the angular velocity is a constant at the given flow rate in order to satisfy the desired boundary conditions (see FIG. 15). In other words, the angular velocity need not be specified here since its value depends only on the particular particle type to be immobilized. The dotted line in FIG. 16 displays the linear variation in the centrifugal field strength from the bottom to the top of the biocatalyst immobilization chamber, while the solid line displays the corresponding value of the flow velocity. At the bottom of the chamber (the most distal portion of the chamber), the forces are equal and a particle at this position would experience no net force. At the top of the chamber, a particle would experience a flow-related force which is only one-half of the magnitude of the centrifugal field and would thus be unlikely to exit the chamber, even in the presence of a nearby region of decreasing cross-sectional area (the chamber liquid exit port), where flow velocities will increase markedly.

It should be clear from the foregoing that, subject to the necessary condition that the cross-sectional area increases as rotational radius decreases, there are other geometrical chamber configurations whose shape could be manipulated in order to establish boundary and intermediate relationships between the applied centrifugal field and the liquid flow velocity forces at any radial distance in order to establish desired resultant force relationships in the three-dimensional particle arrays. In practice, however, it is undesirable to utilize geometries with rectangular cross-sections as a result of the anomalous effects of coriolis forces which act in a plane transverse to the rotational plane. In the case of rectangular cross-sections, these otherwise unimportant forces can contribute to interlayer particle motion.

Figure 16:
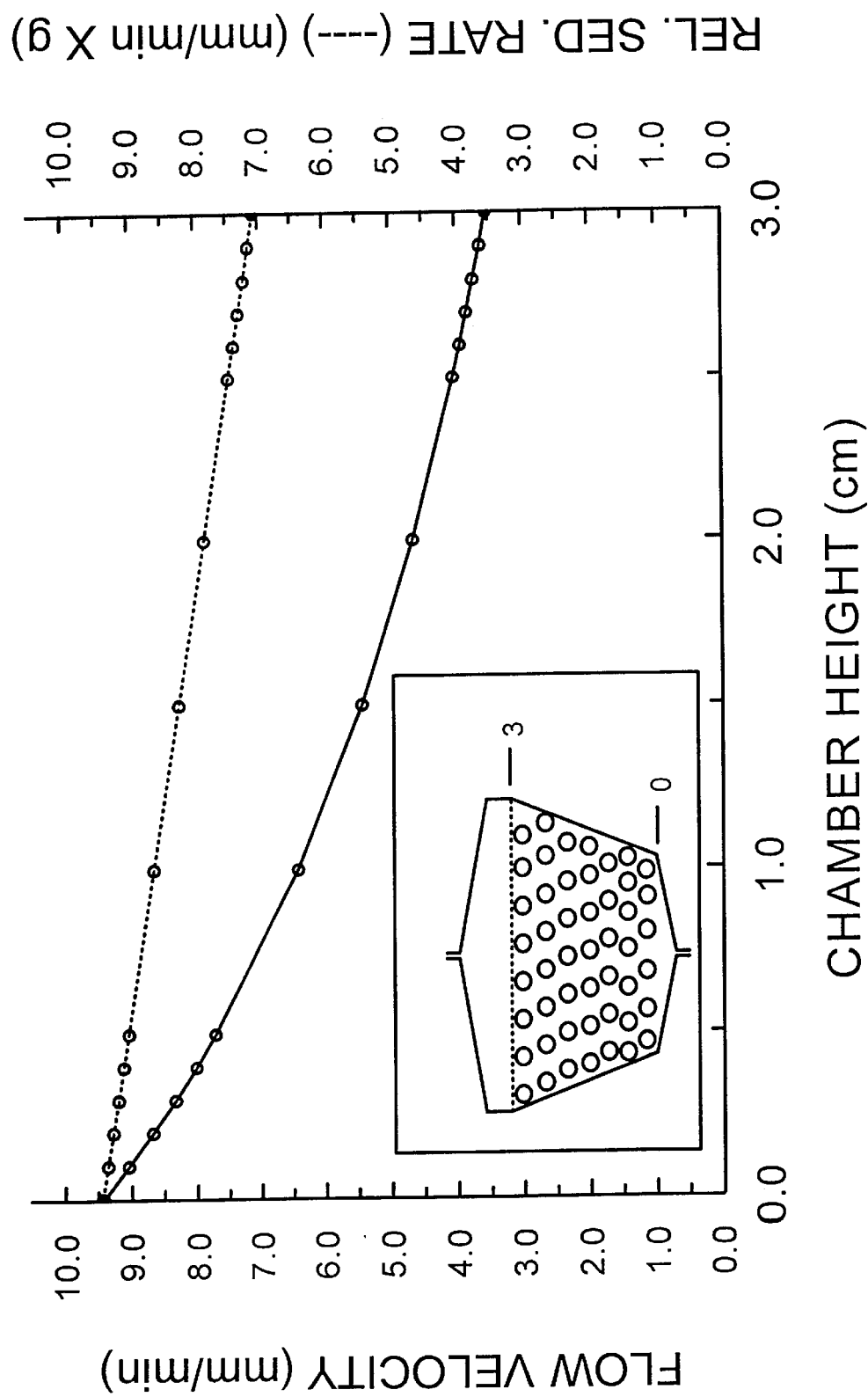
FIG. 16 is an analysis of the positional variation of the centrifugal and flow velocity forces in the chamber of FIG. 15. at a flow rate of 10 mL/min.

It should also be clear from the foregoing that the effect of gravitational forces acting on the individual particle masses which acts independently of the applied centrifugal forces (see FIGS. 7–8) are even less important than was indicated earlier. In particular, since the basic effect of gravity on an otherwise immobilized particle is to either cause radial lengthening or radial shortening, such a motion of a particle will necessarily bring it either into a region of increased flow velocity magnitude (longer radii) or decreased flow velocity magnitude (shorter radii) with only a much smaller change in centrifugal field strength (see FIG. 16).

As a consequence, the periodic motion of a particle due to gravitational effects on its intrinsic mass will be severely dampened in the presence of such unbalanced opposing force fields and will amount to, in the case of low mass particles such as biocatalysts, a "vibration in place."

It should also be obvious from the foregoing that there could be, in a practical sense, a severe problem with the maintenance of the immobilized particle arrays in the above fashion when these particles are aerobic cells, micro-organisms, or biocatalytic substructures. Such structures require, in addition to liquid nutrients, the provision of certain nutrients which are gases at ambient temperatures and pressures. For example, the large majority of cells or micro-organisms which are valuable in the production of commercial biochemicals are aerobes. That is, they require oxygen for viability. While these living organisms (or their subcellular constituents) can only utilize oxygen in a dissolved form, the only method of providing oxygen heretofore was by bubbling or sparging oxygen through the nutrient liquid in which the cells are suspended in order to effect the solubilization of oxygen. Further, most living organisms (including certain anaerobes) produce metabolic wastes which are gases (for example, carbon dioxide or methane). If gas volumes were either introduced into or generated from metabolic processes occurring in the immobilized three-dimensional arrays of particles discussed above, then the careful balance of forces which provides for their immobilization would be destroyed.

Thus, the proper function of the centrifugal immobilization process of this invention requires that provisions be made to eliminate the possibility of either the introduction of, or the generation of, gas(es) within the biocatalyst immobilization chamber. Since the only form of these otherwise gaseous chemicals which is utilizable by these cells (or is produced by them) is the aqueous dissolved form, it is this form which must be preserved in the process of this invention. One may ensure this condition by the application of Henry's Law, which, in essence, states that the quantity of a gas which may be dissolved in a liquid is a function of the system pressure. Thus, if the hydraulic pressure of the liquid-containing system (the biocatalyst immobilization chamber and the liquid lines leading to and from the biocatalyst immobilization chamber) are maintained at a hydraulic pressure sufficient to fully dissolve the necessary quantity of input gas and to insure the solubility of any produced gases, then there will be no disturbance of the immobilization dynamics.

As used herein, the terms "biocatalyst immobilization chamber", "reactor chamber", "bioreactor chamber", "cell confinement chamber", "centrifugal confinement chamber", "centrifugal cell chamber", "immobilization chamber", "chamber", "compartment", or "confinement chamber" are all equivalent descriptive terms for the portion of the invention described herein where cells or biocatalysts are suspended by the described forces. Use of these equivalent terms does not imply an estoppel or limitation of the description of the invention.

Figure 17:
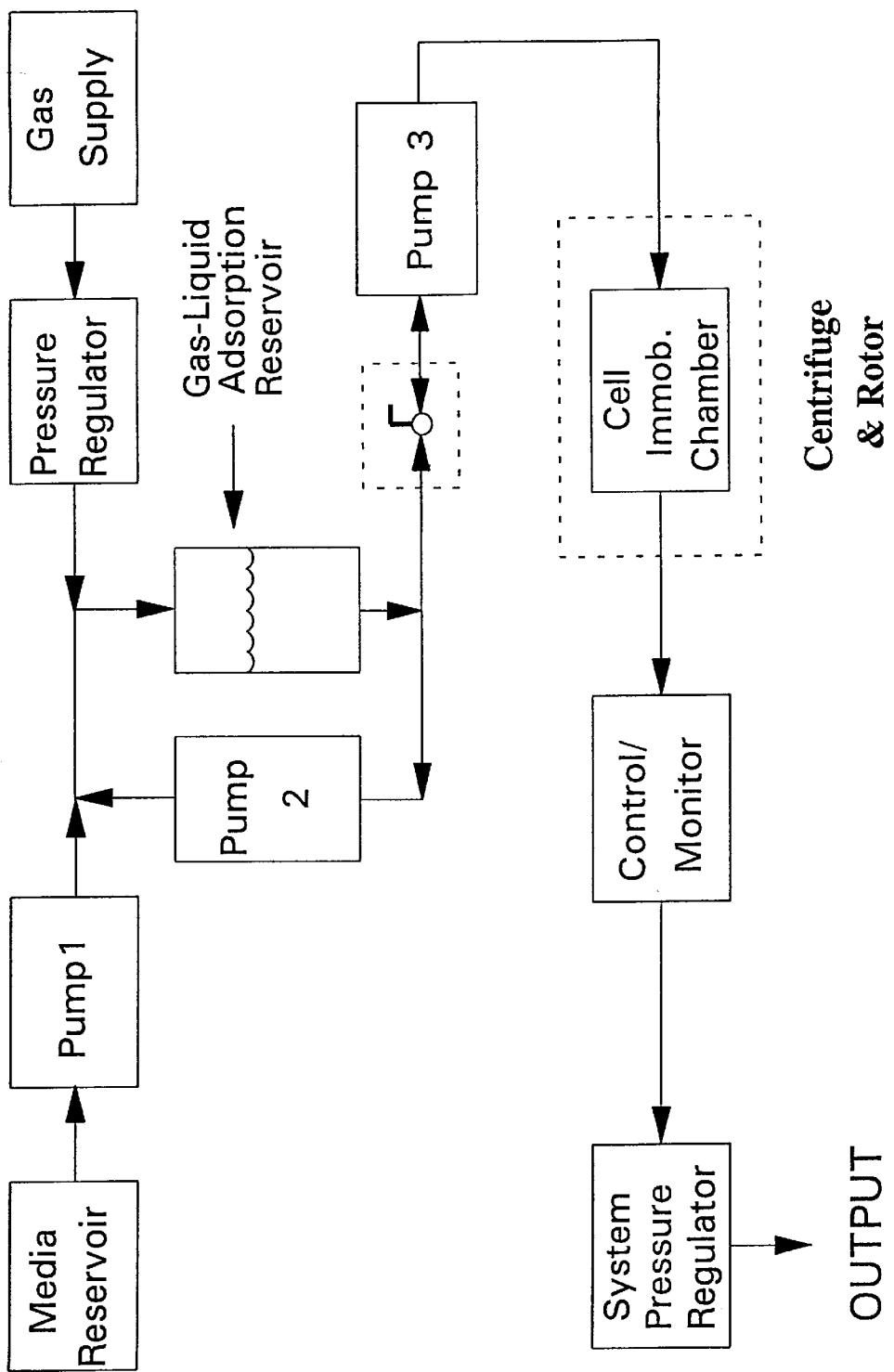
FIG. 17 is a block diagram of a process configuration designed to maintain desired dissolved gas concentrations in the liquid input to a centrifugal bioreactor.

FIG. 17 is a block diagram which demonstrates one method by which the maintenance of such a gas-free, completely liquid system at hydraulic pressures greater than ambient may be effected. In this system, the indicated pumps are all positive displacement pumps. That is, liquid is constrained to motion through the pumps in the directions indicated by the arrows. Pump 3 is the primary feed pump which moves liquids into and out of the cell immobilization chamber which is located in a centrifuge rotor. The raising of the hydraulic pressure in the circuit containing Pump 3 and the cell immobilization chamber is accomplished by placing a liquid pressure regulator, the system pressure regulator, at a position in the circuit downstream of the cell immobilization chamber. Thus, the setting of a pressure limit higher than ambient on the system pressure regulator results in no liquid flow through this circuit until the positive displacement pump, Pump 3, moves enough liquid into the circuit to raise the system hydraulic pressure to a value near this setting. Once an equilibrium system pressure is established, the pressurized liquid downstream of Pump 3 will flow continuously at a rate set by control of Pump 3.

In order to dissolve an appropriate amount of a desired nutrient gas into the liquid input to Pump 3, a Gas-Liquid Adsorption Reservoir is placed in the input line leading to Pump 3. Non-gassed liquids are moved from the Media Reservoir into the Gas-Liquid Adsorption Reservoir by means of Pump 1. Quantities of the desired gas (air or oxygen, for example) are, at the same time, let into the Gas-Liquid Adsorption Reservoir through a pressure regulator set for the gas pressure required to insure the solubilization of the desired concentration of the gas into the nutrient liquid. Note that, in the steady-state, it is necessary that Pump 1 be operated at the same flow rate set for Pump 3. Pump 2 is a recirculation pump which is operated at a flow rate higher than that of Pumps 1 and 3. Pump 2 is used to increase the contact between the gas and liquid phases of the Gas-Liquid Adsorption Reservoir so that a desired concentration of gas dissolved in the nutrient liquid is maintained in the bulk of the volume of liquid in the Gas-Liquid Adsorption Reservoir. It is essential, because of the nature of positive displacement pumps, that the magnitude of the system pressure set with the System Pressure Regulator be higher than the pressure magnitude set in the Gas-Liquid Adsorption Reservoir. In order to make available, at any time, a sufficient volume of liquid equilibrated with the desired concentration of gas(es), a valve on the input to Pump 3 may be utilized to allow such equilibration to occur prior to any actual use. Similarly, by means of switching valves, the liquid input to Pump 3 may be changed from that indicated in FIG. 17 to any other input reservoir desired, subject to the constraint that the hydraulic pressure of such a reservoir be lower than the value of hydraulic pressure set by the System Pressure Regulator.

Figure 18:
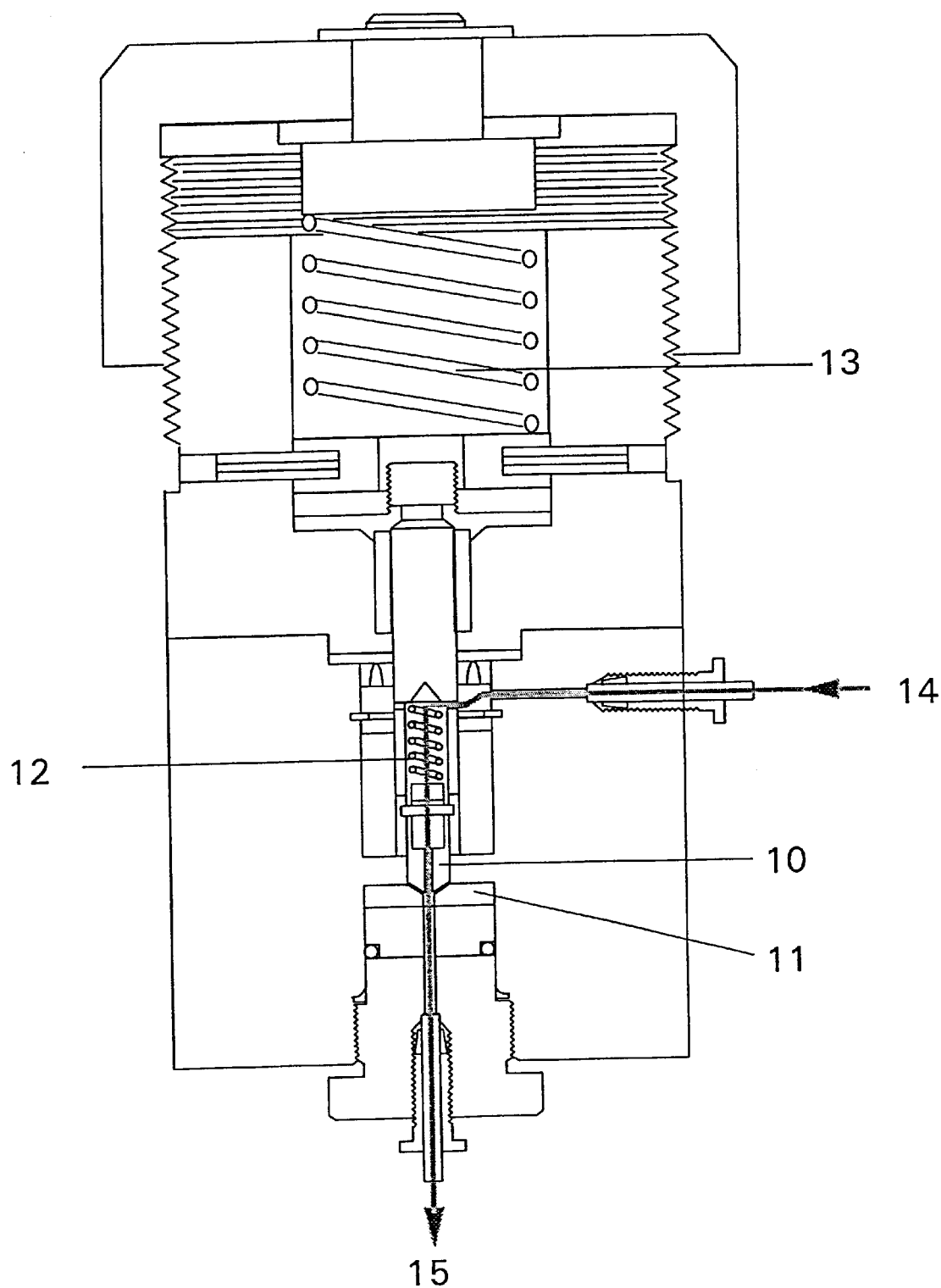
FIG. 18 is an illustration of a representative liquid flow pressure regulator.

FIG. 18 is a depiction of a representative, commercially-available liquid pressure regulator. A flow of liquid 14 into the pressure regulator is obstructed by a spring-loaded needle valve 10 which presses against a seat 11. When the hydraulic pressure of the input liquid becomes great enough, the needle valve 10 is displaced from the seat 11 and a flow can then exit (as indicated by line 15) the pressure regulator. The fixed pressure exerted by the needle valve spring 12 can be adjusted by increasing or decreasing the pressure exerted by the adjustable spring 13.

It should be obvious that the block diagram of FIG. 17 is a representation of one of many process flow configurations which may be employed in order to flow a gas-free pressurized liquid through a centrifugal bioreactor chamber. In particular, one may envision many different methods of insuring adequate mixing of gas and liquid in order to effect the solubilization of a measured quantity of gas into the liquid. What is central to the process of this invention is: (1) that the liquid circuit comprising the bioreactor chamber and the liquid transport lines (into and out of the bioreactor chamber) be operated at a hydraulic pressure greater than ambient pressure; (2) that there be provision for the solubilization of a desired quantity of a gas into the liquid prior to its insertion into the liquid circuit leading to the bioreactor chamber(s); and (3) that the system hydraulic pressure be maintained at a high enough value to keep both the input gas(es), as well as the respiratory gas(es) which may be produced by biological systems in solution throughout the liquid circuit, upstream of the system pressure regulator and downstream of Pump 3. Hydraulic pressures of 100–2000 psig have proved sufficient to maintain a gas-free liquid environment for all possible conditions of cell density and cell number.

There will be no measurable deleterious effects on the culture of animal cells or micro-organisms or their subcellular constituents as a result of the necessity to increase the hydraulic pressure of their environment in the biocatalyst immobilization chamber at hydraulic pressures below 10,000 psig. The successful culture of living cells using bioreactor headspace pressurization is a proven and established culture method, albeit limited in scope to pressures of less than 50 psig (see Yang, J. and Wang, N. S. (1992) Biotechnol. Prog. 8, 244–251 and references therein). At hydraulic pressures of 15,000 to 30,000 psig some disassociation of noncovalent protein complexes has been observed, although pressures of more than 90,000 psig are required to denature monomeric proteins (Yarmush, et al. (1992) Biotechnol. Prog. 8, 168–178). It is a seldom appreciated, but well known fact that living cells (and their constituent parts) are unaffected by, and indeed cannot sense hydraulic pressure magnitudes below those limits outlined above. This may best be appreciated in considering the effects of hydraulic pressure on marine organisms. For every 10 meters of depth under the sea, approximately one atmosphere (14.7 psig) of overpressure is gained. Thus, for example, benthic organisms exhibiting biochemical processes and metabolic pathways identical to their shallow-water and terrestrial counterparts inhabit ecological niches and proliferate mightily at hydraulic pressures of more than 3000 pounds per square inch. Similarly, the hydraulic pressure under which terrestrial mammalian cells exist is greater than ambient, ranging from ca. 90 to 120 mm Hg greater than ambient in man, for example. The explanation for the "invisibility" of hydraulic pressure in biological systems can be understood if it is realized that hydraulic pressure in aqueous systems has, as its "force carrier," the water molecule. Since the lipid bilayer which forms the boundary membrane of living cells is completely permeable to water molecules, an applied hydraulic pressure in aqueous systems is transmitted across the boundary membranes of cells or subcellular organelles by the movement of water molecules with the result that the interior(s) of cells rapidly equilibrate to an externally-applied aqueous hydraulic pressure.

There are situations in which hydraulic pressures are deleterious to living cells. For example, if a pressure field in an aqueous system is varied at high frequency, then it is possible to cause cell disruption by means of pressure differentials across the cell boundary membrane. However, the frequency required for such lethal effects is quite high; on the order of thousands of cycles per second. As long as the pulsatile pressure of pumping in the process of this invention is kept below such a limit there is no effect on cell viability for even the most fragile of cells as a result of pressure fluctuations. In addition, cell replication is completely unaffected by culture at increased hydraulic pressure.

The problem of the introduction and withdrawal of pressurized liquid flows into and out of a rotating system has been solved by innovations in seal design over the past twenty years. High performance mechanical end-face seals are available which are capable of operation at rotational rates in excess of 5000 revolutions per minute while maintaining a product stream hydraulic pressure of more than 2000 psig. Such seals are available from Durametallic Corporation (2104 Factory Street, Kalamazoo, Mich. 49001). Such high-performance mechanical seals have leakage rates below 5 liters per year, can be cooled by pressurized refrigerated liquids of which inadvertent leakage into the product stream at the above leakage rates will have no effect on biological systems, and can be operated in a manner which provides for the maintenance of absolute sterility in the product stream. The somewhat inexplicable aversion to the use of mechanical end-face seals for use in centrifugal bioreactor systems (see U.S. Pat. Nos. 4,939,087 and 5,151,368, for example) results in a perceived necessity for the connection of flexible tubing (and complicated mechanisms for its "untwisting") in conventional designs. Such designs are, as a result, limited to: (1) hydraulic pressures near one atmosphere as a consequence of tube flexibility requirements; and (2) low rotational speeds and short bioreactor run times as a result of the vigorous motion of these flexing connections. The use of modern high performance mechanical end-face seals eliminate all of these drawbacks to centrifugal bioreactor performance.

Immobilization of three-dimensional arrays of particles in a force field, which is comprised of outwardly-directed centrifugal forces which are opposed by inwardly-directed liquid flow forces has been described. The effect of gravitational forces which act, inevitably, on even the smallest and lightest of particles over prolonged time periods can be essentially negated and reduced to a small periodic "vibration in place" by the proper choice of rotational axis. The disruptive effects of the possible introduction of gases into this system have been accounted for by raising the hydraulic pressure of the liquid system to values which assure that such otherwise gaseous chemicals will remain dissolved in the flowing liquid. It has been emphasized that the necessary increase in hydraulic pressure will have no effect on biological units such as cells, microorganisms, or their subcellular constituents.

Figure 19:
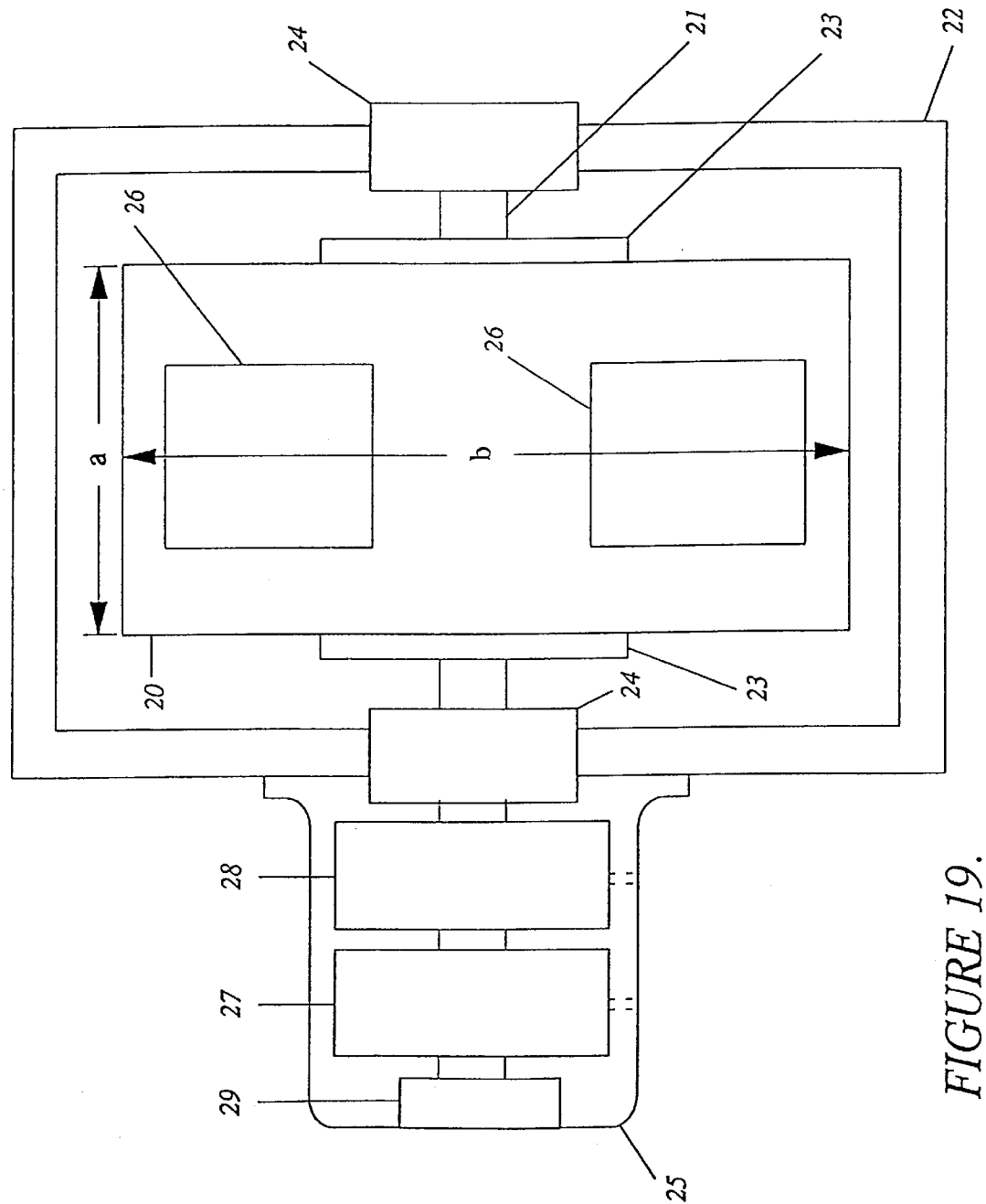
FIG. 19 is a sectional view of a first embodiment of the Centrifugal Fermentation Process when viewed parallel to the axis of rotation.

In the following paragraphs, we present and analyze two embodiments of the invention. FIG. 19 depicts the components of a first embodiment of the present invention. A cylindrical rotor body 20 is mounted on a horizontal, motor-driven rotating shaft 21 inside a safety containment chamber 22 bounded by metal walls. The rotor body 20 is fixed in position on the rotating shaft 21 by means of locking collars 23. The rotating shaft 21 is supported on either side of the rotor body 20 by bearings 24. The rotating shaft 21 extends outside the safety containment chamber 22 for a distance and ends in a terminal bearing and end cap 29 mounted in an external housing 25. Liquid flows are introduced into and removed from bioreactor chambers 26 mounted in the rotor body 20 by means of a liquid input mechanical end-face seal 28 and a liquid output mechanical end-face seal 27 which communicate with liquid channels (50, 51 in FIG. 22) within the rotating shaft 21. Typical dimensions for an example rotor body 20 (a=36 cm and b=15 cm) are entirely reasonable and comparable to rotor dimensions known to those skilled in the art.

Figure 20:
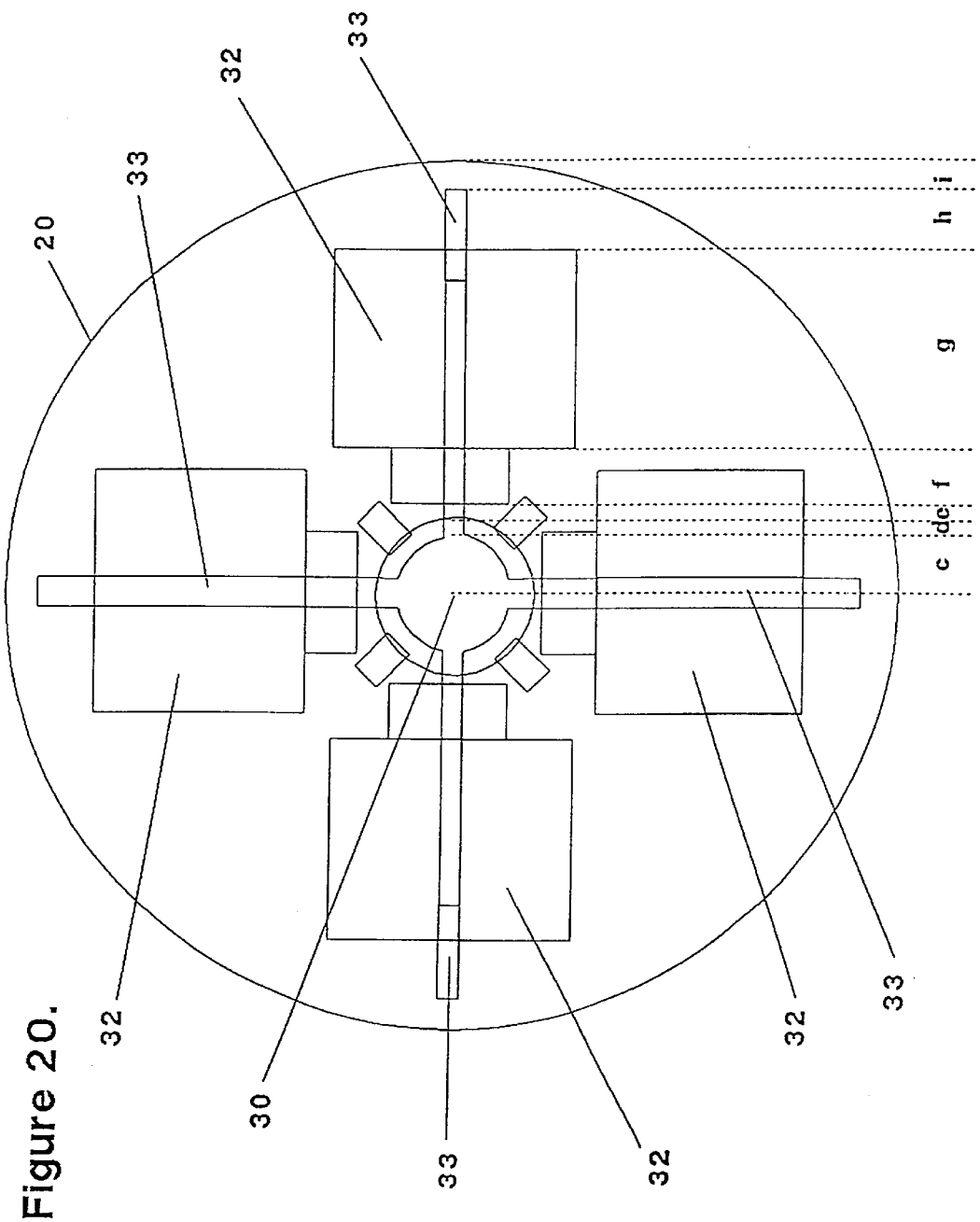
FIG. 20 is a view of the rotor body of FIG. 19 when viewed parallel to the axis of rotation.

FIG. 20 is a view of the rotor body 20 of FIG. 19 as viewed parallel to the axis of rotation. The rotor body 20 is machined with a shaft mounting channel 30 through its center to allow its mounting on the rotating shaft (21 in FIG. 19), and is machined to have chamber-positioning recesses 32 into which cylindrical demountable bioreactor chambers (26 in FIG. 19) may be placed. The rotor body 20 is also machined to have radial rectilinear channels 33 (such as the centrally-located axial liquid output channel 51 in FIG. 22, and the eccentric axial liquid input channel 50 in FIG. 22) in which liquid lines (such as the output liquid transport lines 53 in FIG. 22 and the input liquid transport lines 54 in FIG. 22) which communicate with the bioreactor chambers (26 in FIG. 22) may be located. In actual use, a circular cover (not shown) would be attached to the surface of the rotor body 20 to close the rotor body 20.

Figure 21:
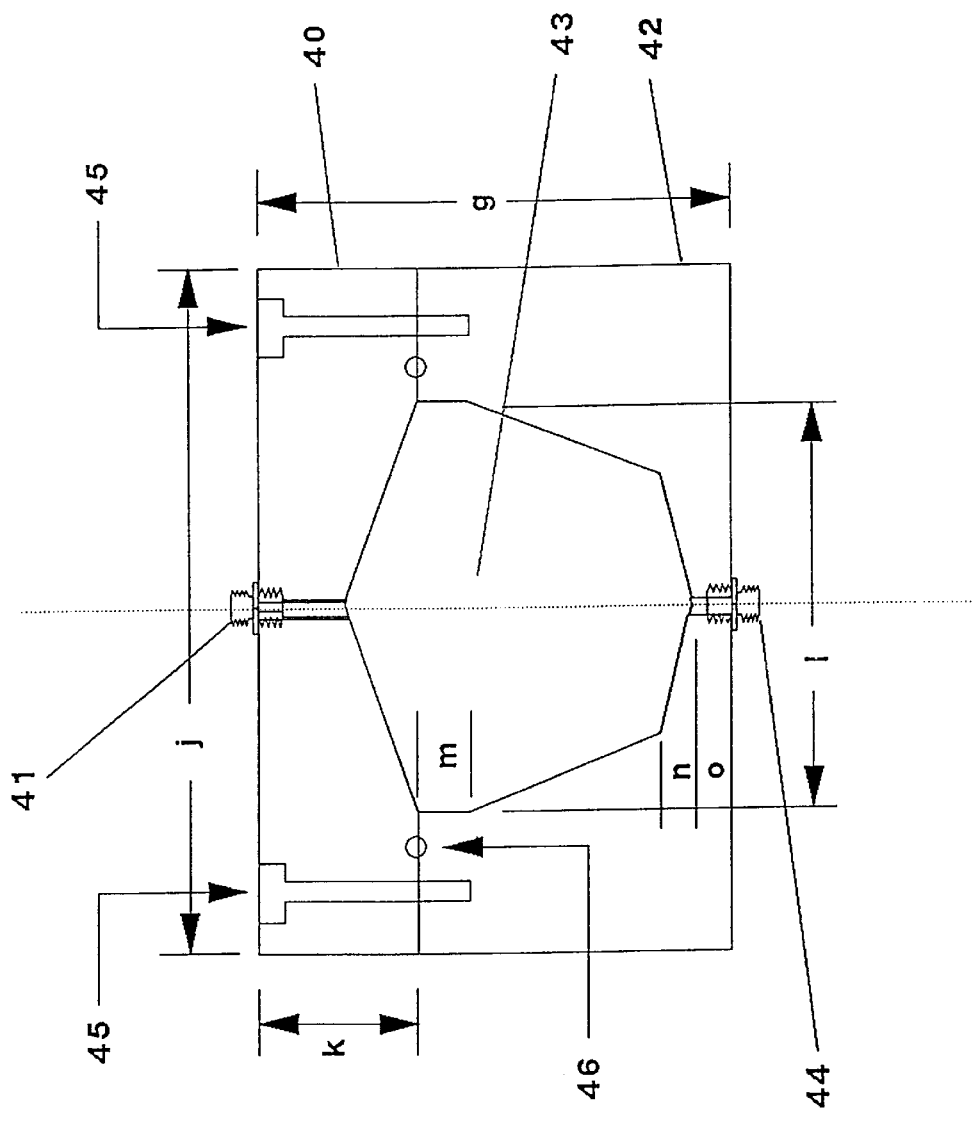
FIG. 21. is a cross-sectional view of one of the demountable bioreactor chambers of FIG. 19.

FIG. 21 is a depiction of one of the bioreactor chambers 26 of FIG. 19. The bioreactor chamber (26 in FIG. 19) is cylindrical and is composed of two pieces of thick-walled metal; a top piece 40 and a bottom piece 42. The top piece 40 contains a machined conical recess 47 and a machined passage 48 terminating in an output compression fitting 41 by which liquid may be removed from the bioreactor chamber (26 in FIG. 19). The bottom piece 42 is made of the same metal as the top piece 40, and is internally machined to form a biocatalyst immobilization chamber 43 of a desired geometric shape. The shape of the biocatalyst immobilization chamber 43 depicted in FIG. 21 is that of a truncated cone with a short cylindrical volume at its top face and a short conical volume at its bottom face. A machined passage 48 terminating in an input compression fitting 44 allows liquid input into the biocatalyst immobilization chamber 43. The top piece 40 and the bottom piece 42 of the biocatalyst immobilization chamber 43 are bolted together by means of countersunk assembly screws 45 and sealed against an internal positive hydraulic pressure by means of one or more O-ring compression seals 46. In the case of certain animal cell cultures in which contact between the immobilized cells and the interior metal walls of the biocatalyst immobilization chamber 43 should be avoided, it may be expedient to provide suitable conical inserts of, for example, polyethylene, in order to prevent such contact. Alternatively, the interior of the biocatalyst immobilization chamber 43 might be coated with an appropriate lining material to provide the same effect.

Figure 22:
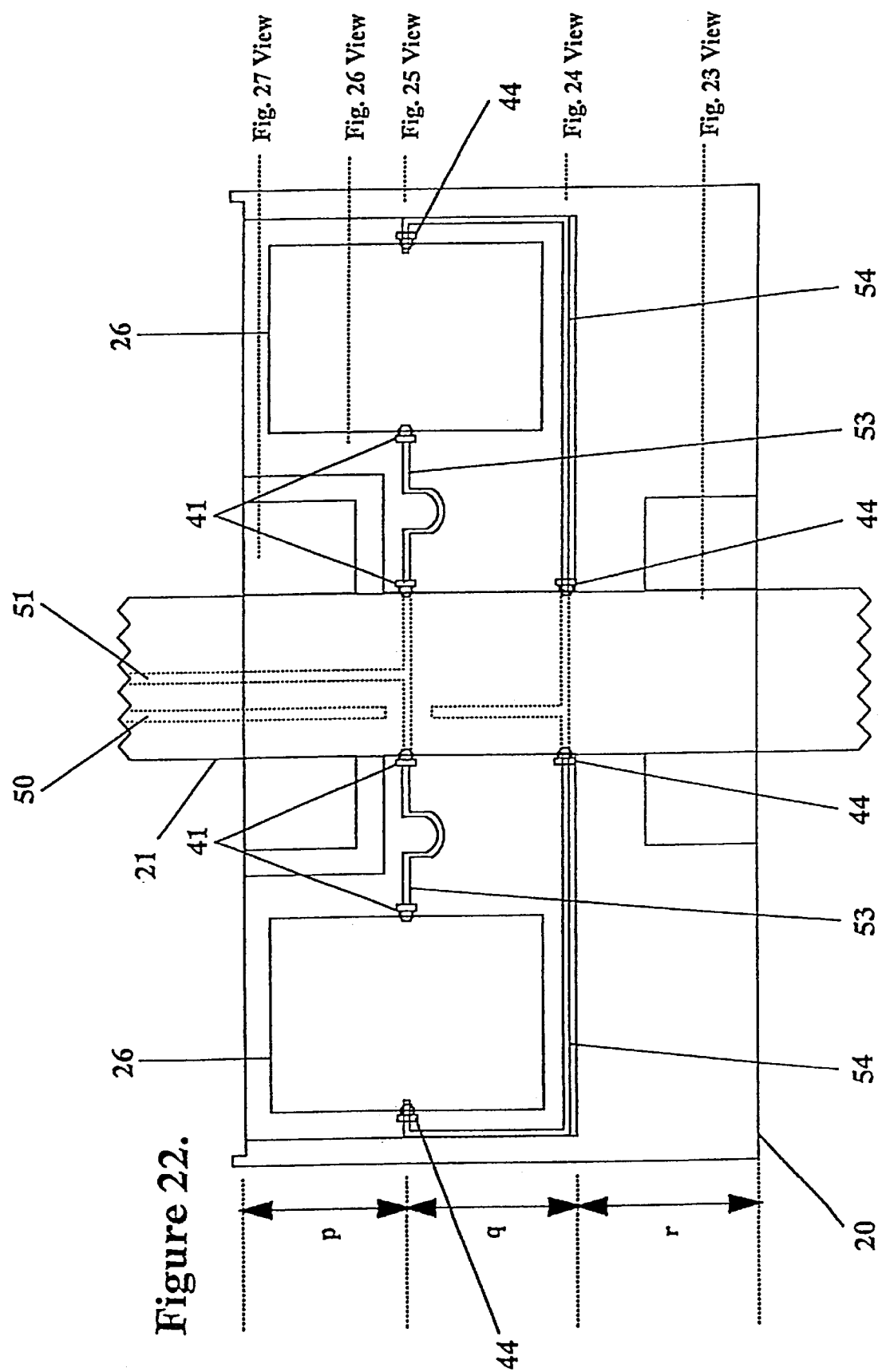
FIG. 22 is a sectional view of the rotor body of FIG. 19 when viewed perpendicular to the axis of rotation.

FIG. 22 is a transverse sectional view through the rotor body 20 of FIG. 19 parallel to the axis of rotation. The bioreactor chambers 26 are connected to an eccentric axial liquid input channel 50 and to a centrally-located axial liquid output channel 51 within the rotating shaft 21 by means of output liquid transport lines 53 and input liquid transport lines 54. The output liquid transport lines 53 are metal tubes which communicate with the bioreactor chambers 26 and the centrally-located axial liquid output channel 51 through output compression fittings 41. The input liquid transport lines 54 are metal tubes which communicate with the bioreactor chambers 26 and the eccentric axial liquid input channel 50 through input compression fittings 44. The exact machining of the rotor body 20 may be examined by five different sectional views of the rotor body 20 perpendicular to the axis of rotation (see FIGS. 23–27) which are sectional views at the levels indicated by the dotted lines in FIG. 22.

Figure 23:
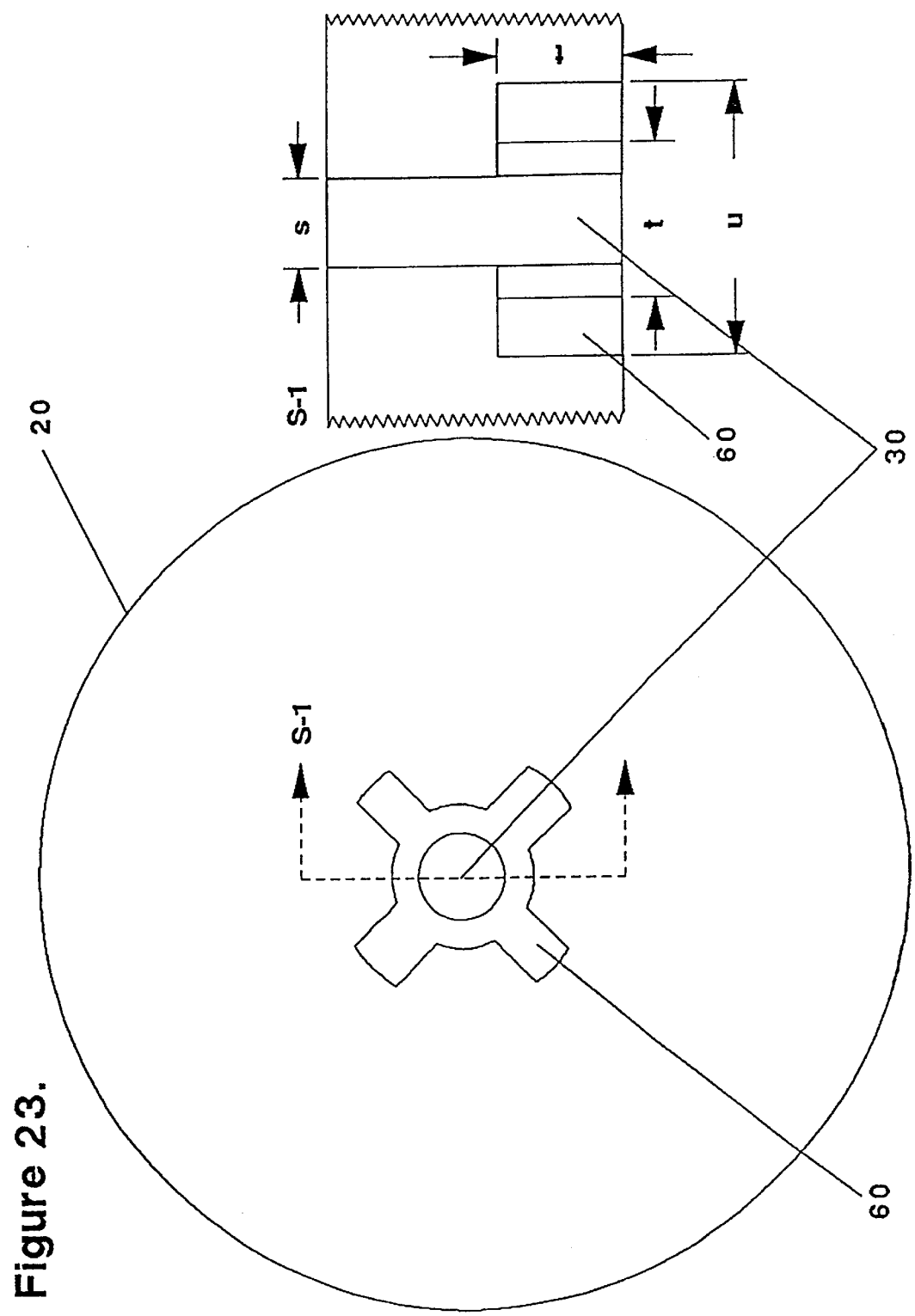
FIG. 23 is a sectional view of the rotor body of FIG. 19 along the dotted line indicated in FIG. 22, when viewed parallel to the axis of rotation.
Figure 24:
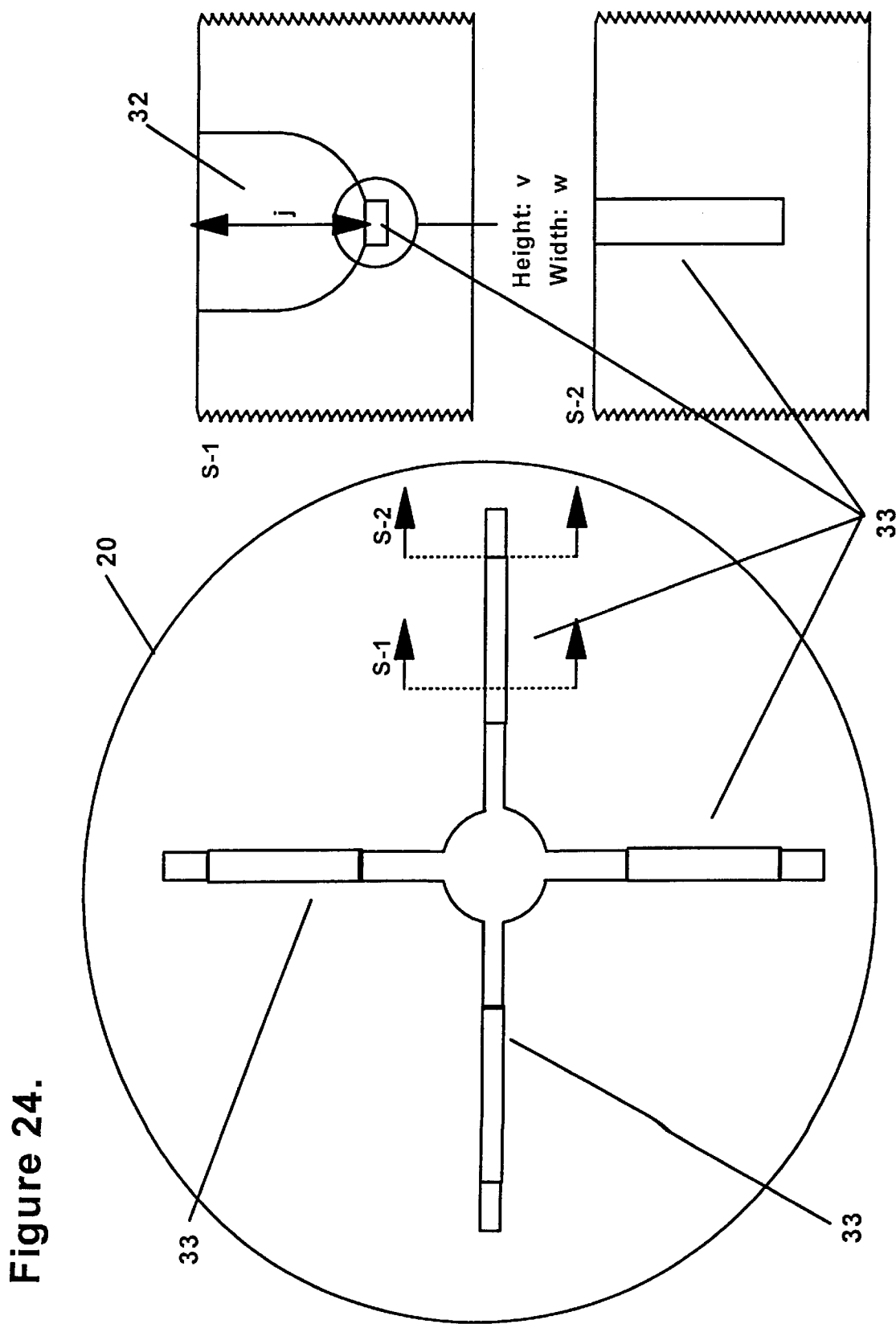
FIG. 24 is a sectional view of the rotor body of FIG. 19 along the dotted line indicated in FIG. 22, when viewed parallel to the axis of rotation.
Figure 25:
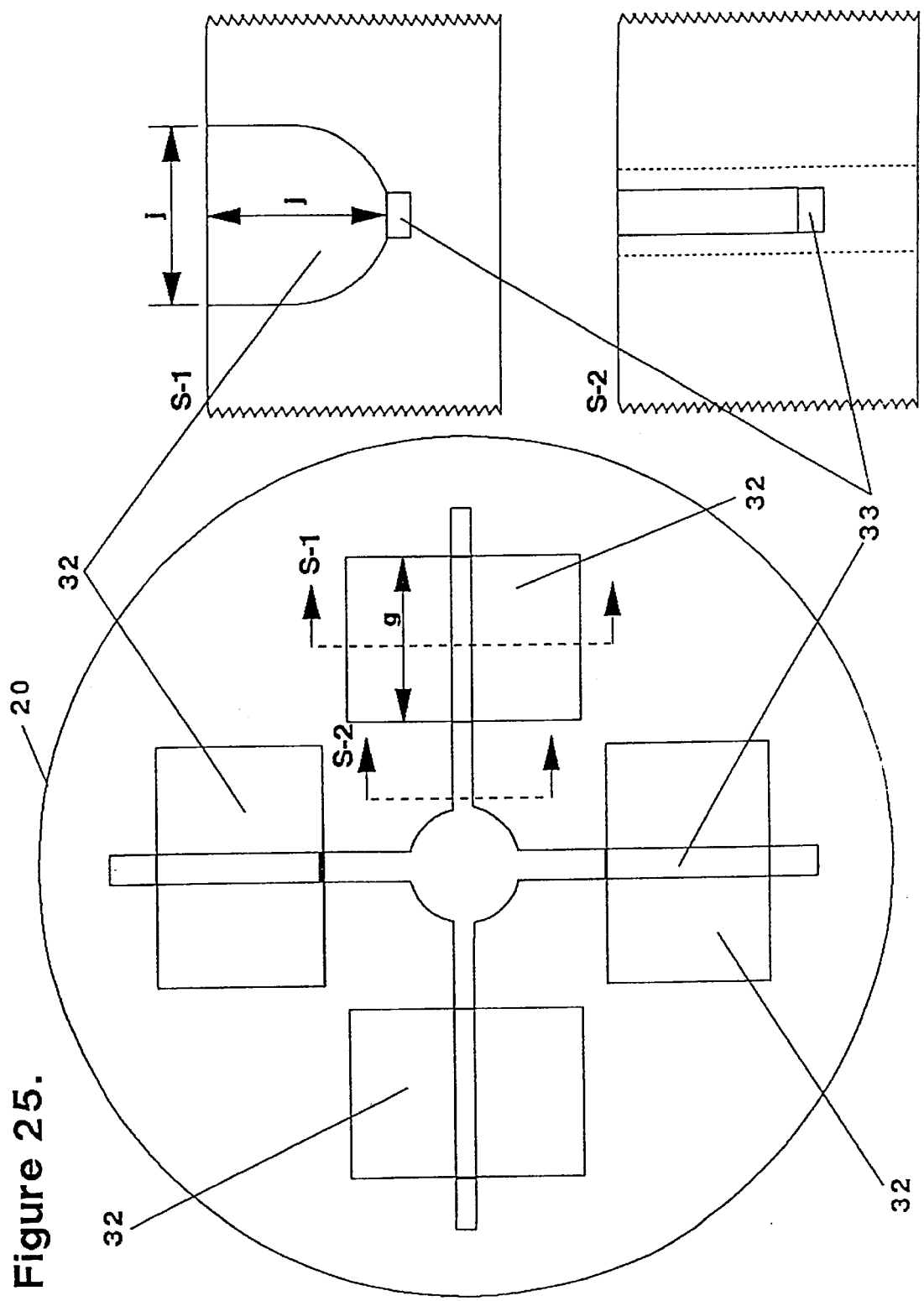
FIG. 25 is a sectional view of the rotor body of FIG. 19 along the dotted line indicated in FIG. 22, when viewed parallel to the axis of rotation.
Figure 26:
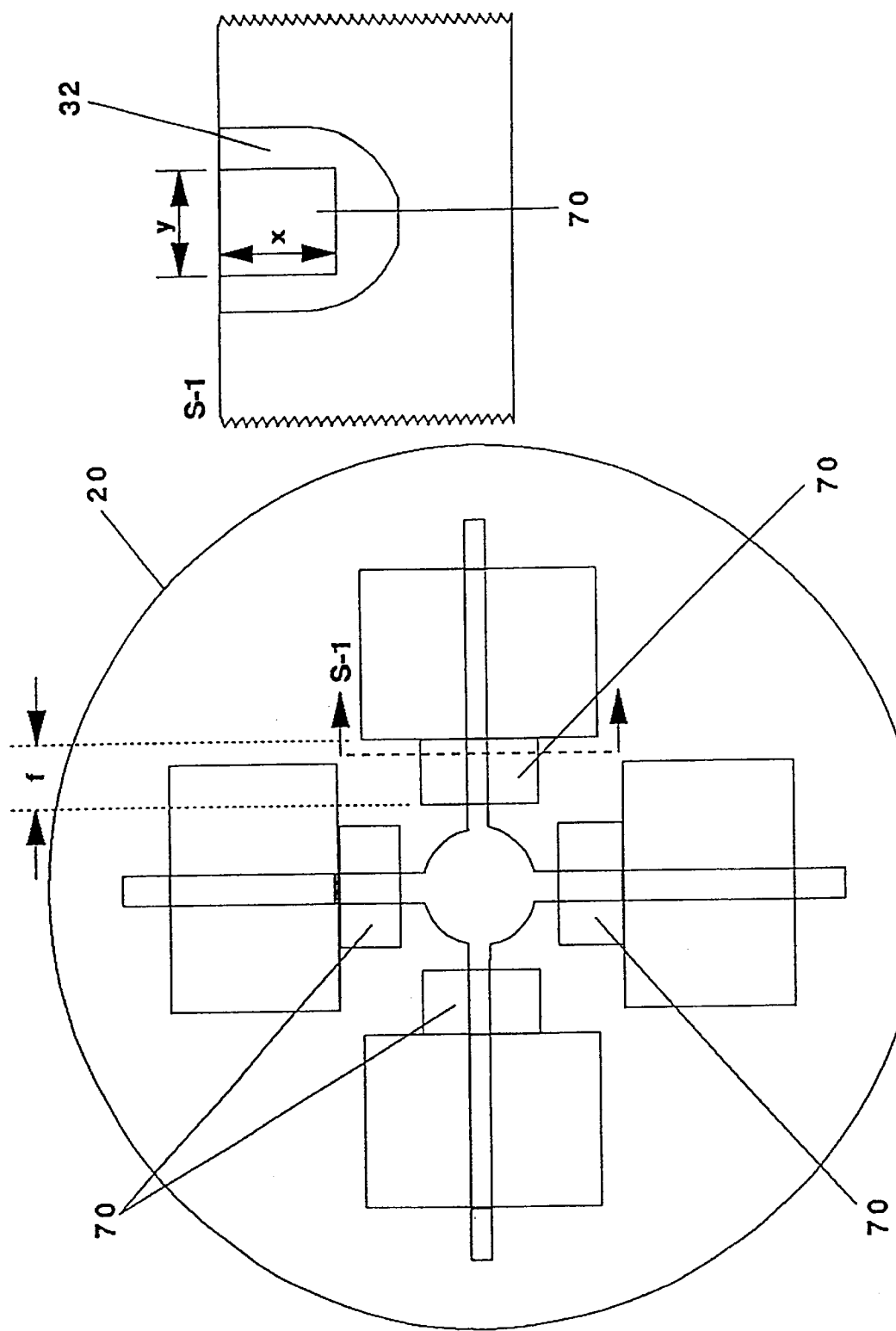
FIG. 26 is a sectional view of the rotor body of FIG. 19 along the dotted line indicated in FIG. 22, when viewed parallel to the axis of rotation.
Figure 27:
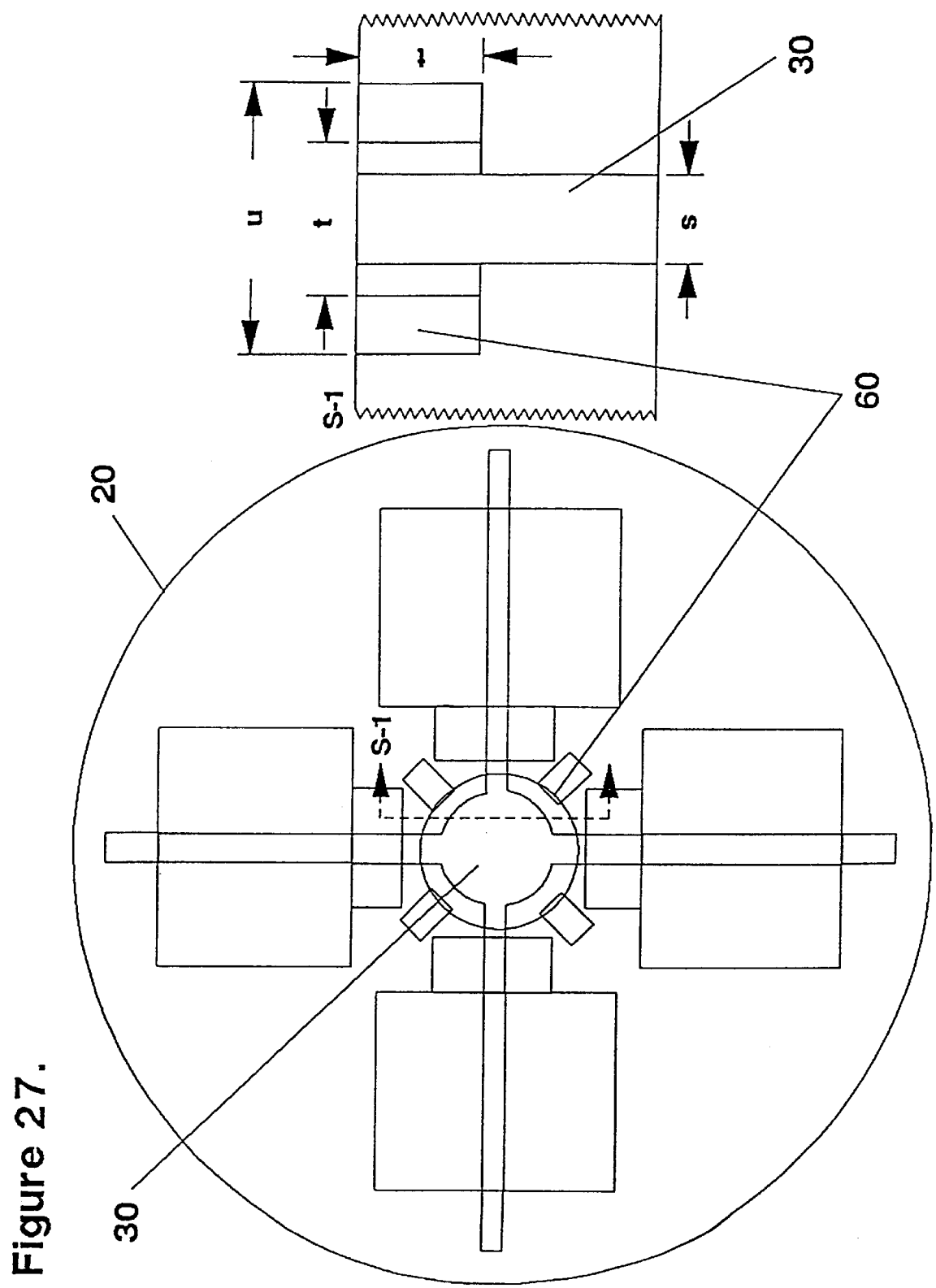
FIG. 27 is a sectional view of the rotor body of FIG. 19 along the dotted line indicated in FIG. 22, when viewed parallel to the axis of rotation.

In FIGS. 23–27, the dimensions and configuration of five different internally-machined sections of the rotor body 20 of FIG. 19 are displayed. FIGS. 23 and 27 show one method by which the rotor body 20 may be mounted on the rotating shaft (21 in FIG. 19) by means of sprocket-shaped recesses 60 concentric with the shaft mounting channel 30 which accept the locking collars (23 in FIG. 19). S-1 in FIGS. 23 and 27 is a cross-sectional view of the shaft mounting channel 30 and the sprocket-shaped recesses 60. FIG. 24 depicts four radial rectilinear channels 33 machined into the rotor body 20 into which the output and input liquid transport lines (53 and 54, respectively, in FIG. 22) will travel. FIG. 25 depicts the shapes of the chamber-positioning recesses 32 machined into the rotor body 20 into which the bioreactor chambers (26 in FIG. 19) are placed, and also shows the relationship of these chamber-positioning recesses 32 to the radial rectilinear channels 33. Note that the radial rectilinear channels 33 extend farther radially than do the chamber-positioning recesses 32 and thus provide a support channel against which the output and input liquid transport lines (53 and 54, respectively, in FIG. 22) rest as they extend "upward" to connect with an input compression fitting (44 in FIG. 21) of the bioreactor chambers (26 in FIG. 22). Because each input liquid transport line (54 in FIG. 22) is supported by resting against a wall of the most distal radial rectilinear channel 33 as the most distal radial rectilinear channel 33 makes a right angle bend to travel to its terminus at an input compression fitting (44 in FIG. 21) of each bioreactor chamber (see section S-2, FIG. 24), there is no extra centrifugal stress applied to the input liquid transport lines (54 in FIG. 22) as a result of the rotational movement of the system.

FIG. 26 details the internal machining of the rotor body 20 of FIG. 19 for the liquid output line attachment recesses 70 necessary to provide working room for the mechanical attachment of the output liquid transport lines (53 in FIG. 22) to the bioreactor chambers (26 in FIG. 19), using output compression fittings (41 in FIG. 21). As is shown in FIG. 22, the output liquid transport lines 53 are bent into a "U-shaped" configuration (exaggerated in FIG. 22) which allows their length to be adjusted during mechanical connection to the bioreactor chambers (26 in FIG. 19). The bioreactor chambers (26 in FIG. 19) are supported against centrifugal stress by the distal walls of the chamber-positioning recesses 32; no weight is imparted to the output liquid transport lines (53 in FIG. 22) (except their own) as a result of centrifugal forces.

Figure 28:
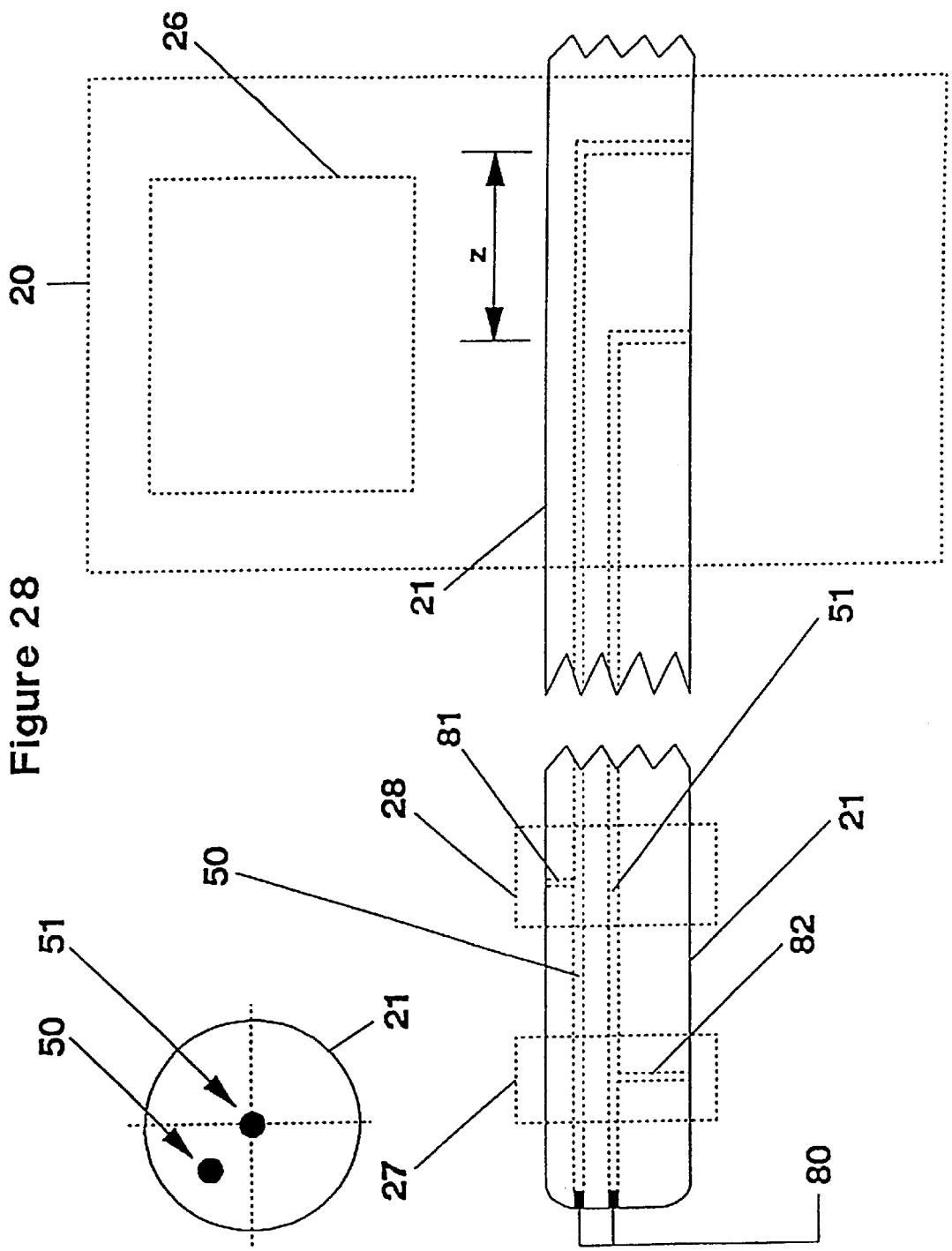
FIG. 28 is an illustration of the axial channels and their termini in the rotating shaft of FIG. 19.

FIG. 28 is a view of the portion of the rotating shaft 21 on which the rotor body 20 is mounted, and the portion of the rotating shaft 21 on which the liquid output mechanical end-face seal 27 and the liquid input mechanical end-face seal 28, which convey liquid flows into and out of the bioreactor chambers 26, are mounted. The rotating shaft 21 contains two axial liquid transport channels; the eccentric axial liquid input channel 50, and the centrally-located axial liquid output channel 51. The centrally-located axial liquid output channel 51 transports the liquid output of the bioreactor chambers 26 to the liquid output mechanical end-face seal 27 by means of a short radially-directed connecting passage 82 while the eccentric axial liquid input channel 50 conveys liquid from the liquid input mechanical end-face seal 28 to the bioreactor chambers 26, also by means of a short radially-directed connecting passage 81. The eccentric axial liquid input channel 50 and the centrally-located axial liquid output channel 51 extend from one end of the rotating shaft 21 to the region where the rotor body 20 is located. Compression plugs 80 seal the terminal axial openings of both the eccentric axial liquid input channel 50 and the centrally-located axial liquid output channel 51.

Figure 29:
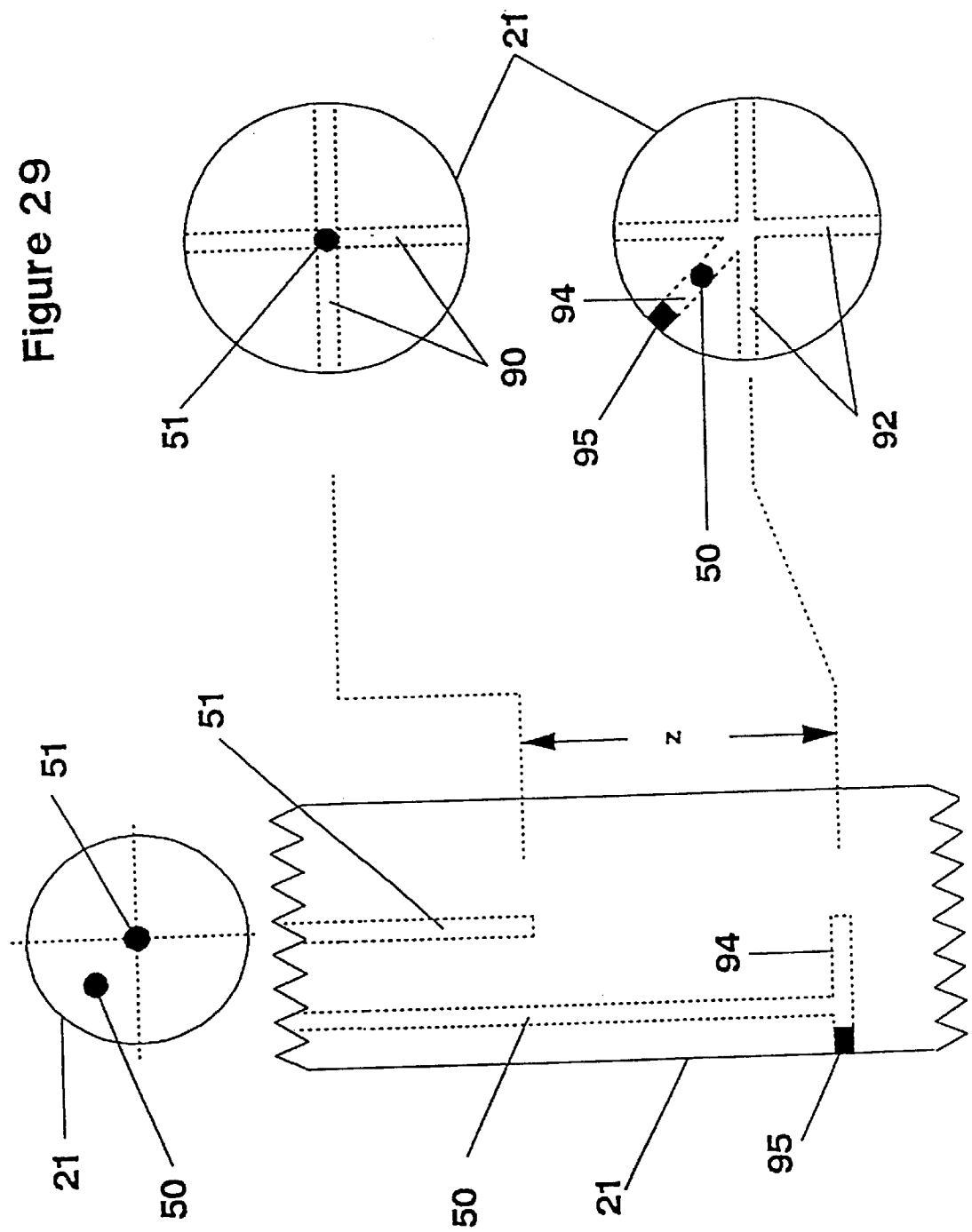
FIG. 29 is a detail view of the distribution hub of the rotating shaft of FIG. 28.

FIG. 29 is a view of the radially-disposed liquid distribution channel hubs in the region of the rotating shaft 21 where the rotor body (20 in FIG. 19) will be mounted. Two pairs of channels; the radial output liquid line channels 90 and the radial input liquid line channels 92 are machined through two cross-sections of the rotating shaft 21. The radial output liquid line channels 90 are in direct communication with the eccentric axial liquid input channel 50. In the case of the radial input liquid line channels 92, an additional radial passage 94 is machined which connects the eccentric axial liquid input channel 50 with the central connection of the radial input liquid line channels 92. This additional radial passage 94 is sealed with a compression plug 95 at the surface of the rotating shaft 21. In actual practice, particularly in the case of high-speed operation of the invention, it may be preferable that the eccentric axial liquid input channel 50, and the centrally-located axial liquid output channel 51, be eccentric to the axis of rotation and located symmetrically on a diameter of the rotating shaft 21 for balancing purposes.

Figure 30:
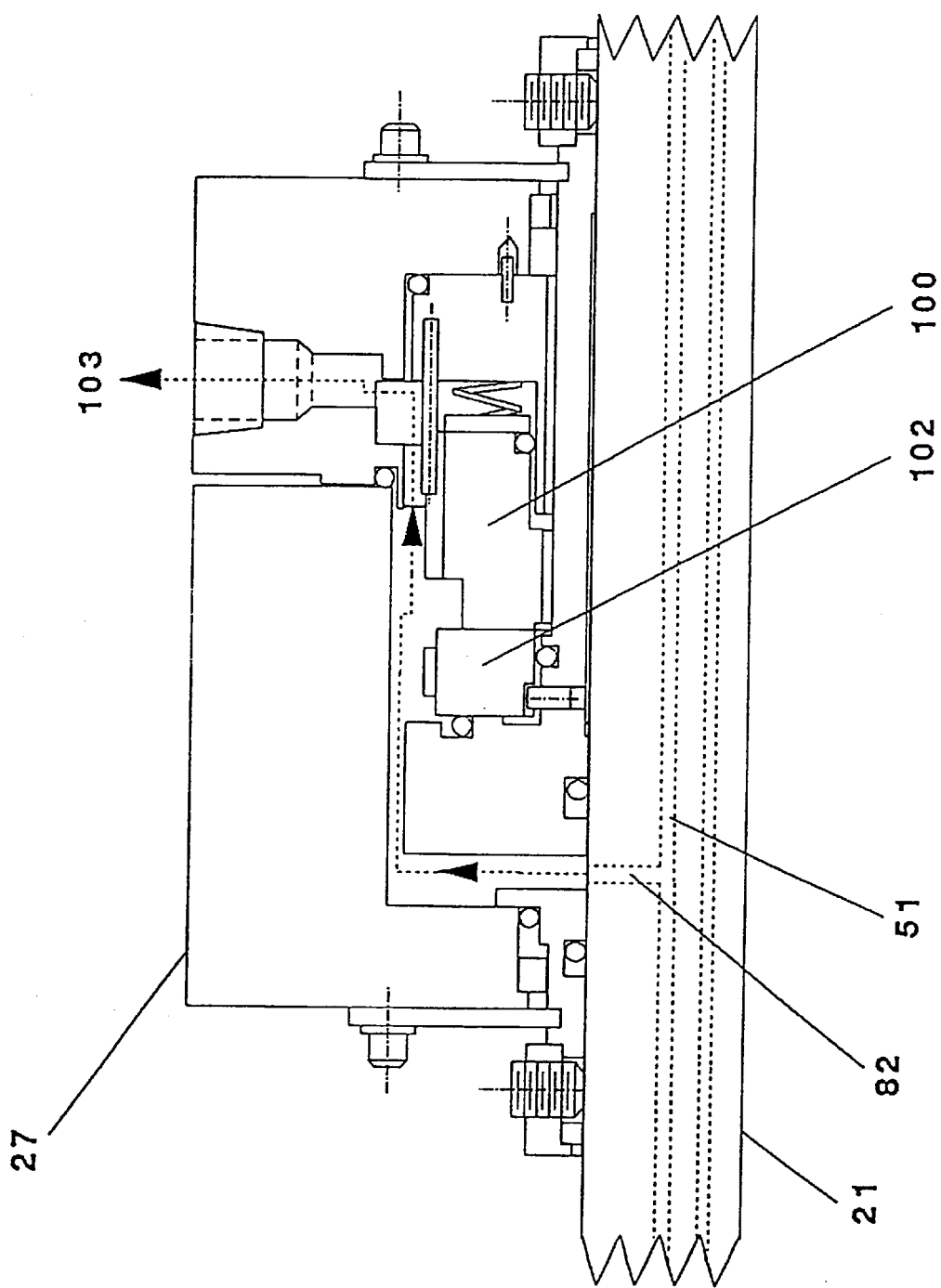
FIG. 30 is a sectional view of a representative high-performance end face seal.

FIG. 30 is a view of a liquid output mechanical end-face seal assembly, such as the liquid output mechanical end-face seal 27, shown in FIG. 19. The liquid output mechanical end-face seal 27 is mounted on the rotating shaft 21 and positioned with an opening to the interior liquid space of the seal over a short radially-directed passage 82 which communicates with the centrally-located axial liquid output channel 51 machined into the rotating shaft 21. A seal between the rotating and stationary portions of the liquid output mechanical end-face seal 27 is provided by the contact of the stationary seal face 100 against the rotating seal face 102. In the case of high performance end-face seals utilizable in the process of this invention, where consideration must be made for the resultant centrifugal forces which act on the seal components, all spring elements are located in the stationary portion of the seal assembly. While the seal configuration shown in FIG. 30 is that of a single seal, double and/or tandem end-face seal configurations may prove more advantageous in prolonged usage. Not shown in the figure are pressurized cooling liquid passages and jacketing necessary to maintain temperature equilibrium in the seal assembly. When such a liquid output mechanical end-face seal assembly is mounted on the rotating shaft 21 of the present invention, aqueous liquids may be pumped into the stationary part of the seal assembly via compression fitting attachment, and the pumped liquid will follow the path indicated by the dotted line 103 to make communication with the centrally-located axial liquid output channel 51 which transports this liquid away from the bioreactor chambers (26 in FIG. 28) mounted in the rotor body (20 in FIG. 28).

The principal disadvantage heretofore in the employment of mechanical seals for the transfer of liquids into and out of rotating systems, where the purpose of the system is to culture biological entities such as animal cells or micro-organisms, has been the problem of the maintenance of sterility. Low pressure mechanical seals have, in the past, provided a route by which adventitious micro-organisms can gain entrance into bioreactor systems via the thin film of internal liquid which lubricates the end-face seal surfaces. In the process of this invention, where the internal liquid is always held at a hydraulic pressure higher than ambient, all leakage of liquid will occur to the exterior of the system. There is thus no possible route through which adventitious contaminants can enter the system. Furthermore, the small leakage of internal nutrient or product liquid which might exit the bioreactor system through the mechanical seals of the process of this invention (which might, for example, contain micro-organisms in certain applications) will not be free to dissipate into the environment. As a consequence of the operating characteristics of high-speed, high-pressure mechanical seals, it will be necessary to surround the seal components with a pressurized cooling liquid flow. It has been found, in practice, that an ideal liquid which possesses the proper viscosity and flow properties for the cooling of such seals is 75–85% glycerol. Any leakage of internal liquid to the exterior in the process of this invention will result in its dispersion into the body of this recirculated liquid. We have found that glycerol at this concentration is completely unable to support the growth of a number of representative animal cells or micro-organisms; this is likely a general phenomenon, presumably as a result of the osmotic movement of water out of the living cells into the glycerol. Thus, periodic sanitary disposal of the cooling liquid volume of glycerol when it becomes diluted with leakage volumes and its replacement with fresh glycerol will serve to maintain sterility in the single place in the system where liquids might escape. Finally, since it is possible, after prolonged use, that loss of internal system pressure or incipient failure of the seal systems might allow liquid flow in the reverse direction across the seal faces, it is important to note that small quantities of glycerol which could thus leak into the bioreactor system would not be anything but an additional nutrient when diluted into the flowing internal process liquid.

In order to obtain data for an analysis of the performance of a rotor body of the dimensions and configuration outlined in FIGS. 19–20 and 22–29 and containing demountable cylindrical bioreactor chambers (26 in FIG. 21), it was necessary that several scale dimensions and boundary equations be chosen arbitrarily and used to determine the operating characteristics of the first embodiment of the present invention. The immobilization boundary equations chosen are those listed in Equations 1 and 2 of FIG. 15. The rotor dimensions chosen for this example and indicated by letter in FIGS. 19–29 are as follows:

| a: | 15.0 cm | j: | 10.0 cm | s: | 2.54 cm |
|---|---|---|---|---|---|
| b: | 36.0 cm | k: | 1.50 cm | t: | 4.0 cm |
| c: | 1.27 cm | l: | 6.0 cm | u: | 6.14 cm |
| d: | 1.0 cm | m: | 0.5 cm | v: | 1.0 cm |
| e: | 1.73 cm | n: | 1.0 cm | w: | 1.0 cm |
| f: | 3.0 cm | o: | 1.0 cm | x: | 6.5 cm |
| g: | 7.0 cm | p: | 5.0 cm | y: | 5.0 cm |
| h: | 2.0 cm | q: | 6.0 cm | z: | 5.5 cm |
| i: | 2.0 cm | r: | 4.0 cm | | |

Figure 31:
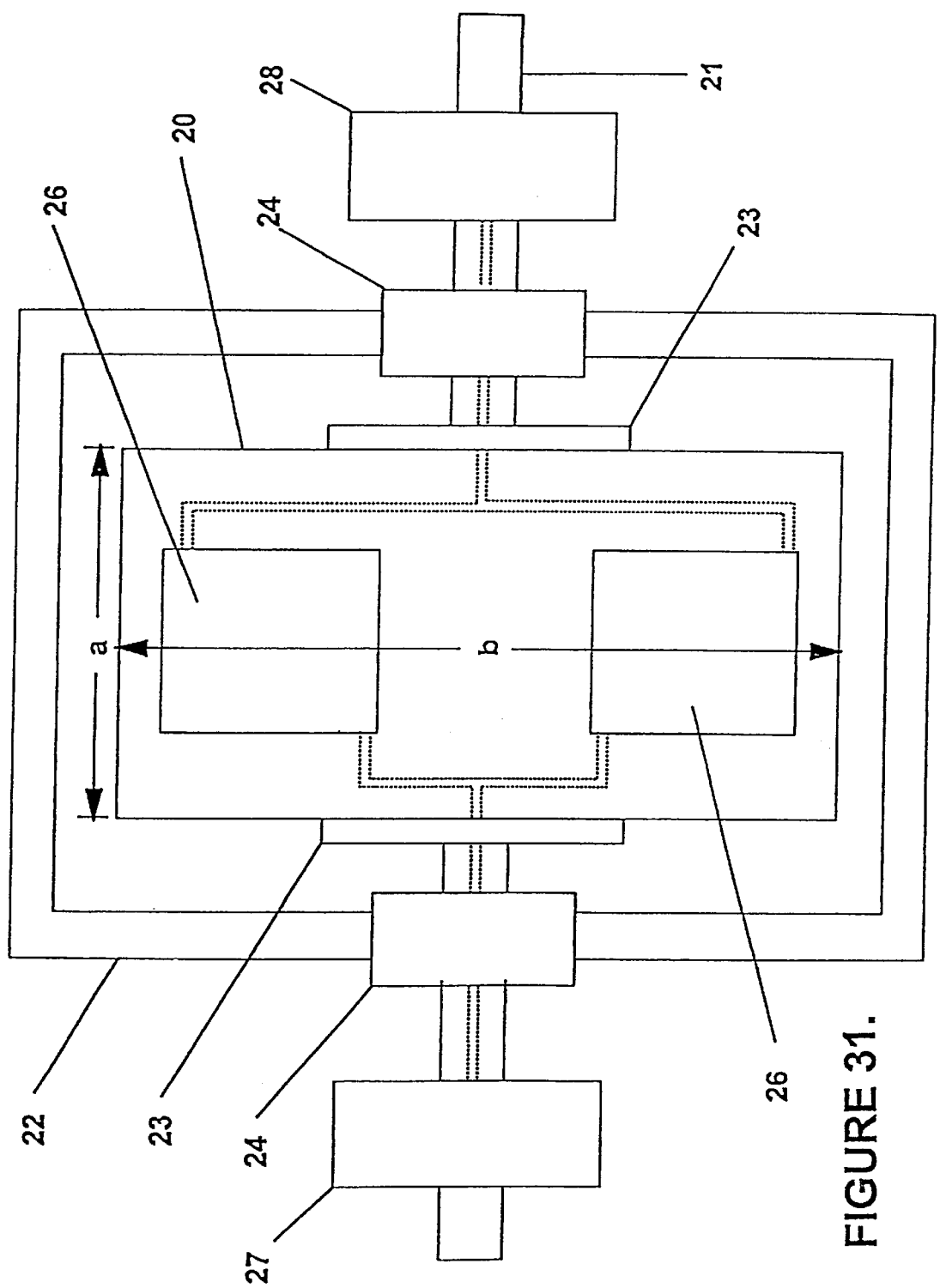
FIG. 31 is a sectional view of a second embodiment of the Centrifugal Fermentation Process when viewed parallel to the axis of rotation.

FIG. 31 depicts the components of a second embodiment of this invention. A cylindrical rotor body 20 is mounted on a horizontal, motor-driven rotating shaft 21 inside a safety containment chamber 22 bounded by metal walls. The rotor body 20 is fixed in position on the rotating shaft 21 by means of locking collars 23. The rotating shaft 21 is supported on either side of the rotor body 20 by bearings 24. The rotating shaft 21 extends outside the safety containment chamber 22 for a distance. Liquid flows are introduced into and removed from bioreactor chambers 26 in the rotor body 20 by means of a liquid input mechanical end-face seal 28 and a liquid output mechanical end-face seal 27. The liquid input mechanical end-face seal 28 communicates with a centrally-located axial liquid input channel (52 in FIG. 34) within the rotating shaft 21. The liquid output mechanical end-face seal 27 communicates with a centrally-located axial liquid output channel (51 in FIG. 34) within the rotating shaft 21. Typical dimensions for an example rotor body 20 (a=10 cm and b=36 cm) are entirely reasonable and comparable to rotor body dimensions known to those skilled in the art.

Figure 32:
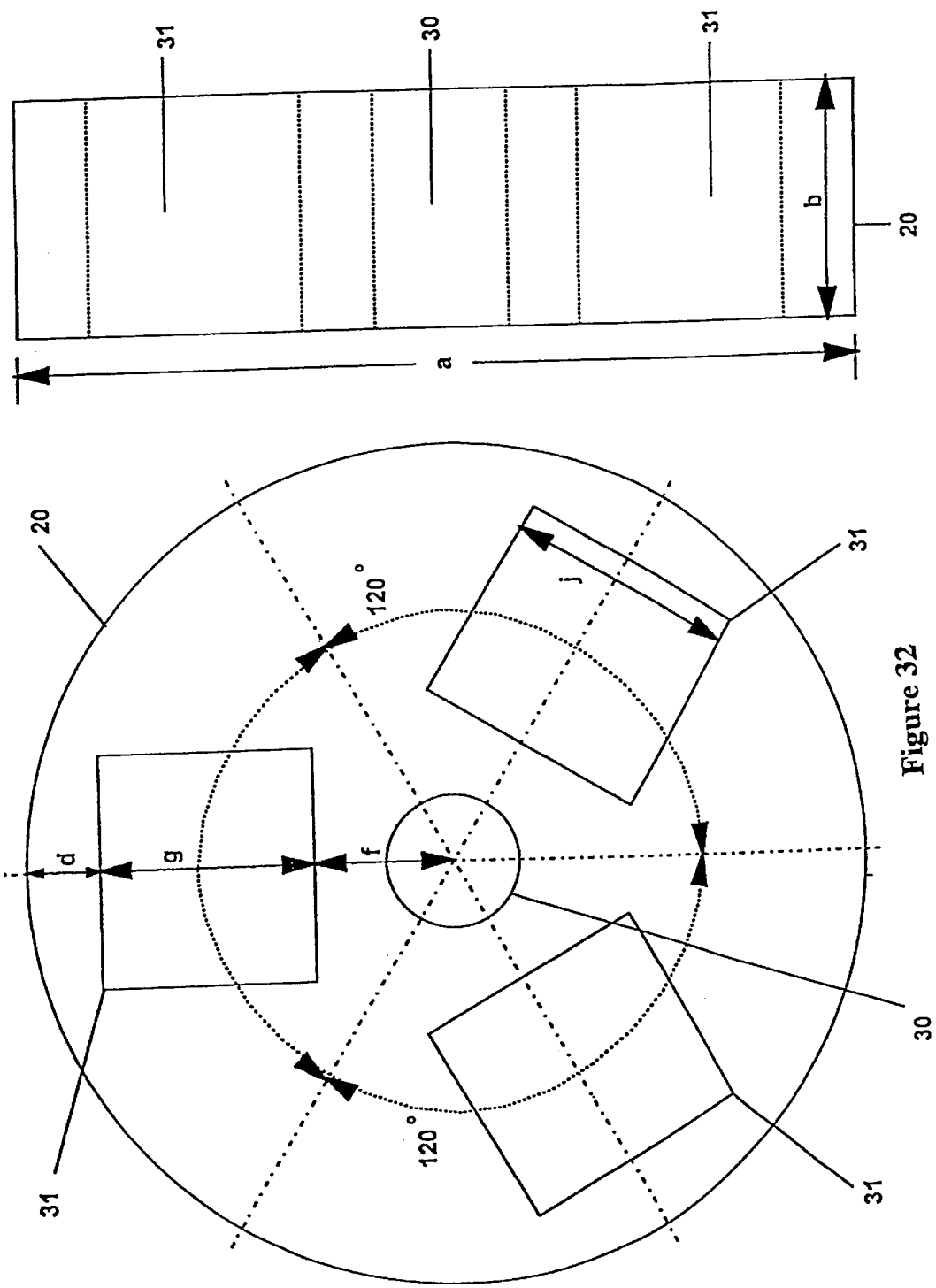
FIG. 32 are views of the rotor body of FIG. 31 when viewed parallel to the axis of rotation.

FIG. 32 shows two views of the rotor body 20 of FIG. 31. The rotor body 20 is machined with a shaft mounting channel 30 through its center to allow its mounting on the rotating shaft (21 in FIG. 31) and is machined to have mounting recesses 31 into which three rectangularly-faced demountable bioreactor chambers may be placed.

Figure 33:
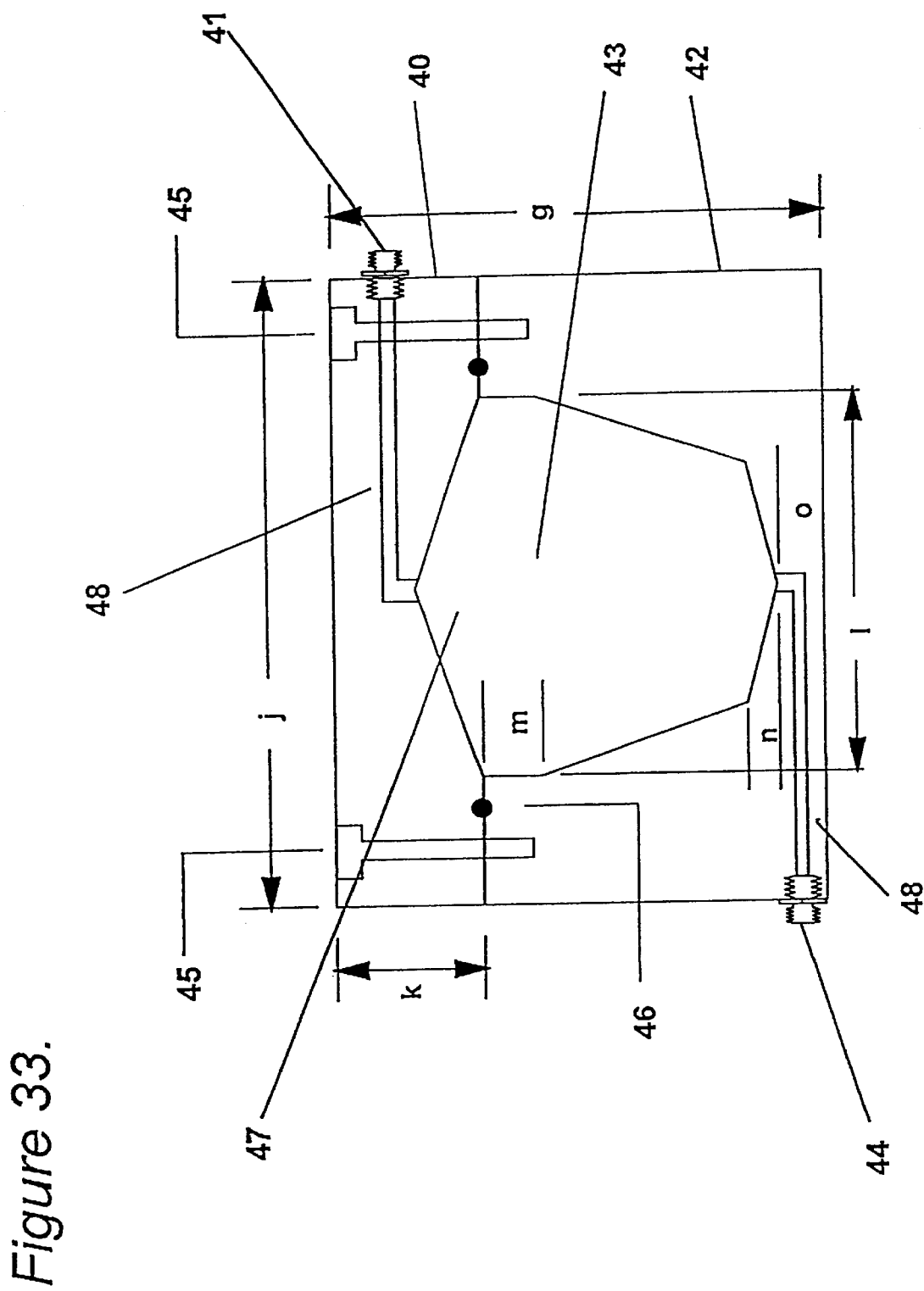
FIG. 33 is a cross-sectional view of one of the bioreactor chambers of FIG. 31.

FIG. 33 is a depiction of one of the bioreactor chambers of FIG. 31 (26 in FIG. 31). The bioreactor chamber (26 in FIG. 31) is rectilinear in section and is composed of a top piece 40 and a bottom piece 42 of thick-walled metal. The top piece 40 contains a machined conical recess 47 and a machined passage 48 terminating in an output compression fitting 41 by which liquid may be removed from the bioreactor chamber (26 in FIG. 31). The bottom piece 42 is made from the same metal as the top piece 40 and has been internally machined to form a biocatalyst immobilization chamber 43 of a desired geometric shape. The shape of the biocatalyst immobilization chamber 43 is that of a truncated cone with a short cylindrical volume at its top face and a short conical volume at its bottom face. A machined passage 48 terminating in an input compression fitting 44 allows liquid input into the biocatalyst immobilization chamber 43. The top piece 40 and the bottom piece 42 of the biocatalyst immobilization chamber 43 are bolted together by means of countersunk assembly screws 45 and sealed against an internal positive hydraulic pressure by means of one or more o-ring compression seals 46. In the case of certain animal cell cultures where contact between the immobilized cells and the interior metal walls of the biocatalyst immobilization chamber 43 should be avoided, it may be expedient to provide suitable conical inserts of, for example, polyethylene, in order to prevent such contact. Alternatively, the interior of the biocatalyst immobilization chamber 43 might be coated with an appropriate lining material to provide the same effect.

Figure 34:
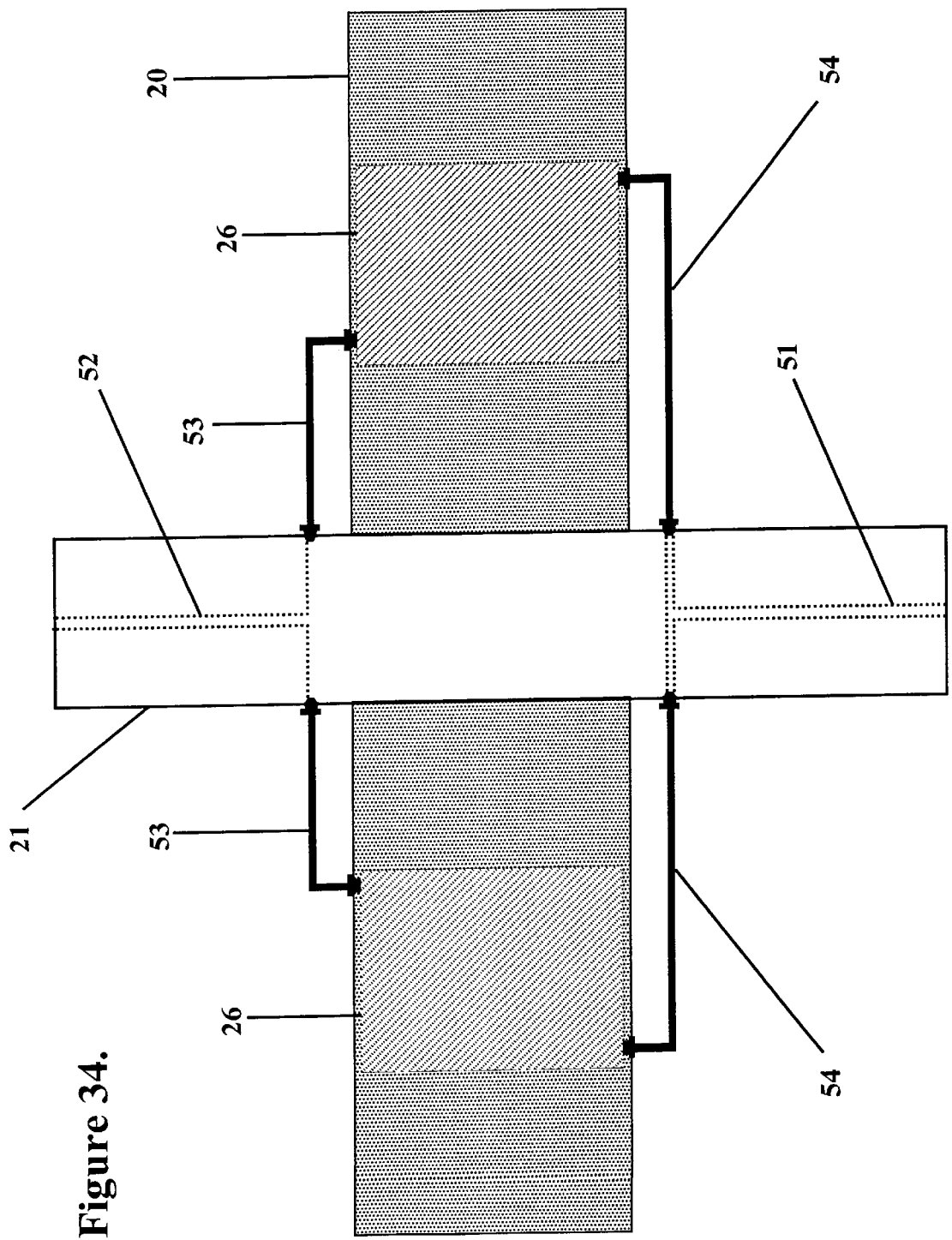
FIG. 34 is a sectional view of the rotor body of FIG. 31 when viewed perpendicular to the axis of rotation.

FIG. 34 is a transverse sectional view through the rotor body 20 of FIG. 31 and the rotating shaft 21 of FIG. 31 parallel to the axis of rotation. The output liquid transport lines 53 are metal tubes which communicate with the bioreactor chambers 26 and the centrally-located axial liquid output channel 51 through output compression fittings (41 in FIG. 33). The input liquid transport lines 54 are metal tubes which communicate with the bioreactor chambers 26 and the centrally-located axial liquid input channel 52 through input compression fittings (44 in FIG. 33).

Figure 35:
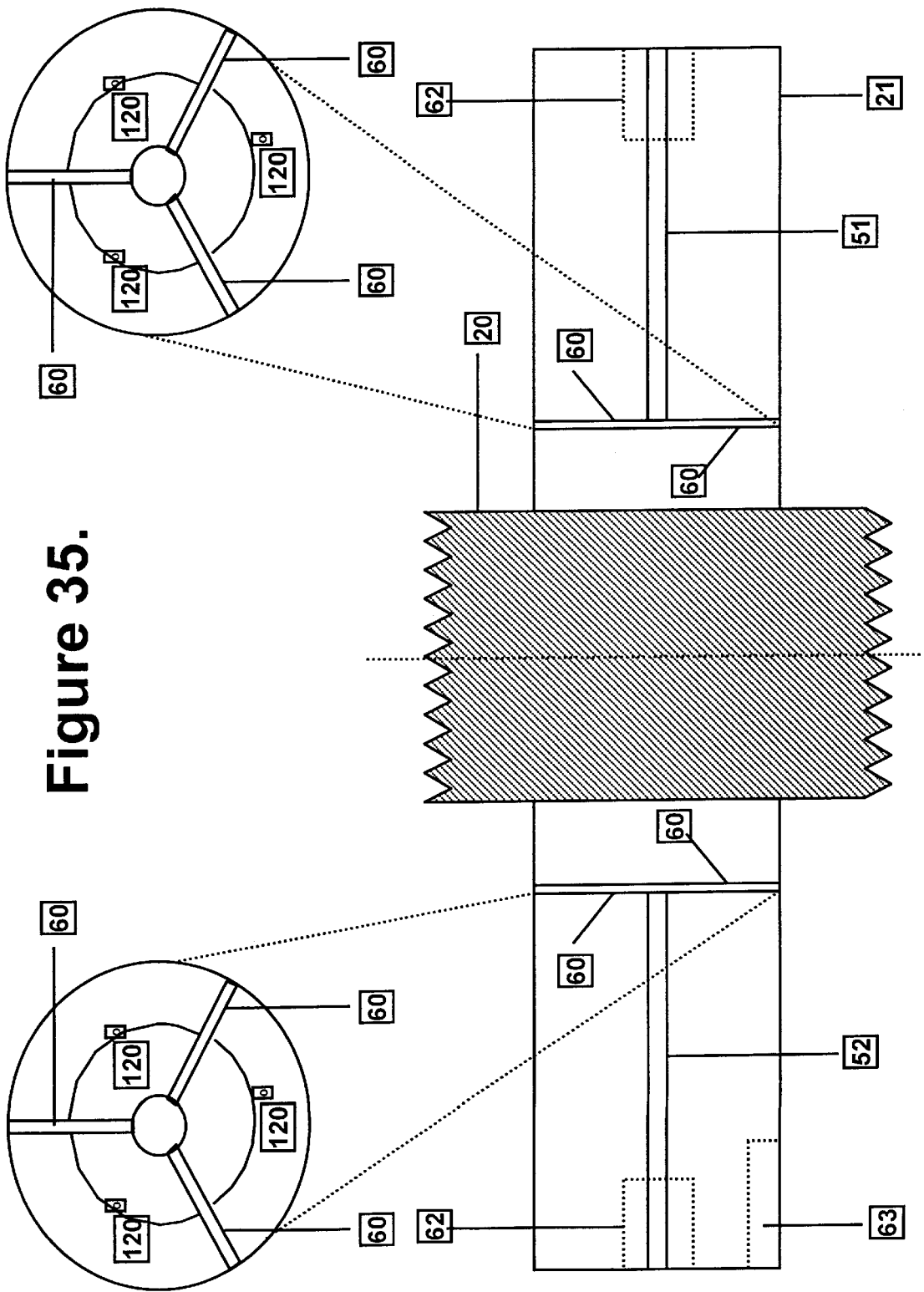
FIG. 35 is an illustration of the axial channels and their termini in the rotating shaft of FIG. 31.

FIG. 35 is a view of the rotating shaft 21 of FIG. 31 on which the rotor body 20, the liquid output mechanical end-face seal (27 in FIG. 31), and the liquid input mechanical end-face seal (28 in FIG. 31) are mounted. The rotating shaft 21 contains a centrally-located axial liquid output channel 51 and a centrally-located axial liquid input channel 52. The centrally-located axial liquid output channel 51 (typically ⅛" diameter) transports the liquid output of the bioreactor chambers (26 in FIG. 31) to the liquid output mechanical end-face seal (27 in FIG. 31) by means of three short radially-directed passages 60 while the centrally-located axial liquid input channel 52 (also ⅛" dia.) conveys liquid from the liquid input mechanical end-face seal (28 in FIG. 31) into the bioreactor chambers (26 in FIG. 31), also by means of three short radially-directed passages 61. The centrally-located axial liquid output channel 51 and the centrally-located axial liquid input channel 52 extend from each end of the rotating shaft 21 to the region where the rotor body 20 is located. Each end of the rotating shaft 21 has a threaded recess 62 which is formed to accept threaded liquid mechanical seals. The leftmost end of the rotating shaft 21 is also machined to provide a keyway 63 to which a motor drive pulley (not shown) may be attached.

Figure 36:
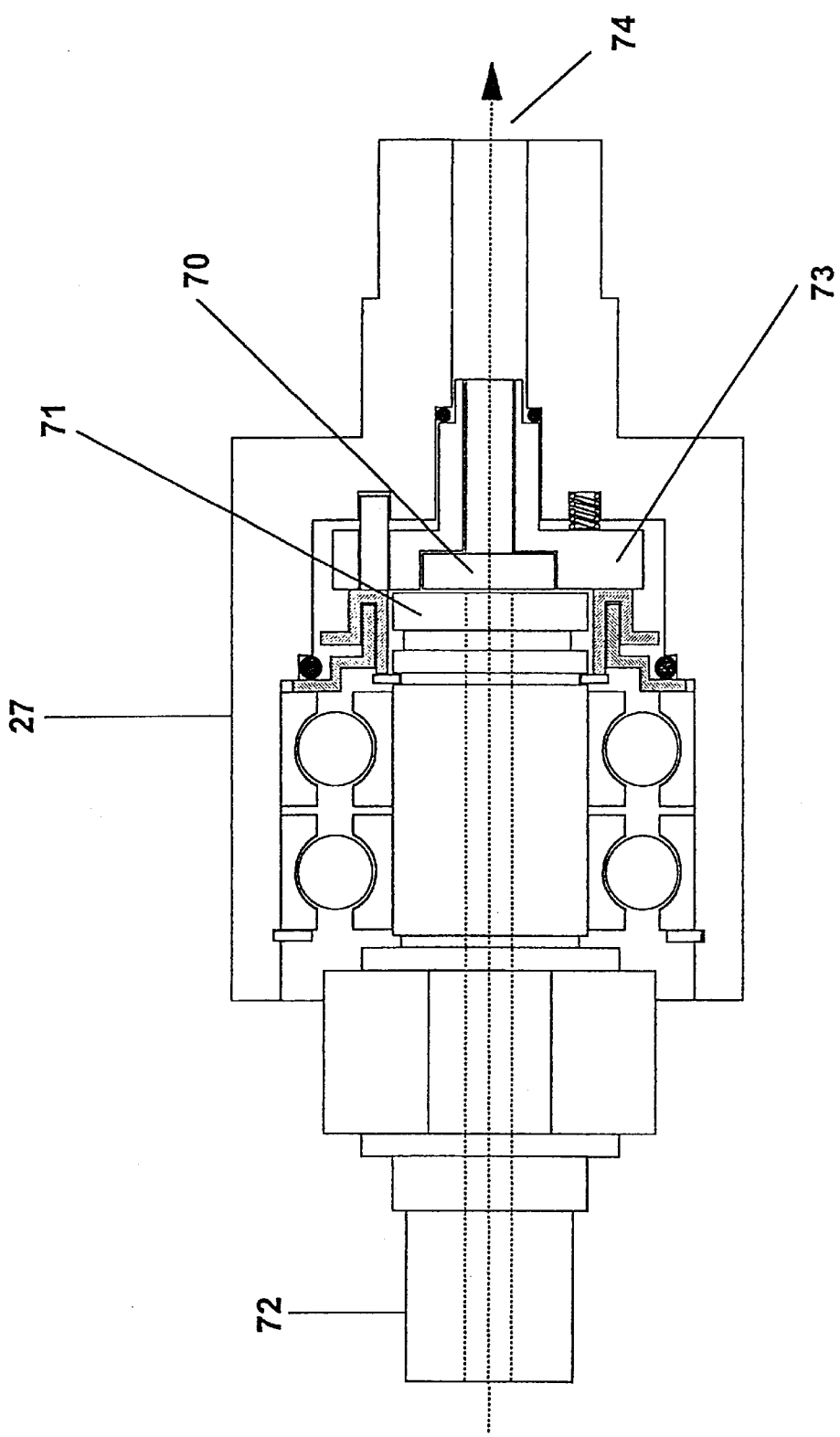
FIG. 36 is a sectional view of a representative high-performance end face seal.

FIG. 36 is a view of a typical liquid output mechanical end-face seal assembly such as the liquid output mechanical end-face seal 27, shown in FIG. 31. The rotating part 72 of the liquid output mechanical end-face seal 27 is threaded into the threaded recess (62 in FIG. 35) in the leftmost end of the rotating shaft (21 in FIG. 35). A seal between the rotating and stationary portions of the liquid output mechanical end-face seal 27 is provided by the contact of the stationary seal face 70 against the rotating seal face 71. In the case of high performance mechanical end-face seals utilizable in the process of this invention, where consideration must be made for the resultant centrifugal forces which act on the seal components, all spring elements are located in the stationary portion of the seal assembly. While the seal assembly shown in FIG. 36 is a single seal, double and/or tandem end-face seal configurations may prove more advantageous in prolonged usage. When such a seal assembly is mounted on the rotating shaft (21 in FIG. 34) of the present invention, aqueous liquids may be pumped out of the stationary part 73 of the liquid output mechanical end-face seal assembly via compression fittings and the pumped liquid will follow the path indicated by the dotted line 74 to make communication with the centrally-located axial liquid output channel (51 in FIG. 34) which transports the liquid away from the bioreactor chambers (26 in FIG. 34) mounted in the rotor body (20 in FIG. 34).

The principal disadvantage heretofore in the employment of mechanical seals for the transfer of liquids into and out of rotating systems, where the purpose of the system is to culture biological entities such as animal cells or microorganisms, has been the problem of the maintenance of sterility. Low pressure mechanical seals have, in the past, provided a route by which adventitious micro-organisms can gain entrance into bioreactor systems via the thin film of internal liquid which lubricates the end-face seal surfaces. In the process of this invention, where the internal liquid is always held at a hydraulic pressure higher than ambient, all leakage of liquid will occur to the exterior of the system; there is thus no possible route through which adventitious contaminants can enter the system.

In order to obtain data for an analysis of the performance of a rotor body (20 in FIG. 31) of the dimensions and configuration outlined in FIGS. 31–32 and 34–35 and containing demountable rectilinear biocatalyst immobilization chambers 43 like those depicted in FIG. 33, it was necessary that several scale dimensions and boundary equations be chosen arbitrarily and used to determine the operating characteristics of the second embodiment of the present invention. The immobilization boundary equations chosen are those listed in Equations 1 and 2 of FIG. 15. The rotor dimensions chosen for this example and indicated by letter in FIGS. 31–33 are as follows:

| | | | | | |
|---|---|---|---|---|---|
| a: | 10.0 cm | g: | 7.0 cm | m: | 0.5 cm |
| b: | 36.0 cm | j: | 10.0 cm | n: | 1.0 cm |
| d: | 4.0 cm | k: | 1.5 cm | o: | 1.0 cm |
| f: | 6.0 cm | L: | 7.0 cm | | |

In the first and second embodiments of this invention, described above, a portion of the geometry of the biocatalyst immobilization chamber (43 in FIGS. 21 and 33) is that of a truncated cone. As is shown in FIG. 37, the dimensional problem of determining the "aspect ratio" (the ratio of the small radius of the truncated cone 110 to the large radius of the truncated cone) of the biocatalyst immobilization chamber (43 in FIGS. 21 and 33) due to boundary condition constraints can be reduced to an examination of the geometrical relationships between the large and small radii of the truncated cone 110 and the height of the truncated cone 110.

FIG. 37A is a sectional view, through the plane of rotation, of the portion of the biocatalyst immobilization chamber (43 in FIGS. 21 and 33) which resembles a truncated cone 110. The truncated cone 110 has a proximal face which is located a distance of $R_x$ from the center of rotation. The truncated length of the cone is $R_c$. A Relative Centrifugal Force (RCF) acts to cause translation of a particle 111 in the biocatalyst immobilization chamber (43 in FIGS. 21 and 33) to longer radii, while liquid flow forces (FV) act to cause translation to shorter radii. Equation (1) of FIG. 37B is an expression for the magnitude of the Relative Centrifugal Force (RCF) at radial length ($R_x$) in terms of the Rotor Speed (RS). Equation (2) is an expression for the magnitude of the Flow Velocity (FV) at radial length ($R_x$) in terms of the liquid Flow Rate (FR) and the large radius (q) of the truncated cone 110. Equation (3) is an expression for the magnitude of the Relative Centrifugal Force (RCF) at radial length ($R_x + R_c$) in terms of the Rotor Speed (RS). Equation (4) is an expression for the magnitude of the Flow Velocity (FV), at radial length ($R_x + R_c$), in terms of the liquid Flow Rate (FR) and the given dimensions of the truncated cone 110 and its sections. In order to determine the "aspect ratio" of the truncated cone 110 which will satisfy certain boundary conditions, given the physical dimensions of the rotor body (20 in FIGS. 19 and 31), we have chosen to express the radius of the small end (R1) of the truncated cone 110 in terms of the length (L) of a non-truncated version of the truncated cone 110. This non-truncated version of the truncated cone 110 is shown in dotted lines in FIG. 37B.

The desired boundary conditions are: (1) that the product of the intrinsic Sedimentation Rate (SR) of the immobilized particle due to gravity and the applied centrifugal field (RCF) be exactly equal to the magnitude of the liquid flow forces (FV) at the most distal portion of the biocatalyst immobilization chamber (43 in FIGS. 21 and 33); and (2) that this product be twice the magnitude of the liquid flow forces (FV) at the most proximal portion of the biocatalyst immobilization chamber (43 in FIGS. 21 and 33). Thus:

at centrifugal radius=$R_x+R_c$(SR)×(RCF)=FV at centrifugal radius=$R_x$(SR)×(RCF)=2×FV Substituting into these equations the dimensional specifications for RCF and FV obtained from Eqns. (1–4) of FIG. 37, we now have two simultaneous equations which relate the liquid Flow Rate (FR), the Rotor Speed (RS), and the dimensions of the biocatalyst immobilization chamber (43 in FIGS. 21 and 33):

$$(1) \quad (SR)\, C_1(R_X + R_C) = C_2 \left(\frac{L}{L - R_C}\right)^2$$

$$(SR)C_1(R_x) = 2 \times C_2 \quad (2)$$

In order to arrive at a solution to these equations, we will make the following substitutions which are based on the physical dimensional limits of the example rotor system:

$R_x$=90 mm $R_c$=30 mm $q$=30 mm

The simultaneous equations now become:

$$(1) \quad (SR)\, C_1(120) = C_2 \left(\frac{L}{L - 30}\right)^2$$

$$(SR)C_1(R_x) = 2 \times C_2 \quad (2)$$

Substituting Eqn. (2) into Eqn. (1) yields:

$$\left(\frac{L}{L-30}\right)^2 = 240/90$$

Solution of this quadratic expression yields L=77.4 mm and:

$$\left(\frac{L}{L-30}\right)^2 = 2.67$$

Since it was earlier determined (see FIG. 37) that:

$$R_1 = \frac{q(L - R_c)}{L}$$

Thus, the smaller radius of the truncated cone which satisfies the boundary conditions is:

$R_1$=18.4 mm

Now, the two simultaneous equations become:

$(SR)C_1(120)=C_2(2.67)$ (1)

$(SR)C_1(90)=C_2(2)$ (2)

and, by subtracting (2) from (1) and collecting terms, we arrive at:

$(SR)(30)C_1=(0.67)C_2$ (3)

Substitution into (3) of the values of $C_1$ and $C_2$ yields:

$$(3) \quad (SR)\, (30)\, (1.12) \left(\frac{RPM}{1000}\right)^2 = (0.67)\left(\frac{FR}{\pi \cdot q^2}\right)$$

Now we have an expression which satisfies the desired boundary conditions and physical dimensional constraints in terms of the controllable variables, RS and FR:

$\sqrt{SR}(RPM)=(2.65)\sqrt{FR}$

Thus, once the physical dimensions of the rotor system as well as those of the biocatalyst immobilization chamber have been determined, the range of Rotor Speeds (RS) and the system liquid Flow Rates (FR) which will constrain the particles to immobility in the bioreactor will follow a simple relationship which is dependent only on the intrinsic Sedimentation Rate (SR) of the object particle due to gravity. Note that, under the above conditions, the maximal volume of immobilization is ca. 56 mL per bioreactor chamber.

This method and apparatus for containing a biocatalyst comprises the step of containing the biocatalyst in a bioreactor chamber placed in a centrifugal force field where the centrifugal force field is oriented in a plane parallel to the plane in which the force of gravity acts. The centrifugal force field is diametrically opposed by a continuously flowing liquid at hydraulic pressures greater than the ambient barometric pressure.

Figure 45:
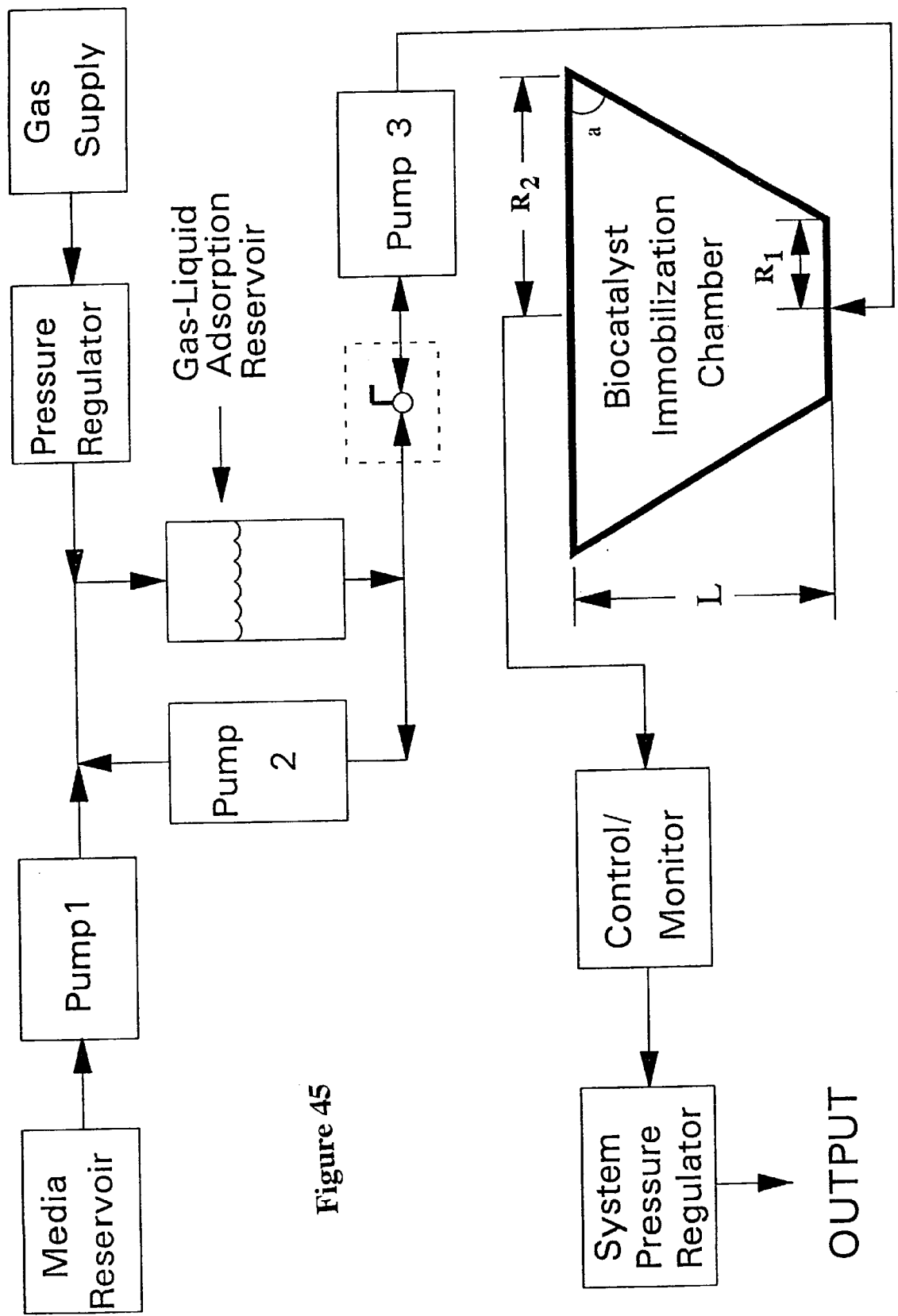
FIG. 45 is an embodiment which may be employed for applications where the immobilized biocatalyst is in a complex consisting of a support particle to which the biocatalyst is attached.

FIG. 45 depicts the components of a third embodiment of this invention. This embodiment is a design which may be employed for applications where the immobilized biocatalyst is in a complex consisting of a dense inert support particle to which the actual biocatalyst is attached. In such an application, the buoyant force acting on the biocatalyst/support complex as a result of nutrient liquid flow can be negated, and thus immobilizing the biocatalyst/support complex, by the vertical alignment of the biocatalyst immobilization chamber so that the earth's gravitational field acts on the biocatalyst/support complex to provide the required counter-acting force. Further, the range of flow rates which can be accommodated in this system is in no way limited since the buoyant force which must be countered is the nutrient liquid flow velocity. The magnitude of the flow velocity can be varied through a desired range by varying the cross-sectional diameters and the aspect ratio of those diameters as necessary. The relative centrifugal field in this case is close to 1×g (that provided by the earth's gravitational field). Thus, the required applied centrifugal field, in this case, is zero.

In the embodiment shown in FIG. 45, nutrient liquids, which have been pressurized and have dissolved in this liquid the appropriate quantities of a nutrient which is gaseous at ambient pressure, are pumped into a stationary biocatalyst immobilization chamber fed by the main feed pump, Pump 3. The continuation of the liquid flow as it exits the biocatalyst immobilization chamber is fed through control and monitoring sensors and through a system pressure regulator which maintains the elevated hydraulic pressure of the system. The ratio of $R_1$ to $R_2$ is dependent on the desired flow velocity boundary conditions and can vary downward from 1.0 to any desired fraction thereof. $R_1$ is not limited in dimension: its magnitude is determined by the size of the liquid flow rate which is desired. L, the height of the immobilization chamber, is not limited in dimension: its magnitude is determined by the desired retention time of a nutrient liquid bolus as it passes through the biocatalyst immobilization chamber.

In order to obtain data for an analysis of the performance of a biocatalyst immobilization chamber of the embodiment in FIG. 45, (dimensions denoted by letters), it was necessary that several scale dimensions and boundary equations be chosen arbitrarily and used to determine the operating characteristics of an embodiment of the present invention. The immobilization boundary equations (both the top and bottom boundary equation) chosen is that listed in Equation 1 of FIG. 15. The biocatalyst immobilization chamber dimensions chosen for this example and indicated by letter in FIG. 45 are as follows:

$R_1$:5.0 cm $R_2$:5.1 cm

L:61.0 cm

A biocatalyst immobilization chamber of the above dimensions was loaded with 100 mL of 30–50 mesh peanut shell charcoal (density: ca. 3.5 gm/mL). The system configuration of FIG. 45 was established and, at a liquid flow rate of 120 mL/min, an equilibrium between the flow velocity-derived buoyant forces and the intrinsic sedimentation rate of the individual charcoal particles at 1×g relative gravitational field resulted in a stable, immobilized, three-dimensional array. Note that small flow rate variations near the nominal value chosen resulted in small increases or decreases in the immobilized array density and volume, while large changes in flow rate require that $R_1$, $R_2$, and L be changed, thus requiring separate biocatalyst immobilization chamber sizes to accommodate different flow rate regimes. While the charcoal particles were found suitable for the attachment of a number of bacterial genera, the type of inert particle employed for a specific biocatalyst immobilization purpose are limited only in the compatability with the biocatalyst and the liquid environment of the system.

There are many alternative shapes for the biocatalyst immobilization chambers which are contemplated in this invention. One such alternative embodiment is a biocatalyst immobilization chamber having its inner space in the shape of a right circular cone with a major axis which is aligned parallel to the applied centrifugal force field and which has a large diameter which is nearer to the axis of rotation than is its apex.

Another alternative embodiment is a biocatalyst immobilization chamber having its inner space in the shape of a right circular cone which has a major axis which forms an angle of between 0 and 90 degrees with the applied centrifugal force field. Also included in the present invention is a biocatalyst immobilization chamber having its inner space in the shape of a truncated right circular cone which has a major axis which is aligned parallel to the applied centrifugal force field and which has a large diameter which is nearer to the axis of rotation than is its minor diameter.

Additionally, the present invention includes a biocatalyst immobilization chamber having its inner space in the shape of a truncated right circular cone which has a major axis which forms an angle of between 0 and 90 degrees with the applied centrifugal force field.

The present invention includes a biocatalyst immobilization chamber having its inner space in the shape of a sphere where the applied centrifugal force field is perpendicular to a circular cross-section of the spherical biocatalyst immobilization chamber.

The present invention also includes a biocatalyst immobilization chamber having its inner space in the shape of a sphere where the applied centrifugal force field forms an angle of between 0 and 90 degrees with the circular cross-section.

Additionally, the present invention includes a biocatalyst immobilization chamber having its inner space is in the shape of a truncated sphere where the applied centrifugal force field is perpendicular to a circular cross-section of the sphere.

The present invention also includes a biocatalyst immobilization chamber having its inner space in the shape of a truncated sphere where the applied centrifugal force field forms an angle of between 0 and 90 degrees with the circular cross-section.

The present invention includes a biocatalyst immobilization chamber having its inner space in a shape which possesses a varying circular cross-section where the applied centrifugal force field is perpendicular to the circular cross-sections.

The present invention also includes a biocatalyst immobilization chamber having its inner space in a shape which possesses a varying circular cross-section where the applied centrifugal force field forms an angle of between 0 and 90 degrees with the circular cross-sections.

Additionally, the present invention includes a biocatalyst immobilization chamber having its inner space in a shape which possesses a varying elliptical cross-section where the applied centrifugal force field is perpendicular to the elliptical cross-sections.

The present invention also includes a biocatalyst immobilization chamber having its inner space in a shape which possesses a varying elliptical cross-section where the applied centrifugal force field forms an angle of between 0 and 90 degrees with the elliptical cross-sections.

Also included in present invention is a biocatalyst immobilization chamber having its inner space in a shape which is a combination of circular and elliptical cross-sections along an axis perpendicular to the applied centrifugal force field.

The present invention also includes a biocatalyst immobilization chamber having its inner space in a shape which is a combination of circular and elliptical cross-sections along an axis which forms an angle of between 0 and 90 degrees to the circular and/or elliptical cross-sections.

The process of this invention is directed toward the immobilization of biocatalysts such as micro-organisms and eukaryotic cells, their subcellular organelles, and natural or artificial aggregates of such biocatalysts. Thus, the process system must be capable of immobilizing fairly light particles. It is known that the sedimentation rates of such particles due to gravity range from ca. 0.01 mm/min for small bacteria to 0.1 mm/min for small animal cells to more than 10.0 mm/min for thick-walled micro-organisms (such as yeasts) and biocatalytic aggregates such as bead-immobilized cells. We have analyzed the performance characteristics of the centrifugal bioreactor system of this invention using the dimensional configurations outlined above and present these results below.

Figure 38:
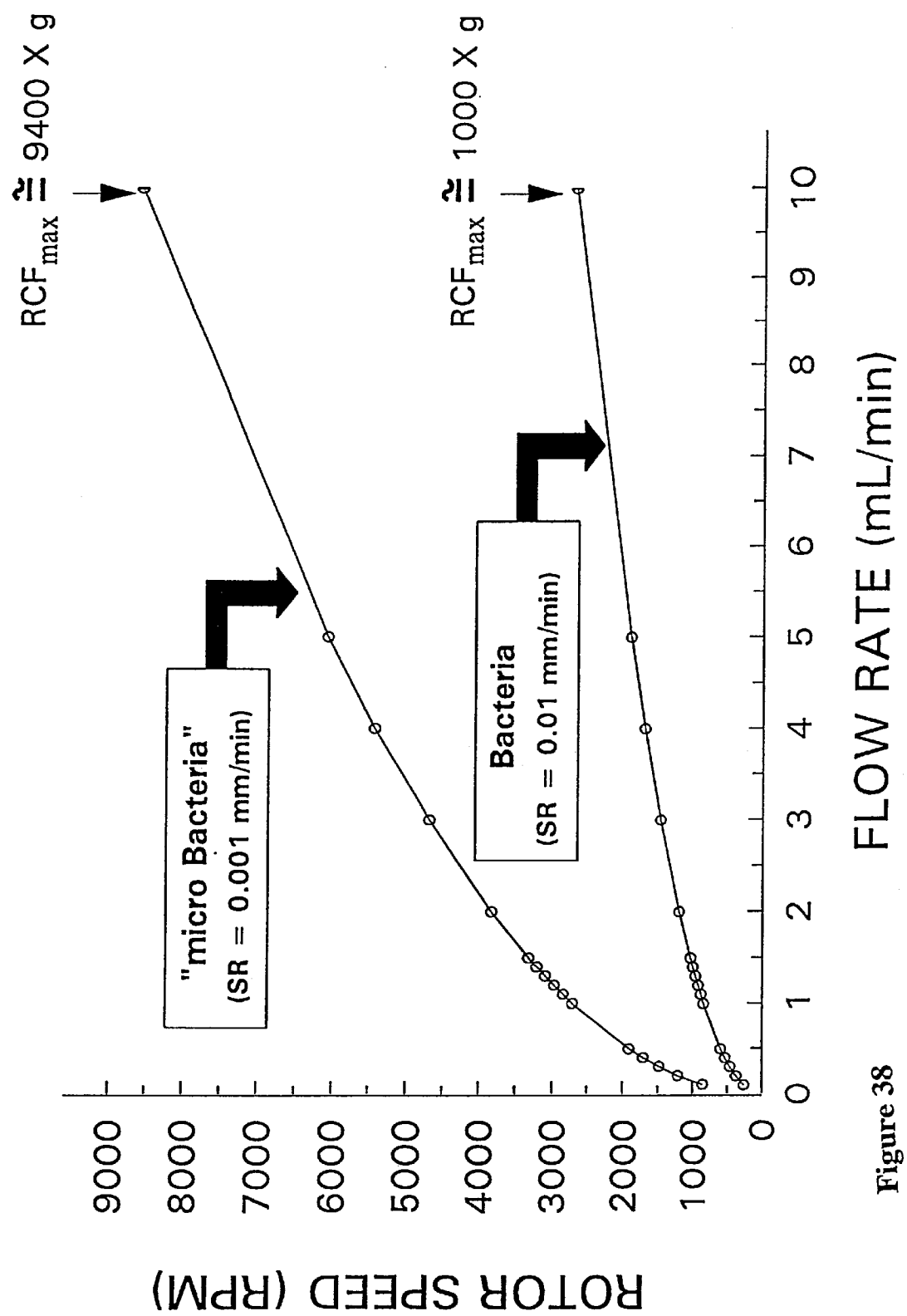
FIG. 38 is a graph relating the flow rates and rotor speeds which provide for particle immobilization under the dimensional and boundary condition constraints shown on FIG. 15 and for the rotor body of FIGS. 19 and 31. for particles of sedimentation rates of 0.001 and 0.01 mm/min at flow rates up to 10 mL/min.

FIG. 38 displays profiles of the values of rotor speed and liquid flow rate which satisfy the boundary conditions outlined earlier for the rotor and bioreactor dimensions outlined in FIGS. 19–29 (for the first embodiment of the present invention), and in FIGS. 31–35 (for the second embodiment of the present invention) for typical biologically significant particles of the lowest two Sedimentation Rate (SR) ranges. The upper line displays the continuum of liquid flow rates and rotor speeds which result in the immobilization of particles of an intrinsic Sedimentation Rate (SR) of 0.001 mm/min, a value smaller by a factor of ten than any we have measured for any tested micro-organism. Note that, even at a flow rate of 10 mL/min, the rotor speed required to maintain immobilization is a physically reasonable value and that the maximum centrifugal force (RCF) required is ca. 9400×g, a value well within the physical limits of average quality centrifugal systems. The lower line displays the corresponding profile for particles of a Sedimentation Rate (SR) of 0.01 mm/min, a value near that exhibited by typical representative bacteria. Again, this line represents a continuum of values which satisfy the immobilization conditions. Thus for example, if a flow rate of 2.0 mL/min is required to adequately nutrition a particular sized three-dimensional array of "bacteria A," a rotor speed near 1200 rpm will suffice, while a required flow rate of 8.0 mL/min necessitates a rotor speed near 2500 rpm. Note that the heavier particles of SR=0.01 mm/min require only a modest maximal centrifugal force of ca. 1000×g at a flow rate of 10.0 mL/min.

Figure 39:
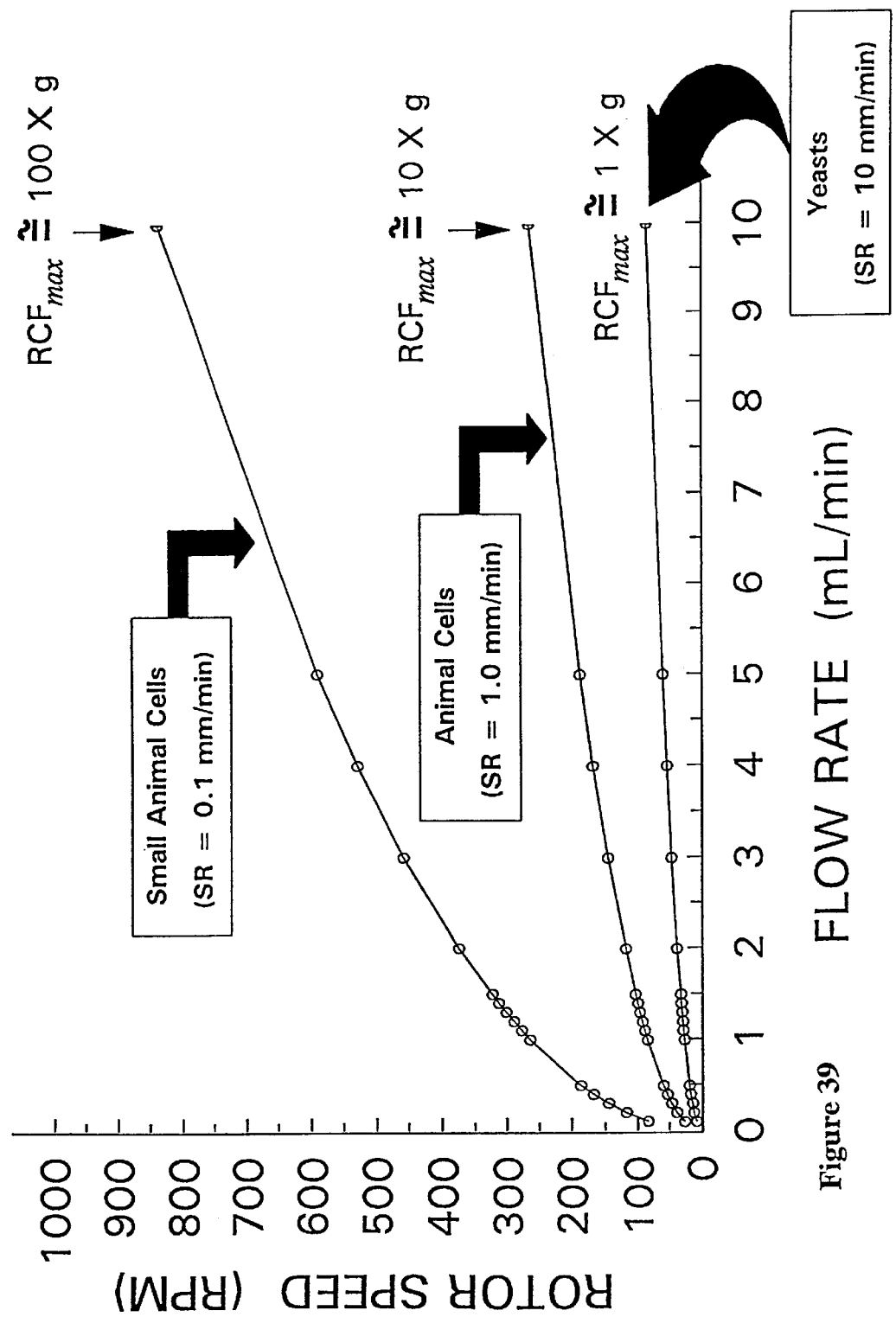
FIG. 39 is a graph relating the flow rates and rotor speeds which provide for particle immobilization under the dimensional and boundary condition constraints shown on FIG. 15 and for the rotor body of FIGS. 19 and 31 for particles of sedimentation rates of 0.1, 1.0, and 10.0 mm/min at flow rates up to 10 mL/min.

FIG. 39 displays profiles of the values of rotor speed and liquid flow rate which satisfy the boundary conditions outlined earlier for the rotor and bioreactor dimensions outlined in FIGS. 19–29 and 31–35 in the cases of typical biologically significant particles of the higher three Sedimentation Rate (SR) ranges. The upper line displays the continuum of liquid flow rates and rotor speeds which result in the immobilization of particles comparable to larger micro-organisms or small animal cells (for example, mammalian erythrocytes) of an intrinsic Sedimentation Rate (SR) of 0.1 mm/min. The middle line displays the corresponding values for the immobilization of more typical animal cells (ca. 30 $\mu$m diameter; SR=1.0 mm/min), while the bottom line displays the continuum of values which provide for the immobilization of large dense cells, such as eukaryotic yeasts (SR=10 mm/min). As was the trend shown in FIG. 38, it is obvious from the data of FIG. 39 that the maximum rotor speeds and maximal centrifugal forces required in this flow rate range decrease as the intrinsic particle Sedimentation Rate (SR) due to gravity increases. Thus, for a flow rate of 10.0 mL/min, a three-dimensional array of average-sized animal cells requires only a relative centrifugal force of ca. 10×g to provide immobilization.

Figure 40:
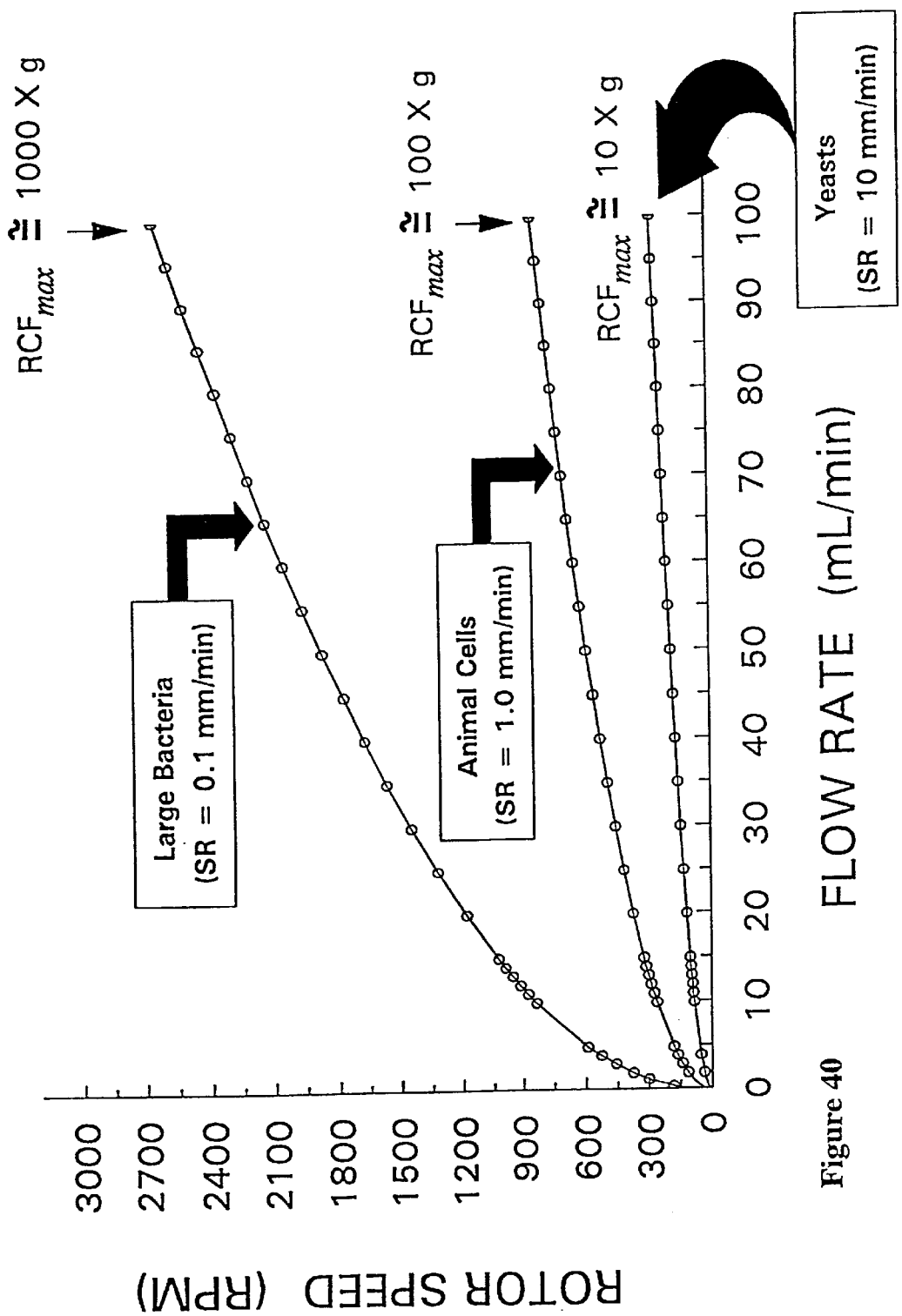
FIG. 40 is a graph relating the flow rates and rotor speeds which provide for particle immobilization under the dimensional and boundary condition constraints shown on FIG. 15 and for the rotor body of FIGS. 19 and 31 for particles of sedimentation rates of 0.1, 1.0, and 10.0 mm/min at flow rates up to 100 mL/min.

FIG. 40 displays profiles of the values of rotor speed and liquid flow rate which satisfy the boundary conditions outlined earlier for the rotor and bioreactor dimensions outlined in FIGS. 19–29 and FIGS. 31–35 in the case of liquid flow rates of as much as 100 mL/min for the highest three intrinsic Sedimentation Rate (SR) ranges examined. Thus, even if the liquid flow rates required to nutrition such immobilized "beds" of particles (example bed volume=56 mL) is increased ten-fold, the maximal centrifugal forces and rotor speeds required are technically unremarkable. Note that, in the case of "animal cells" (SR=1.0 mm/min) a flow rate of 100 mL/min represents a flow of 6.0 L/hr, a flow obviously larger than that required to adequately nutrition such a three-dimensional array of cells under any imaginable conditions.

While it is generally obvious that the effect of immobilizing a population of, for example, bacteria in a flowing liquid will not lead to cellular damage as a result of the flow of liquid past the surface of such cells (since many micro-organisms possess extracellular "sheaths" which protect their plasma membranes from liquid shear forces), it is less obvious whether delicate animal cells (which do not possess such extracellular protection) would remain viable under these conditions. However, as was shown in FIG. 39, the maximum Relative Centrifugal Force (RCF) required to maintain an average-sized animal cell immobile in a liquid flow of 10 mL/min is ca. 10×g. Even if this flow is raised to a level decidedly well above any anticipated nutritional need (100 mL/min), the maximum RCF required is only ca. 100×g (FIG. 40). It should be remembered that the immobilization of such a cell in a flowing liquid is the mathematical equivalent of moving the cell through a stationary liquid. Thus, since the conventional laboratory sedimentation of animal cells through liquid media at RCF's of more than 100×g is an unremarkable phenomenon, it is unlikely that the shear forces acting on such cells in the process of this invention will cause any damage to their plasma membranes. This assertion is supported by the operating characteristics of a related device, the Beckman JE-5.0 Centrifugal Elutriation System, from which viable animal cells have been successfully recovered after exposure to flow rates and RCF's greatly in excess of those proposed herein for the process of this invention.

With the present invention, it is possible to immobilize three-dimensional arrays of biologically-significant particles and to adequately nutrition the immobilized particles with a completely liquid flow. In particular, for the small-scale prototypic centrifugal process outlined above, the required centrifugal forces and liquid flow rates are not unusual and present no novel problems such as, for example, requiring unreasonably high rotational speeds or flow rates. Further, it has been demonstrated that there is a wide range of paired flow rate and angular velocity values which maintain the immobilization of three-dimensional arrays of such particles.

The fact that there is a wide range of flow rates and corresponding rotational speeds which can be used to immobilize such arrays of particles has, however, a wider significance. Using conventional culture methodology, the major problem encountered in large-scale culture is the inability to adequately nutrition dense masses of metabolically-active biological units. In the case of conventional mammalian cell culture for example, an average cell density of more than $1 \times 10^6$ cells/mL is rarely achieved for prolonged time periods for this reason. Similarly, bacterial cell densities between $1 \times 10^7$ and $1 \times 10^9$ cells/mL are rarely exceeded in mass culture by conventional methods for this same reason. Using the methodology of the process of this invention, as cell density and effective "bed" volume increases (either from cellular proliferation or bioreactor loading), the increased nutritional requirements of larger or more dense cultures can be met by increasing input liquid flow while simultaneously increasing the size of the applied centrifugal field. Using the process of this invention, it is possible to easily maintain mammalian cell cultures at concentrations two powers of ten greater than conventional, with bacterial cell densities approaching between $1 \times 10^{10}$ and $1 \times 10^{11}$ cells/mL equally realizable.

Similarly, for dense cultures of aerobic organisms, the conventional problem of adequate delivery of optimal dissolved oxygen to the culture is easily solved using the process of this invention. Since it is possible to dissolve molecular oxygen in typical culture media at concentrations of more than 100 mM (using a hydraulic pressure of ca. 1500 psig) the problem of the delivery of optimal dissolved oxygen, for any imaginable dense culture, is solved simply by adjusting the system hydraulic pressure to a value which will maintain the solubility of the desired concentration of oxygen. The ability to maintain dissolved oxygen concentration at optimal levels results in greatly increased production efficiency. As has been noted by many researchers, the inability to achieve cellular production efficiencies near those observed in vivo is a major disadvantage of conventional animal culture techniques (The Scientist, 8, #22, pg.16, Nov. 14, 1994).

The ability to achieve near-normal aerobic efficiency in dense culture has another, less obvious, advantage; the generation of heat. Instead of requiring expensive energy input to bring the liquid cellular environment to an optimal temperature, it is likely that the pumped liquid of the process of this invention will have to be delivered to the cellular environment at reduced temperatures in order to carry away excess metabolic heat.

Another important advantage of the process of this invention is the relative invariance of the chemical composition of the liquid environment in which the three-dimensional arrays of biocatalysts are immobilized. Since the arrays are continually presented with fresh, optimal liquid nutrient input and since these arrays are continually drained by the continuance of the process flow, the chemical composition of the cellular environment will be completely invariant in time. There will be shallow chemical gradients of nutrients, product(s), and metabolites across the radial length of these arrays, but since the radial length is the shortest dimension of the array, these gradients will be minimal and can be easily compensated for by tailoring the media composition. Thus, for example, a pH change across the array depth can be compensated for with minimal buffering while input nutrient gradients across the array depth can be similarly compensated for.

The most important advantage of the process of the present invention, however, is the fact that metabolic waste products will be continually removed from the cellular environments by the liquid process flow. Since it has been suggested that the inability to remove metabolic wastes and the inability to continually remove desired products from the cellular environment is a major factor in lowered per-cell productivity, it is likely that the utilization of the process of this invention will markedly increase general cellular productivity.

The chemical composition of optimal input liquid nutrient media to immobilized populations of biocatalysts in the process of this invention will be quite different from that of conventional nutrient media. In particular, the optimal media composition in this process will be that which can be completely consumed in one pass through the bioreactor chamber. Typical nutrient media contain a mix of as many as thirty or more nutrient chemicals, all of which are present in amounts which greatly exceed the nutritional needs of the biocatalysts. This is because the nutrient media must sustain their metabolic processes for as long as 100 hours in some cases. Similarly, conventional media contain concentrations of pH buffer compounds and indicators and hormonal stimuli (fetal sera and/or cytokines, etc.) in amounts which greatly exceed the immediate needs of the biocatalysts. In the process of this invention, the input liquid medium can be tailored to contain those concentrations of nutrients and stimulants which are directly required by the immediate metabolism of the immobilized biocatalysts. Ideally, the outflowing liquid which exits the bioreactor would be completely devoid of nutrients and contain only salts, metabolic wastes, and product molecules. The present invention makes it possible to tailor the input media in order to maintain an immobilized cellular population in a nutritional state which either promotes or inhibits cellular proliferation. It is highly unlikely that a nutritional mix which is optimal for cellular division is optimal for the production of biochemicals by cells at rest in the cell cycle.

The liquid medium used in the present invention may be any formulation known to those skilled in the art or may include specific individual components which are necessary for the biocatalyst of interest. The kinds of media may include, but are not limited to, a nutrient medium, a balanced salt solution, or a medium containing one or more organic solvents. The medium may contain dissolved gases for growth of the biocatalyst under anaerobic or aerobic conditions. The medium may be formulated so that the biocatalyst product or mobile biocatalysts found in the medium are more easily isolated.

Figure 41:
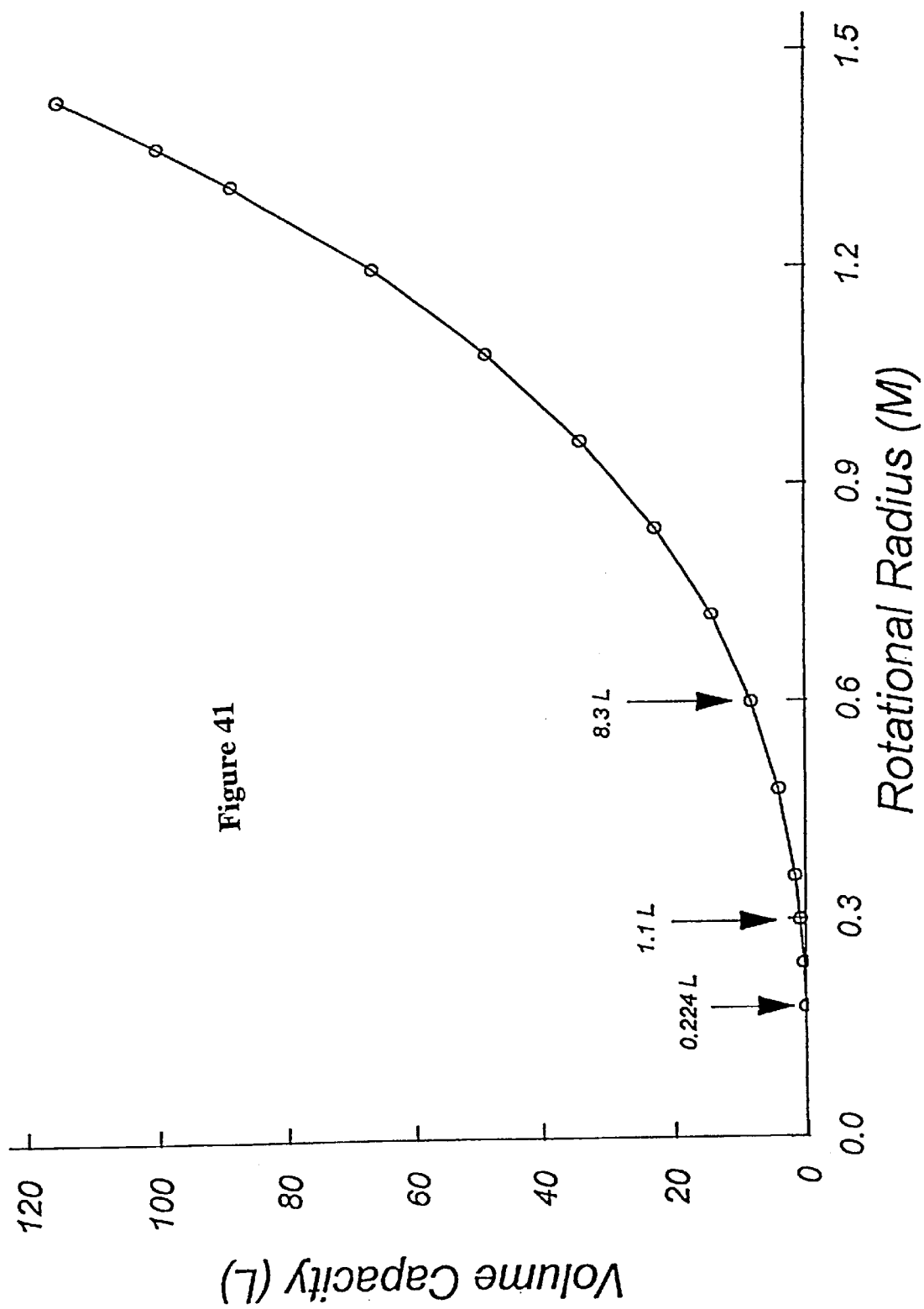
FIG. 41 is a graph displaying the relationship between rotor size and volume capacity in a first embodiment of this invention.
Figure 42:
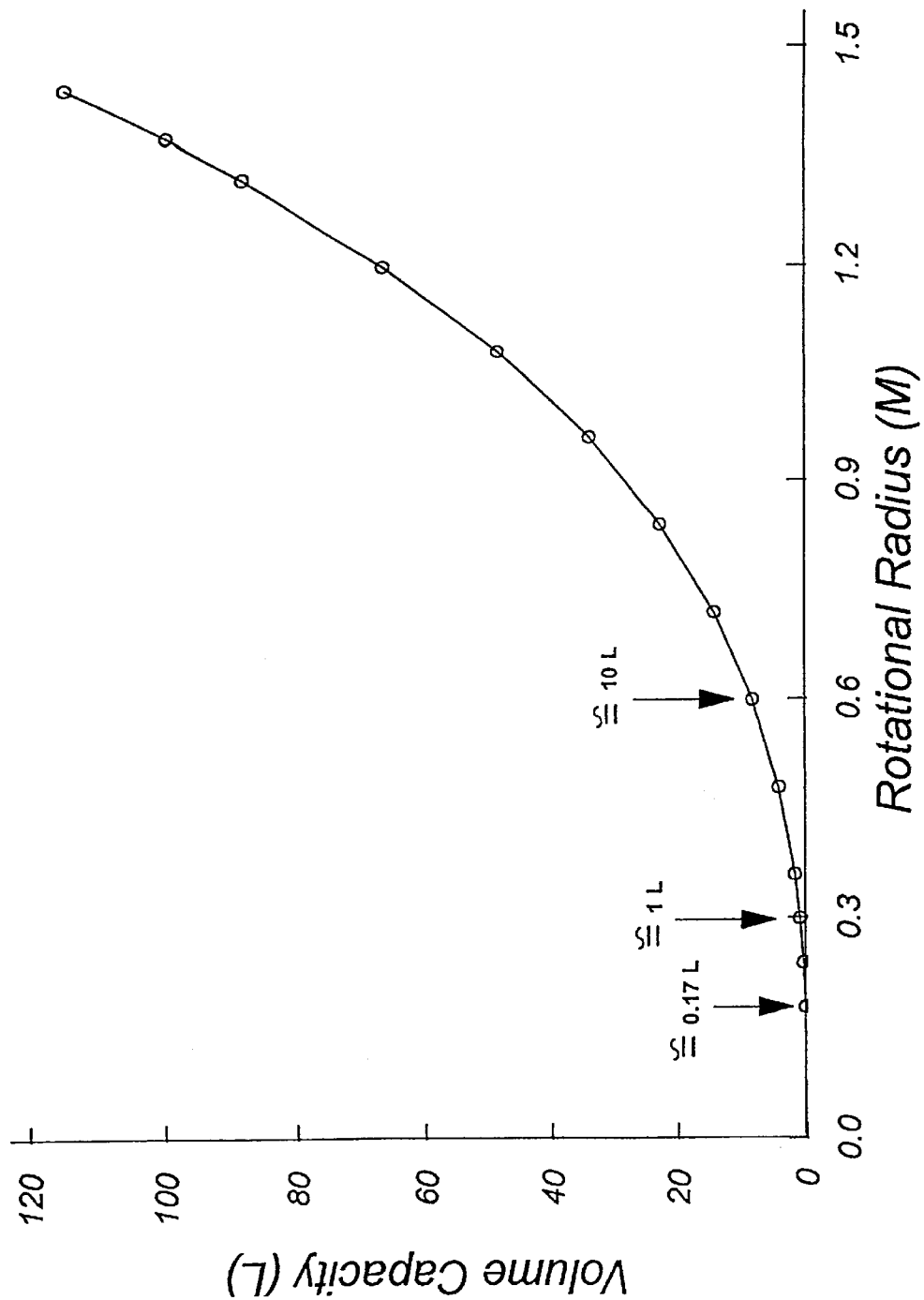
FIG. 42 is a graph displaying the relationship between rotor size and volume capacity in a second embodiment of this invention.

Another less obvious implication of the utility of this process methodology is the effect of scaling. In the first and second embodiments of the present invention, the total volume capacity of the four-bioreactor rotor is ca. 224 mL and 170 mL, respectively. Note, however, that as the radius of the rotor is increased, the volume capacity of the system goes up as the cube of the radius. This is shown in the graph of FIG. 41, in which the leftmost point corresponds to the first embodiment of this invention, and in FIG. 42, in which the leftmost point corresponds to the second embodiment of this invention. A rotor with a radius of 1.5 meters would have a volume capacity of ca. 120 liters. Further, since the average density of culture is roughly 100 times that of conventional culture methods, the equivalent culture volume is proportionally larger. Thus, a centrifugal fermentation unit with a rotor radius of 1.5 m is roughly equivalent to a 12,000 liter fermentation using current technology.

Figure 43:
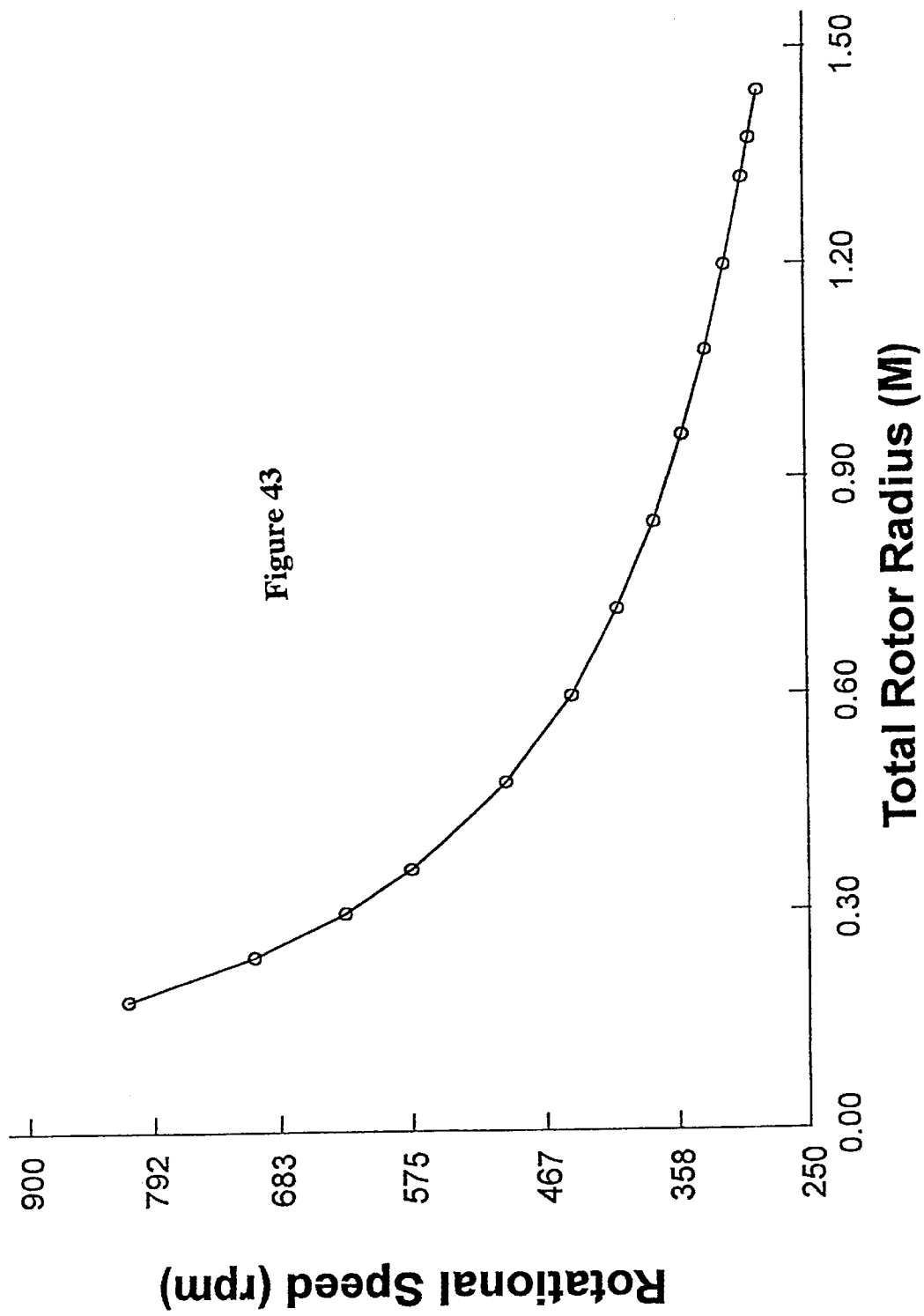
FIG. 43 is a graph displaying the relationship between rotor size and rotational speed required to maintain a Relative Centrifugal Force of 100×g in embodiments of the process of this invention.

Finally, it should be noted that there is an additional advantage in scale in the use of the process of this invention. As a consequence of the fact that relative centrifugal force is directly proportional to the rotor radius but is also directly proportional to the square of the angular velocity, the rotational speeds required to maintain a desired relative centrifugal force decrease as the rotor radius is increased. This is shown graphically in FIG. 43. While the rotational speed required to maintain a RCF=100×g is ca. 810 rpm for a rotor with a radius of 18 cm, this required rotational speed drops to less than 300 rpm when the rotational radius is increased to 1.5 m. This is more than a 50% lowering in the speed of rotation.

While it is obvious that scale-up of this process will have value in industrial production facilities, it should be noted that a miniature embodiment of the Centrifugal Fermentation Process could be valuable in the analytical study of the "metabolic physiology" of small homogeneous populations of a particular cell type. To our knowledge, the exact nutritional requirements for maximal proliferation of, for example, a bacterial population are unknown—and could be rapidly and easily determined by perturbation of the composition of the nutritional liquid input to an immobilized test population while measuring some output parameter indicative of growth. Similarly, while it is desirable to know exactly what nutritional mix is optimal for cellular production of a biological product (a nutritional mix which is highly unlikely to be identical to that which maximizes proliferation), such parameters are, again, unknown. We believe that small-scale versions of the process of this invention could be advantageously utilized in advancing "analytical microbiology" or "analytical cell biology" in a fashion heretofore impossible to perform.

The present invention may also be used for the continuous production of biological products which are secreted or otherwise released into the out-flowing liquid stream. Thus, for example, one might utilize this process for the continual harvest of product(s) which are released from an immobilized micro-organism population whose growth rate (and death rate) have been nutritionally manipulated to maintain a steady state immobilized "bed volume". Such a process could run, theoretically, forever. Similarly, the immobilization of secretory animal cell populations would result in continual outflow of liquid enriched in the desired product (s).

The present invention is also extremely useful in the creation of non-secreted products (such as the cytosolic accumulation of protein in genetically-engineered *E. coli*). If an immobilized cell population is maintained in the bioreactor system outlined above, but under conditions of excess nutritional input, then the population will quickly grow to an enlarged bed size which will continually "leak" excess cells into the out-flowing liquid stream. Thus, the process of this invention can be operated as a "production cow." That is, the present invention can be used as a continual incubator for the production and outflow of mature cells which are rich in the desired product. Downstream isolation and disruption of the out-flowing cell stream to capture the product of interest would then follow conventional product purification methods.

Figure 44:
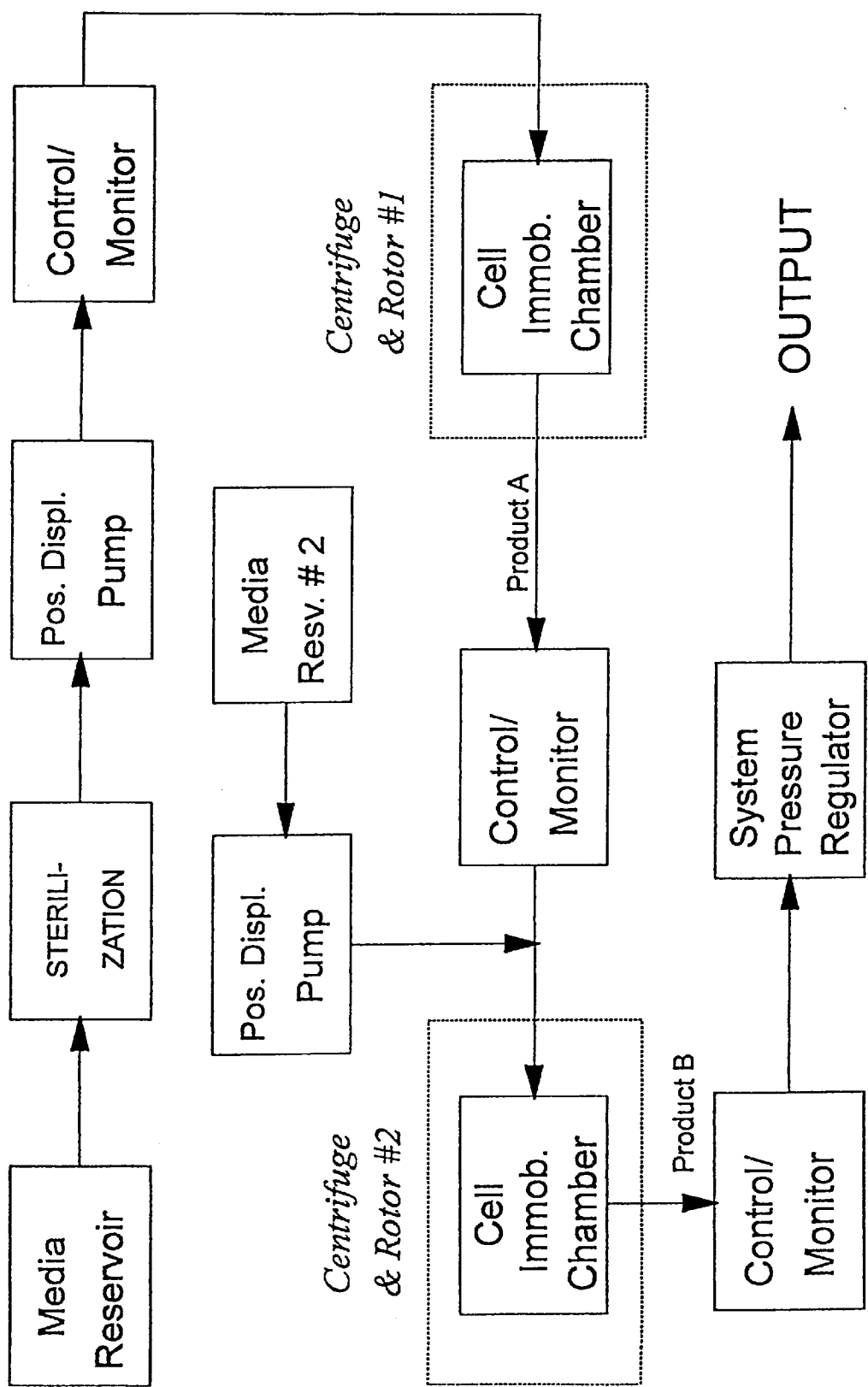
FIG. 44 is a block diagram of a centrifugal process configuration designed to allow serial processing of a precursor chemical through two centrifugal bioreactors.

The process of this invention offers the possibility of continual, serial interconversion of bio-organic substrates through several intermediate steps by two or more separate animal cell populations or micro-organism populations. As a consequence of the ability of the process of this invention to completely immobilize biocatalyst populations while continually flowing a liquid stream into and out of the immobilized population, it now becomes possible to serially connect separate, disparate immobilized populations into one flowing process stream with the assurance that there will be no cross-contamination of one population with the other. To accomplish this, several of the devices described herein are connected in series so that materials flow from one device into another device and then into the following device and so on. As is shown in FIG. 44, a process flow schematic in which a biochemical substrate, which is provided as a dissolved nutrient in the primary media reservoir, is converted into intermediate "product A" by its passage through the biocatalyst population immobilized in Centrifuge and Rotor #1 and is then further converted into "product B" by passage through a biocatalyst population immobilized in Centrifuge and Rotor #2. Furthermore, it is possible to change the composition of the liquid nutritional feedstock between the two immobilized populations since neither centrifuge/rotor combination is constrained to operate at the same flow rate and angular velocity as the other. Thus, as is shown in FIG. 44, the liquid flow into Centrifuge and Rotor #2 may be modified by means of an additional pump supplying necessary nutrients from Media Reservoir #2; the total flow per unit time through Centrifuge and Rotor #2 is simply higher than that through Centrifuge and Rotor #1.

A commercially-valuable example of the utility of a serial conversion process of this type is the biological production of acetic acid. Anaerobic bio-conversion of glucose into ethanol by an immobilized population of a yeast such as *Saccharomyces cerevisiae* in Centrifuge and Rotor #1 could be followed by aerobic conversion of ethanol to acetic acid by an immobilized population of the bacterium *Acetobacter acetii* located in Centrifuge and Rotor #2. This would require that dissolved oxygen and supplemental nutrients be provided via Media Reservoir #2 (using, for example, the oxygenation scheme depicted in FIG. 17).

Similarly, if a process flow scheme demanded that total flow volume per unit time through specific centrifugal bioreactor units be reduced, then a series of identical centrifugal bioreactor units could be connected in parallel to the process stream flow, with the resultant individual flow volume per unit time thereby reduced to the fractional flow through each unit. In this case, the devices of the present invention would be connected in a parallel arrangement.

The microbial organisms which may be used in the present invention include, but are not limited to, dried cells or wet cells harvested from broth by centrifugation or filtration. These microbial cells are classified into the following groups: bacteria, actinomycetes, fungi, yeast, and algae. Bacteria of the first group, belonging to Class Shizomycetes taxonomically, are Genera Pseudomonas, Acetobacter, Gluconobacter, Bacillus, Corynebacterium, Lactobacillus, Leuconostoc, Streptococcus, Clostridium, Brevibacterium, Arthrobacter, or Erwinia, etc. (see R. E. Buchran and N. E. Gibbons, Bergey's Manual of Determinative Bacteriology, 8th ed., (1974), Williams and Wilkins Co.). Actinomycetes of the second group, belonging to Class Shizomycetes taxonomically, are Genera Streptomyces, Nocardia, or Mycobacterium, etc. (see R. E. Buchran and N. E. Gibbons, Bergey's Manual of Determinative Bacteriology, 8th ed., (1974), Williams and Wilkins Co.). Fungi of the third group, belonging to Classes Phycomycetes, Ascomycetes, Fungi imperfecti, and Bacidiomycetes taxonomically, are Genera Mucor, Rhizopus, Aspergillus, Penicillium, Monascus, or Neurosporium, etc. (see J. A. von Ark, "The Genera of Fungi Sporulating in Pure Culture", in Illustrated Genera of Imperfect Fungi, 3rd ed., V. von J. Cramer, H. L. Barnett, and B. B. Hunter, eds. (1970), Burgess Co.). Yeasts of the fourth group, belonging to Class Ascomycetes taxonomically, are Genera Saccharomyces, Zygosaccharomyces, Pichia, Hansenula, Candida, Torulopsis, Rhodotorula, Kloechera, etc. (see J. Lodder, The Yeasts: A Taxonomic Study, 2nd ed., (1970), North-Holland). Algae of the fifth group include green algae belonging to Genera Chlorella and Scedesmus and blue-green algae belonging to Genus Spirulina (see H. Tamiya, Studies on Microalgae and Photosynthetic Bacteria, (1963) Univ. Tokyo Press). It is to be understood that the foregoing listing of micro-organisms is meant to be merely representative of the types of micro-organisms that can be used in the fermentation process according to the present invention.

The culture process of the present invention is also adaptable to plant or animal cells which can be grown either in monolayers or in suspension culture. The cell types include, but are not limited to, primary and secondary cell cultures, and diploid or heteroploid cell lines. Other cells which can be employed for the purpose of virus propagation and harvest are also suitable. Cells such as hybridomas, neoplastic cells, and transformed and untransformed cell lines are also suitable. Primary cultures taken from embryonic, adult, or tumorous tissues, as well as cells of established cell lines can also be employed. Examples of typical such cells include, but are not limited to, primary rhesus monkey kidney cells (MK-2), baby hamster kidney cells (BHK21), pig kidney cells (IBRS2), embryonic rabbit kidney cells, mouse embryo fibroblasts, mouse renal adenocarcinoma cells (RAG), mouse medullary tumor cells (MPC-11), mouse-mouse hybridoma cells (I-15 2F9), human diploid fibroblast cells (FS-4 or AG 1523), human liver adenocarcinoma cells (SK-HEP-1), normal human lymphocytic cells, normal human lung embryo fibroblasts (HEL 299), WI 38 or WI 26 human embryonic lung fibroblasts, HEP No. 2 human epidermoid carcinoma cells, HeLa cervical carcinoma cells, primary and secondary chick fibroblasts, and various cell types transformed with, for example, SV-40 or polyoma viruses (WI 38 VA 13, WI 26 VA 4, TCMK-1, SV3T3, etc.). Other suitable established cell lines employable in the method of the present invention will be apparent to the person of ordinary skill in the art.

The products that can be obtained by practicing the present invention are any metabolic product that is the result of the culturing of a cell, either eukaryotic or prokaryotic; a cell subcellular organelle or component, such as mitochondria, nuclei, lysozomes, endoplasmic reticulum, golgi bodies, peroxisomes, or plasma membranes or combinations thereof; or an enzyme complex, either a natural complex or a synthetic complex, i.e., a plurality of enzymes complexed together to obtain a desired product.

One of the advantages of the present invention is the ability to produce a desired chemical from a cell without having to go through the laborious process of isolating the gene for the chemical and then inserting the gene into a suitable host cell, so that the cell (and thus the chemical) can be produced in commercial quantities. The present invention may be used to directly culture, in high-density, a mammalian cell that is known to produce a desired chemical. By doing this, the present invention may be used to produce large quantities of the desired chemical.

Products that can be produced according the present invention include, but are not limited to, immunomodulators, such as interferons, interleukins, growth factors, such as erythropoietin; monoclonal antibodies; antibiotics from micro-organisms; coagulation proteins, such as Factor VIII; fibrinolytic proteins, such as tissue plasminogen activator and plasminogen activator inhibitors; angiogenic proteins; and hormones, such as growth hormone, prolactin, glucagon, and insulin.

The term "culture medium" includes any medium for the optimal growth of microbial, plant, or animal cells or any medium for enzyme reactions including, but not limited to, enzyme substrates, cofactors, buffers, and the like necessary for the optimal reaction of the enzyme or enzyme system of choice. Suitable culture media for cell growth will contain assimilable sources of nitrogen, carbon, and inorganic salts, and may also contain buffers, indicators, or antibiotics.

Any culture medium known to be optimal for the culture of microorganisms, cells, or biocatalysts may be used in the present invention. While such media are generally aqueous in nature for the culture of living organisms, organic solvents or miscible combinations of water and organic solvents, such as dimethylformamide, methanol, diethyl ether and the like, may be employed in those processes for which they are proved efficacious, such as those bioconversions in which immobilized biocatalysts are employed. Passage of the liquid media through the process system may be either one-pass or the liquid flow may be recycled through the system for higher efficiency of conversion of substrate to product. Desired nutrients and stimulatory chemicals may be introduced into the process flow, either via the low pressure nutrient supply or via injection into the process flow upstream of the cell chamber.

It will be appreciated that the present invention is adaptable to any of the well-known tissue culture media including, but not limited to, Basal Medium Eagle's (BME), Eagle's Minimum Essential Medium (MEM), Dulbecco's Modified Eagle's Medium (DMEM), Ventrex Medium, Roswell Park Medium (RPMI 1640), Medium 199, Ham's F-10, Iscove's Modified Dulbecco Medium, phosphate buffered salts medium (PBS), and Earle's or Hank's Balanced Salt Solution (BSS) fortified with various nutrients. These are commercially-available tissue culture media and are described in detail by H. J. Morton (1970) In Vitro 6, 89–108. These conventional culture media contain known essential amino acids, mineral salts, vitamins, and carbohydrates. They are also frequently fortified with hormones such as insulin, and mammalian sera, including, but not limited to, bovine calf serum as well as bacteriostatic and fungistatic antibiotics.

Although cell growth or cell respiration within the biocatalyst immobilization chamber cannot be directly visualized, such metabolism may be readily monitored by the chemical sensing of substrate depletion, dissolved oxygen content, carbon dioxide production, or the like. Thus, for example in the case of a fermentation of a species of *Saccharomyces cerevisiae,* inoculation of the biocatalyst immobilization chamber with a small starter population of cells can be followed by an aerobic fermentation regime in which glucose depletion, dissolved oxygen depletion, and carbon dioxide production across the biocatalyst immobilization chamber are measured either chemically or via appropriate sensing electrodes. Thus, cell replication can be allowed to proceed until an optimal cell bed size is reached. Withdrawal of dissolved oxygen input at this time causes the immobilized yeast cells to shift into anaerobic fermentation of glucose with a resultant production of ethanol, a process which can likewise be monitored chemically.

Similarly, without any process modification, the process of the present invention can be utilized as a bioreactor for immobilized chemical catalysts, enzymes or enzyme systems. In such a process, a catalyst, an enzyme or an enzyme system is chemically immobilized on a solid support including, but not limited to, diatomaceous earth, silica, alumina, ceramic beads, charcoal, or polymeric or glass beads which are then introduced into the biocatalyst immobilization chamber. The reaction medium, either aqueous, organic, or mixed aqueous and organic solvents, flows through the process system and through the three-dimensional array of solid supports within the bioreactor. The catalyst, enzyme, or enzyme system converts a reactant in the process flow medium into the desired product or products. Similarly, in other applications, either cells or cell components including, but not limited to, vectors, plasmids, or nucleic acid sequences (RNA or DNA) or the like may be immobilized on a solid support matrix and confined for similar utilization in converting an introduced reactant into a desired product.

Commercial application of the present invention can be in the production of medically-relevant, cellularly-derived molecules including, but not limited to, anti-tumor factors, hormones, therapeutic enzymes, viral antigens, antibiotics and interferons. Examples of possible product molecules which might be advantageously prepared using the method of the present invention include, but are not limited to, bovine growth hormone, prolactin, and human growth hormone from pituitary cells, plasminogen activator from kidney cells, hepatitis-A antigen from cultured liver cells, viral vaccines and antibodies from hybridoma cells, insulin, angiogenisis factors, fibronectin, HCG, lymphokines, IgG, etc. Other products will be apparent to a person of ordinary skill in the art.

This invention is further illustrated by the following examples, which are not to be construed in any way as imposing limitations upon the scope thereof. On the contrary, it is to be clearly understood that resort may be had to various other embodiments, modifications, and equivalents thereof which, after reading the description herein, may suggest themselves to those skilled in the art without departing from the spirit of the present invention and/or the scope of the appended claims.

EXAMPLE I

Removal of Heavy Metals from Aqueous Solution

Microbial populations have been shown to be capable of either adsorbing, absorbing, or metabolizing a wide range of inorganic cationic complexes presented to the microbial population in dilute aqueous solution. Further, it has been amply demonstrated that virtually all terrestrial, as well as many marine, microorganisms exist in nature by attachment to a solid support through the agency of either homogeneous or heterogeneous biofilms. We demonstrate herein a novel bioremediation process which exploits these microbial characteristics to remove heavy metals which are presented at low concentration in very large volume aqueous solution.

While it has thought that microbial bioremediation of aqueous heavy metal contaminants would be much cheaper and simpler than current remediation techniques, the central drawback to their employment has been the impossibility of economically processing dilute contaminants. The high flow rates which are typically required for dilute concentrations of contaminants will "wash out" the desired microbial population well before they can perform the desired bioremediation.

A microbial population is immobilized in biocatalyst immobilization chamber or chambers. These chambers are placed into an embodiment of the apparatus shown herein, preferably in the first or second embodiment The flow rate and rotor RPM are chosen to allow the immobilization of a three dimensional array of the chosen microorganism. Since it is essential that the pumped system has only two phases (liquid and solid), the pumped system is maintained at hydraulic pressures above ambient by means of a system pressure regulator downstream of the Biocatalyst Immobilization Chamber(s). Nutrient minerals, organics, and dissolved gas(es) are supplied to the Biocatalyst Immobilization Chamber(s) by the main system pump, Pump 3.

Figure 46:
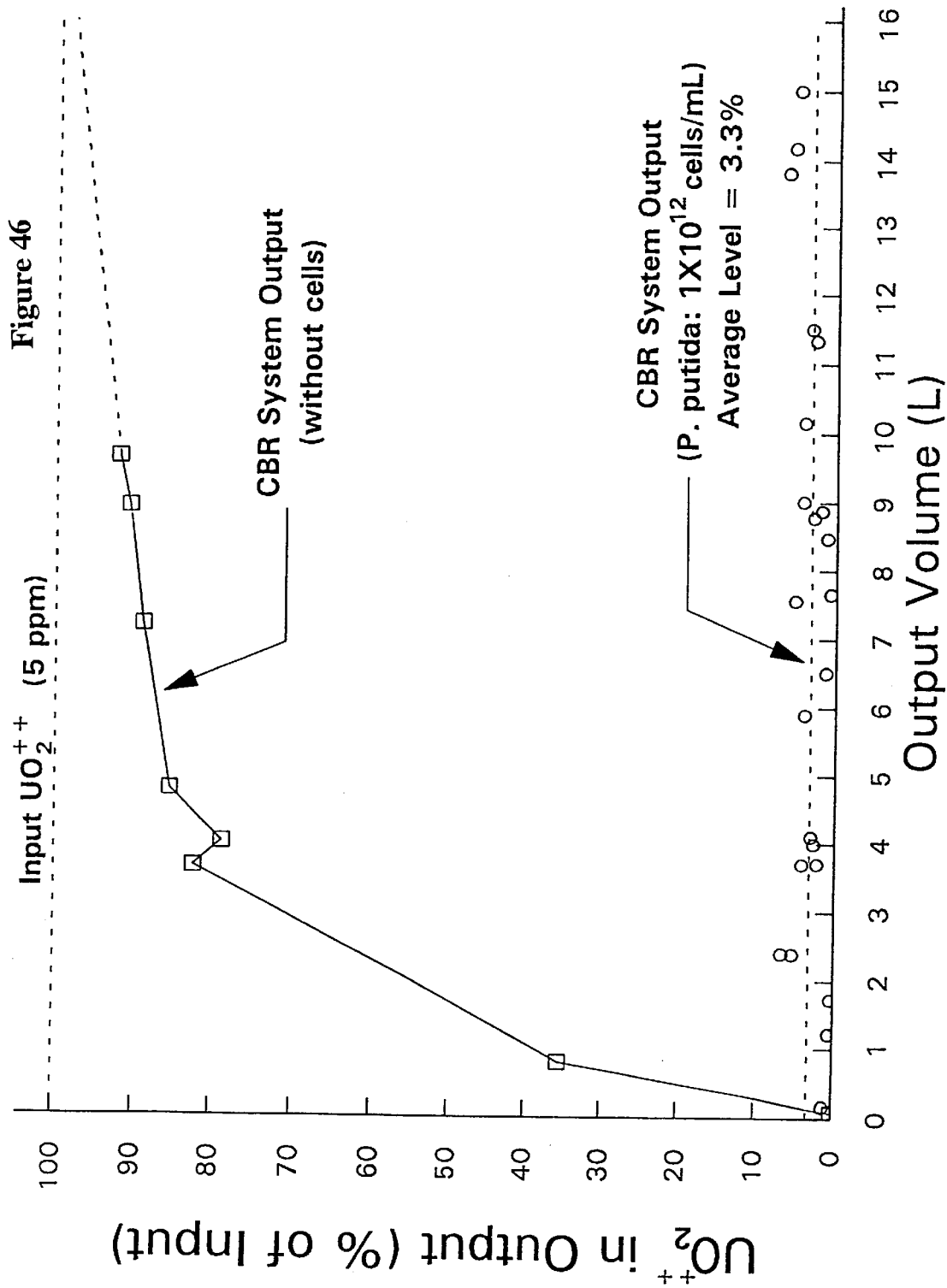
FIG. 46 depicts the results of an example experiment in which, after ca. $1 \times 10^{10}$ P. putida cells were injected into and immobilized in the CBR, a flow of 5 ppm uranyl nitrate (pH=4.7) was started. The CBR output was monitored by ICP-AES for uranyl ion throughput.

Populations of the bacterium, *Pseudomonas putida,* were immobilized and cultured in CBR units (RPM=850, FR=1.0 mL/min, T=37/30° C., pH=6.5, media: LB). Though not wishing to be bound by any particular theory, it was theorized that bacteria of this genus were capable of adsorbing significant quantities of heavy metal ions. These experiments examined the ability of CBR-immobilized populations of several species to remove uranyl ion ($UO_2^{2+}$) from an aqueous solution. Further, since uranyl ions, as groundwater contaminants, are typically found in relatively acidic solutions (pH=4–5), all immobilized cell culture/cell adsorption experiments were performed in acidic solution. We found that all tested species can grow, albeit slowly, under acidic conditions and also adsorb and internalize significant quantities of this environmental pollutant. While populations of *P. aeruginosa* were somewhat superior in uranyl ion uptake, we have concentrated on studying the uptake characteristics of *P. putida* populations since there is a small health risk associated with *P. aeruginosa* handling. The results of an example experiment are shown in FIG. 46. After ca. $1\times10^{10}$ *P. putida* cells were injected into and immobilized in the CBR, a flow of 5 ppm uranyl nitrate (pH=4.7) was started. The CBR output was monitored by ICP-AES for uranyl ion throughput. As is shown on the figure, ca. 16 L of liquid was collected before the output uranyl ion exceeded 5% of its input value, whereas the output uranyl ion exceeds 80% of the input value after the passage of only the passage of 4L in the absence of the cell population. The former represents the adsorption and/or internalization of ca. 31 mg $UO_2^{2+}$ by ca. 826 mg of dry biomass weight.

Processing of large volumes of dilute aqueous solutions of heavy metals using this process proceed by the following steps: (1) loading of a CBR unit with a population of cells; (2) saturation of the immobilized population with the contaminant heavy metal as the dilute solution is passed through the CBR; (3) pelleting and removal of the microorganisms saturated with heavy metal complex from the biocatalyst immobilization chamber(s); and (4) repetition of steps 1–3 until the entire volume of contaminated liquid was processed.

EXAMPLE II

Production of Secreted Products from Microbial Cells

Certain microbial populations have been shown to be capable of the production and secretion of organic molecules when these populations are presented with a nutrient media that will support their viability. In some cases, such nutrient media are supplemented with a stimulatory chemical that supports enhanced production of secretory products.

Microbial secretory production would be much cheaper and simpler if a dense population of the productive microorganism could be maintained in a true chemostat, i.e. in invariant chemical conditions, while secretory products and metabolites were continually removed from the immobilized cellular aggregate, such a process has heretofore not been realizable.

A microbial population was immobilized in biocatalyst immobilization chamber(s). These chambers are placed into one embodiment of the present invention, preferably the first or second embodiments, referred to as a CBR. The flow rate and rotor RPM were chosen to allow the immobilization of a three dimensional array of the chosen microorganism. It is essential that the pumped system has only two phases (liquid and solid), thus the pumped system was maintained at hydraulic pressures above ambient by means of a system pressure regulator downstream of the biocatalyst immobilization chambers. Nutrient minerals, organics, and dissolved gas(es) were supplied to the biocatalyst immobilization chamber by the main system pump, Pump 3.

Figure 47:
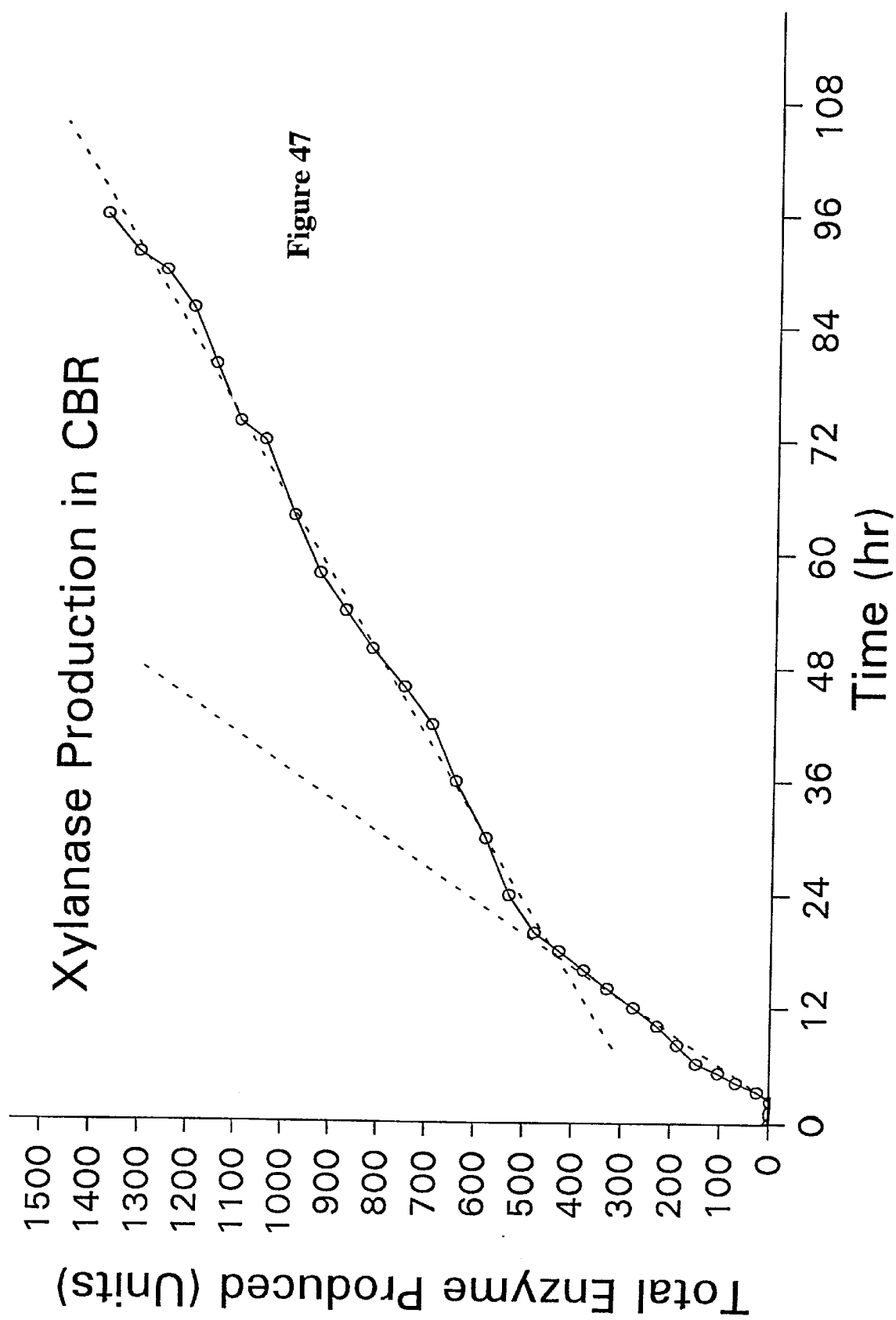
FIG. 47 shows the time course of xylanase production from an A. pullulans culture initially grown up on glucose and subsequently switched (at T=0) to xylose as the media carbon source.

Populations of *Aureobasidium pullulans*, an aerobic yeast, were immobilized and cultured in biocatalyst chambers using the following parameters: RPM=380, Flow Rate=1.0 mL/min, T=22° C., pH=7.1, media: 1% glu, 1% YNB. The immobilized yeast population secreted the enzyme xylanase in response to the introduction of 1% xylose into its nutrient media and the withdrawal of nutrient glucose. FIG. 47 shows the time course of xylanase production from an *A. pullulans* culture initially grown up on glucose and subsequently switched (at T=0) to xylose as the media carbon source. Continuous production of xylanase was observed for more than 96 hours.

A comparison of the production of xylanase in a CBR unit at 25 hrs of culture to an equivalent shake flask at 20 hrs of culture resulted in the determination of xylanase levels of 1.2 U/mL (CBR) and 1.0 U/mL (shake flask) with the CBR-produced enzyme having ca. twice the specific activity of the shake-flask culture. This organism is of particular interest since the sequence of the xylanase gene and its promoter region is known and appears to be usable for the production and secretion of xenoproteins.

EXAMPLE III

Production of Secreted Products from Animal Cells

Certain animal cell populations have been shown to be capable of the production and secretion of organic molecules when these populations are presented with a nutrient media that will support their viability. In some cases, such nutrient media are supplemented with stimulatory chemicals that supports enhanced production of secretory products. This experiment shows a novel production process which exploits these animal cell characteristics to enhance the quantity and purity of secretory products.

Animal cell secretory production would be much cheaper and simpler if a dense population of the productive microorganism could be maintained in a true chemostat, i.e. in invariant chemical conditions, while secretory products and metabolites were continually removed from the immobilized cellular aggregate, such a process has heretofore not been realizable. The process demonstrated herein is the first demonstration of a scalable chemostatic production process for cultured animal cells.

In this new process, an animal cell population was immobilized in biocatalyst immobilization chamber(s). These chambers were placed into one embodiment of the present invention, preferably the first or second embodiment. The flow rate and rotor RPM were chosen to allow the immobilization of a three dimensional array of the chosen cell type. Since it is essential that the pumped system have only two phases (liquid and solid), the pumped system is maintained at hydraulic pressures above ambient by means of a system pressure regulator downstream of the biocatalyst immobilization chambers. Nutrient minerals, organics, and dissolved gases are supplied to the biocatalyst immobilization chamber by the main system pump, Pump 3.

Murine hybridoma pAB122 cells were grown at $1\times10^6$ cells/ml in conventional T flasks. Approximately 100 mls were removed, chilled and the cells were pelleted by centrifugation. The cell pellet was resuspended in 10 ml of ice cold DMEM+10% FBS and injected into the biocatalyst chamber through an inlet while the CBR was running at the conditions RPM=250, FR=1.0 mL/min, T=37° C., pH=7.2, media: DMEM w/10% FBS. The cells were immobilized within the chamber and within approximately 1 hour, the initial collections of output liquid showed the presence of antibody.

We found that the murine hybridoma pAB 122 was easily cultivable in CBR units (RPM=250, FR=1.0 mL/min, T=37° C., pH=7.2, media: DMEM w/10% FBS). This cell line produces and secretes an antibody to the important protein, p53. We observed continuous production of $Ab_{p53}$ from CBR cultures of ca. $1\times10^8$ cells over 5–9 day culture periods. We found that the CBR-immobilized cells produced ca. 60 mg/day of $Ab_{p53}$ continuously over a 3–4 day period. In comparison, a 7-day T-flask culture (50 mL) of ca. $1\times10^8$ cells produced ca. 7 mg/day of $Ab_{p53}$.

In a single 3-day experiment in a CBR in which these cells were perfused with media lacking FBS, the production rate of $Ab_{p53}$ decreased by only one-half, although the time course of this latter production appears to decrease with time. The identity of the product protein produced in the CBR production as $Ab_{p53}$ has been confirmed by Western blots, p53 ELISA assays, and by its co-migration with authentic $Ab_{p53}$ in SDS gels.

EXAMPLE IV

Bioremediation of Low Concentration Contaminants from Large Volume Aqueous Solutions Microbial populations have been shown to be capable of either adsorbing, absorbing, or metabolizing a wide range of organic or inorganic compounds presented to the microbial population in dilute aqueous solution. Further, it has been demonstrated that virtually all terrestrial, as well as many marine, microorganisms exist in nature by attachment to a solid support through the agency of either homogeneous or heterogeneous biofilms. We demonstrate herein a novel bioremediation process which exploits these microbial characteristics to remove water contaminants which are presented at low concentration in very large volume aqueous solution.

Microbial bioremediation of aqueous contaminants would be much cheaper and simpler than current remediation techniques, except that the costs of processing the dilute contaminants is prohibitive. The high flow rates which are typically required to deal with dilute contaminants will "wash out" the desired microbial population well before they can perform the desired bioremediation.

A microbial population, either homogeneous or heterogeneous, was immobilized on a solid support by the formation of biofilms. These solid supports were placed into one embodiment of the present invention, preferably the third embodiment, an example of which is shown in FIG. 45. The size and density of the solid support as well as the tank dimensions were chosen to allow the system pump to achieve the desired throughput flow rate with the generation of an immobilized three-dimensional array of the solid support-microbial cell complexes. Since it is essential that the pumped system has only two phases (liquid and solid), the pumped system was maintained at hydraulic pressures above ambient by means of a system pressure regulator downstream of the biocatalyst immobilization chamber. Nutrient minerals, organics, and dissolved gases were supplied to the biocatalyst immobilization chamber by the main system pump, Pump 3.

Figure 48:
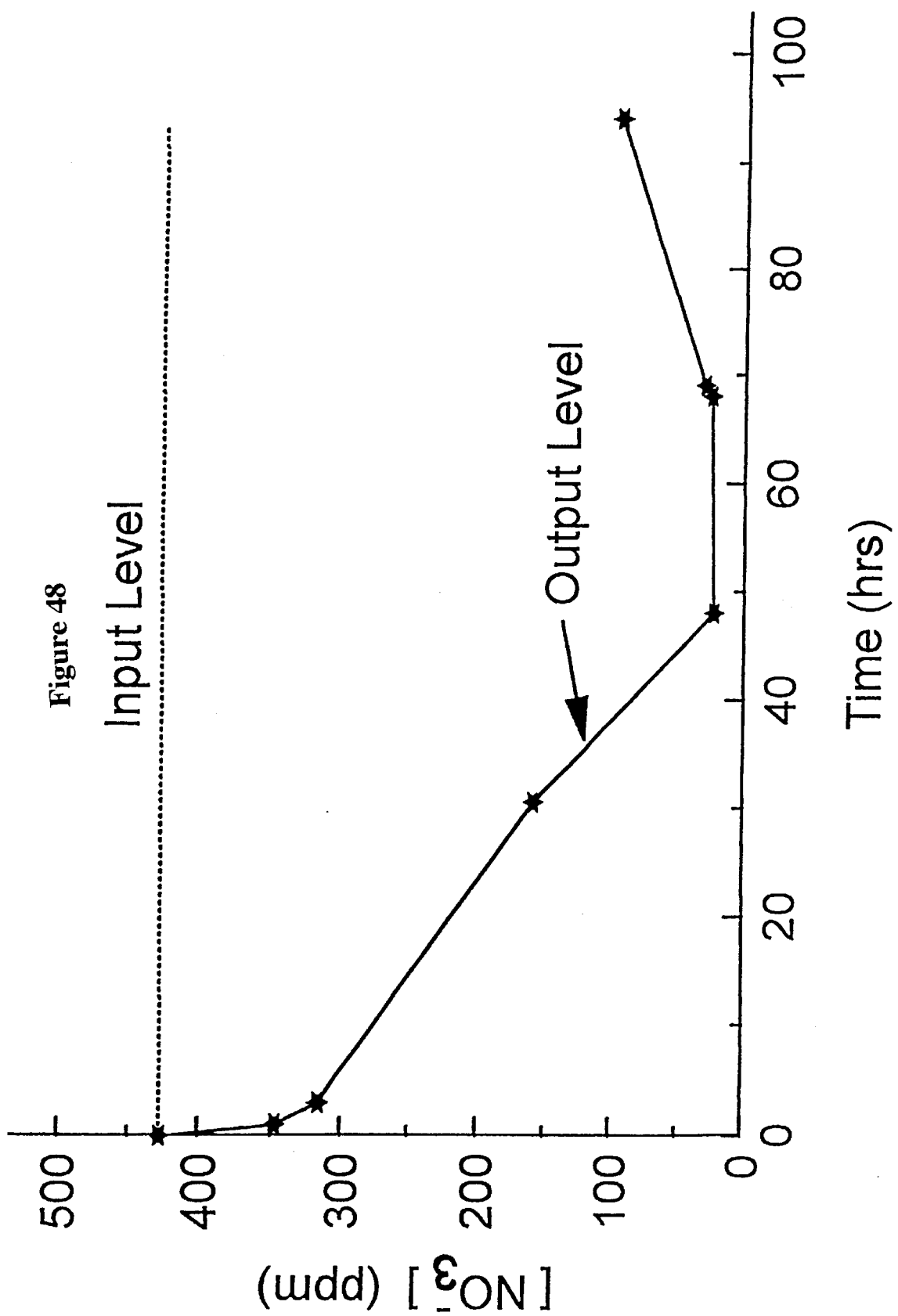
FIG. 48 depicts the result of an analysis of the input vs. the output levels of nitrate ion as measured amperiometrically.

The system of FIG. 45 was used to remove nitrate ion from a dilute aqueous solution, a process of great interest in environmental bioremediation. A biocatalyst immobilization chamber having the following dimensions ($R_1$=5.0 cm, $R_2$=5.1 cm, L=100 cm) was loaded with 100 mL of 30–50 mesh charcoal that had been equilibrated with a shake-flask ferment of *Pseudomonas putida* (strain PRS2000). The media reservoir 1 was loaded with an aqueous solution of 400 ppm sodium nitrate, 0.05 ppm potassium phosphate, and 0.5 ppm ethanol. The gas-liquid adsorption reservoir, 2, was equilibrated with ambient pressure nitrogen gas. The system pressure regulator, 3, was set at 30 psig and Pumps 1–3 set to flow at 120 mL/min. FIG. 48 depicts the result of an analysis of the input vs. the output levels of nitrate ion as measured amperiometrically. Nitrate levels in the system output fell precipitously in the first 8 hours and remained at less than 15% of the input value for the balance of the experiment. Collateral analysis of the output flow indicated that levels of nitrite and nitrous oxide were minimal and the bulk of the nitrate had been converted to molecular nitrogen.

EXAMPLE V

Serial Configurations for CBRs

Figure 49:
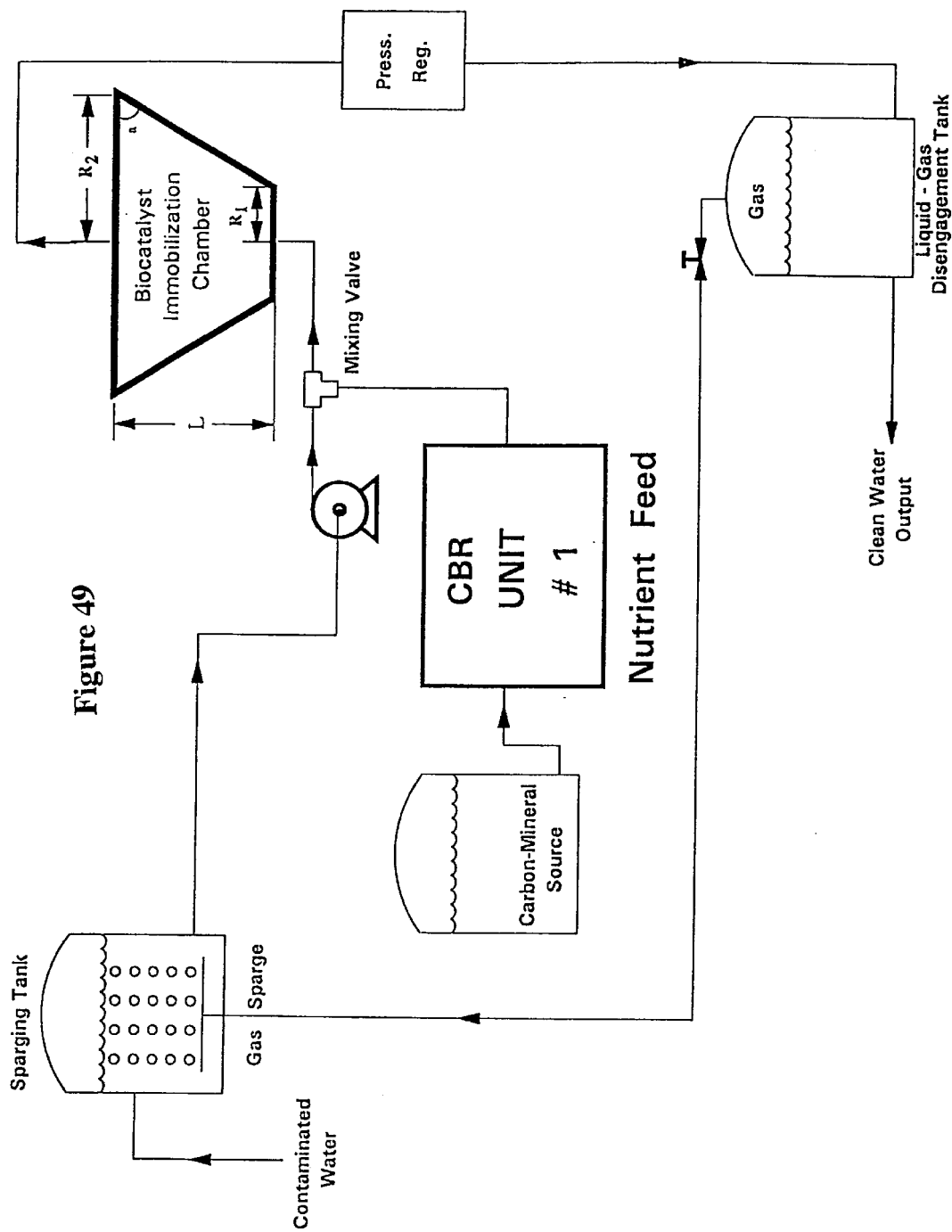
FIG. 49 shows one CBR embodiment to generate ethanol by, for example, anaerobic fermentation of glucose to ethanol by an immobilized fermentative yeast population.

Another arrangement of the present invention that is shown in FIG. 49. The present invention comprises use of several embodiments, or individual CBRs used in serial configurations. The system configuration of FIG. 49 employs one CBR embodiment (shown in the figure as "CBR UNIT #1") to generate ethanol by, for example, anaerobic fermentation of glucose to ethanol by an immobilized fermentative yeast population. The ethanol so produced is then pumped into the downstream Biocatalyst Immobilization Chamber where, as in Example IV above, it serves as a co-substrate for the dissimulatory reduction of nitrate ion. Note further that there can be a wide disparity in the throughput and capacity of each of the serially-connected CBR units. It was shown in Example IV that dissimulation of 400 ppm nitrate required the co-presence of only 0.5 ppm ethanol. In cases such as this, CBR Unit #1 is configured to immobilize a biomass that would be one thousandth of that immobilized in the second unit and would flow at a correspondingly smaller flow rate.

Figure 50:
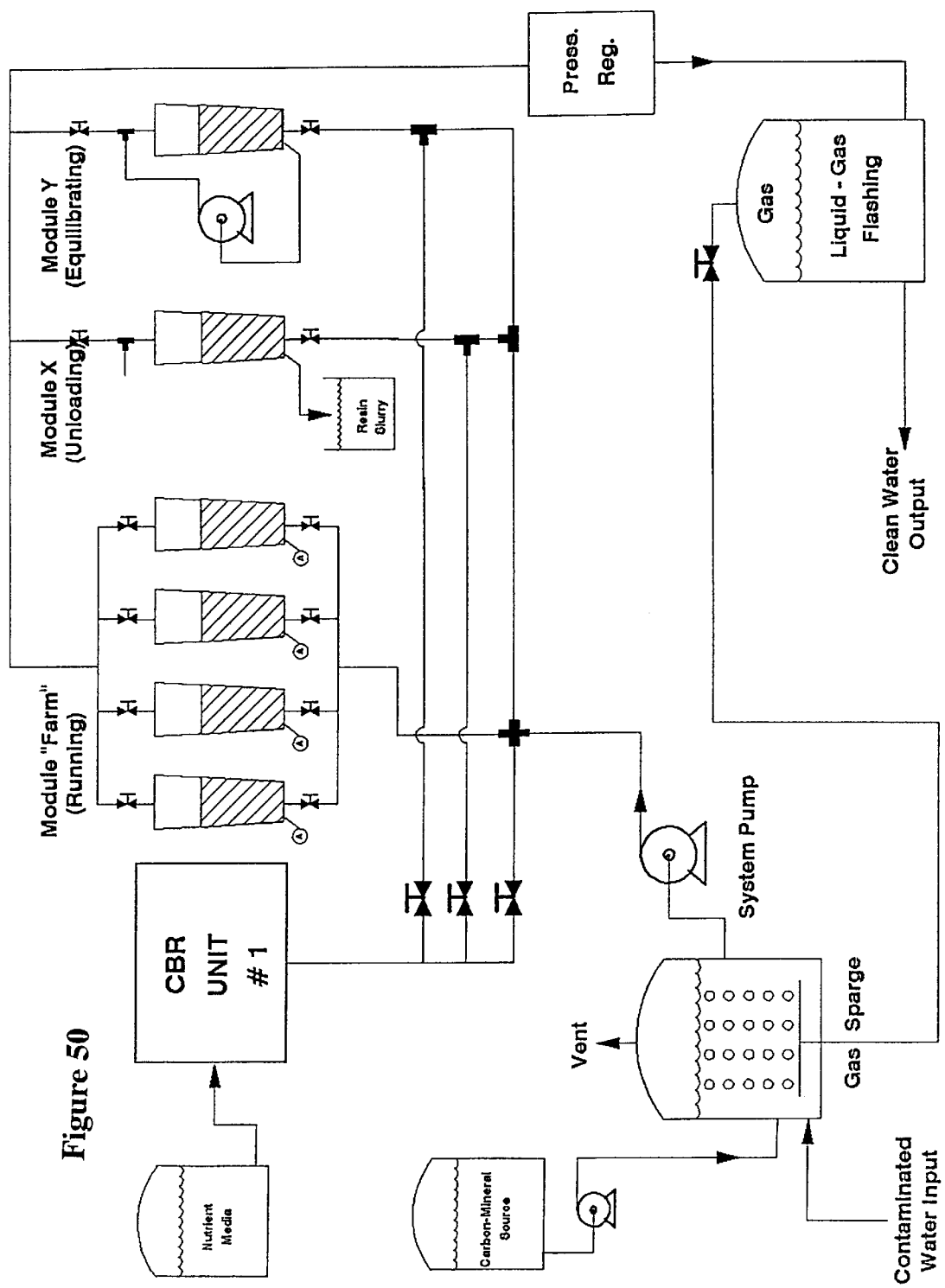
FIG. 50 shows one CBR embodiment to generate replacement microbial cells for periodic introduction into a parallel array of biocatalyst immobilization chambers.

Another arrangement of the present invention is shown in FIG. 50. The system configuration of FIG. 50 employs one CBR embodiment (shown in the figure as "CBR UNIT #1") to generate replacement microbial cells for periodic introduction into a parallel array of biocatalyst immobilization chambers ("Modules" in FIG. 50). The configuration of FIG. 50 contains an array of parallel biocatalyst chambers, also called a "Module Farm", which is identical to the configuration of FIG. 49, except that the System Pump is, in this example, supplying contaminated water to four running biocatalyst immobilization chambers (Modules in FIG. 50) while two additional off-line modules are being prepared for service.

The foregoing description of the present invention is not intended to be exhaustive or to limit the invention to the precise form disclosed. Many modifications and variations are possible. The particular embodiments described are intended to best explain the principles of the invention and its practical application to thereby enable others skilled in the relevant art to best utilize the present invention in various embodiments and with various modifications as are suited to the particular use contemplated. The foregoing description is intended to cover in the appended claims all such modifications, variations, and changes as fall within the scope of the process of this invention.

What is claimed is:

1. A method of producing secreted products from a biocatalyst comprising containing the biocatalyst in at least one chamber in a centrifugal force field wherein a continuous flow of a liquid acts to create a force which opposes the centrifugal force field and wherein a gravitational force contributes to the resultant vector summation of all forces acting on the biocatalyst, wherein the gravitational force, the centrifugal force and the opposing liquid force substantially immobilize the biocatalyst at a position in the chamber, the liquid is at hydraulic pressures greater than ambient pressure, and wherein no gaseous phase is present in said chamber, wherein the biocatalyst produces secreted products.

2. The method of claim 1, wherein containing the biocatalyst comprises a plurality of chambers.

3. The method of claim 1, wherein the liquid contains a dissolved gas.

4. The method of claim 1, wherein the biocatalyst is a cell.

5. The method of claim 1, wherein the biocatalyst is chosen from the group comprising a subcellular component, an enzyme complex, and an enzyme complex immobilized on a solid support.

6. The method of claim 1, wherein the biocatalyst is chosen from the group comprising prokaryotic cells, algae cells, plant cells, yeast cells, fungal cells, insect cells, reptile cells and mammalian cells.

7. The method of claim 1, wherein the liquid contains a dissolved gas chosen from the group comprising air, $O_2$, $CO_2$, methane, $NH_3$, $NO_2$, Ar, He, $N_2$ and $H_2$ or any mixture thereof.

8. A method of removing contaminants from a liquid comprising containing a biocatalyst in at least one chamber in a centrifugal force field wherein a continuous flow of the liquid acts to create a force which opposes the centrifugal force field and wherein a gravitational force contributes to the resultant vector summation of all forces acting on the biocatalyst, wherein the gravitational force, the centrifugal force and the opposing liquid force substantially immobilize the biocatalyst at a position in the chamber, the liquid is at hydraulic pressures greater than ambient pressure, and wherein no gaseous phase is present in said chamber, wherein the biocatalyst removes contaminants from the liquid.

9. The method of claim 8, wherein containing the biocatalyst comprises a plurality of chambers.

10. The method of claim 8, wherein the liquid is an aqueous solution.

11. The method of claim 8, wherein the liquid contains a dissolved gas.

12. The method of claim 8, wherein the liquid contains a dissolved gas chosen from the group comprising air, $O_2$, $CO_2$, methane, $NH_3$, $NO_2$, Ar, He, $N_2$ and $H_2$ or any mixture thereof.

13. The method of claim 8, wherein the biocatalyst is a cell.

14. The method of claim 8, wherein the biocatalyst is chosen from the group comprising a subcellular component, an enzyme complex, and an enzyme complex immobilized on a solid support.

15. The method of claim 8, wherein the biocatalyst is chosen from the group comprising prokaryotic cells, algae cells, plant cells, yeast cells, fungal cells, insect cells, reptile cells and mammalian cells.

16. The method of claim 8, wherein the contaminants are chosen from the group comprising heavy metals and nitrate ions.

* * * * *